US009555090B2

(12) United States Patent
Dupuy et al.

(10) Patent No.: US 9,555,090 B2
(45) Date of Patent: Jan. 31, 2017

(54) EQUINE ENCEPHALITIS VIRUS VACCINES AND METHODS OF USING THEREOF

(75) Inventors: Lesley Dupuy, Frederick, MD (US); Connie S. Schmaljohn, Middletown, MD (US)

(73) Assignee: The United States of America as repesented by the Secretary of Army, on behalf of the U.S. Army Medical Research Institute of Infections Diseases, Washington, DC (US)

( * ) Notice: Subject to any disclaimer, the term of this patent is extended or adjusted under 35 U.S.C. 154(b) by 8 days.

(21) Appl. No.: 14/388,211

(22) PCT Filed: May 25, 2012

(86) PCT No.: PCT/US2012/039573
§ 371 (c)(1),
(2), (4) Date: Oct. 20, 2014

(87) PCT Pub. No.: WO2013/151567
PCT Pub. Date: Oct. 10, 2013

(65) Prior Publication Data
US 2015/0056230 A1    Feb. 26, 2015

Related U.S. Application Data

(60) Provisional application No. 61/620,122, filed on Apr. 4, 2012.

(51) Int. Cl.
*A61K 39/12* (2006.01)
*C12N 7/00* (2006.01)
*A61K 39/00* (2006.01)

(52) U.S. Cl.
CPC ............... *A61K 39/12* (2013.01); *C12N 7/00* (2013.01); *A61K 2039/525* (2013.01); *A61K 2039/5252* (2013.01); *A61K 2039/5254* (2013.01); *A61K 2039/53* (2013.01); *A61K 2039/70* (2013.01); *C12N 2770/36134* (2013.01)

(58) Field of Classification Search
None
See application file for complete search history.

(56) References Cited

U.S. PATENT DOCUMENTS

| 5,185,440 | A | 2/1993 | Davis et al. |
| 6,261,567 | B1 * | 7/2001 | Hart ........................ A61K 39/12 424/199.1 |
| 6,800,289 | B2 | 10/2004 | Nagata et al. |
| 6,936,257 | B1 | 8/2005 | Bennett et al. |
| 7,572,453 | B2 | 8/2009 | Polo et al. |
| 2015/0056230 | A1 * | 2/2015 | Dupuy .................. A61K 39/12 424/186.1 |

OTHER PUBLICATIONS

Wu et al. (Vaccine. 2007; 25: 4368-4375).*
Schmaljohn et al. (Journal of Virology. 1997; 71 (12): 9563-9569).*
Nagata et al. (Vaccine. 2005; 23: 2280-2283).*
Muthumani et al. (Vaccine. 2008; 26: 5128-5134).*
Akahata et al. (Nature Medicine. Mar. 2010; 16 (3): 334-338).*
Dupuy, et al, "DNA vaccines for biodefense", "DNA vaccines for biodefense", 2009, pp. 1739-1754, vol. 8, No. 12, Publisher: Expert Rev. Vaccines.
Dupuy, et al., "Immunogenicity and protective efficacy of a DNA vaccine against Venezuelan equine encephalitis virus . . . ", "Immunogenicity and protective efficacy of a DNA vaccine against Venezuelan equine encephalitis virus aerosol challenge in nonhuman primates", 2010, pp. 7345-7350, vol. 28, Publisher: Vaccine.
Dupuy, et al., "A DNA Vaccine for Venezuelan Equine Encephalitis Virus Delivered . . . ", "A DNA Vaccine for Venezuelan Equine Encephalitis Virus Delivered by Intramuscular Electroporation Elicits High Levels of Neutralizing Antibodies . . . ", 2011.
Eddy, et al., "Field Studies of an Attenuated Venezuelan Equine . . . ", "Field Studies of an Attenuated Venezuelan Equine Encephalomyelitis Vaccine (Strain TC-83)", 1972, pp. 160-163, vol. 5, No. 2, Publisher: Infection and Immunity.
Garmashova, et al., "The Old World and New World Alphaviruses Use Different Virus-Specific . . . ", "The Old World and New World Alphaviruses Use Different Virus-Specific Proteins for Induction of Transcriptional Shutoff", 2007, pp. 2472-2484, vol. 81, No. 5, Publisher: Journal of Virology.
Garmashova, et al., "Analysis of Venezuelan Equine Encephalitis Virus Capsid Protein . . . ", "Analysis of Venezuelan Equine Encephalitis Virus Capsid Protein Function in the Inhibition of Cellular Transcription", 2007, pp. 13552-13565, vol. 81, No. 24, Publisher: Journal of Virology.
International Search Report received in PCT/US2012/039573, mailed Apr. 26, 2013.
Williams, et al., "Improved Efficacy of a Gene Optimised Adenovirus-based Vaccine . . . ", "Improved Efficacy of a Gene Optimised Adenovirus-based Vaccine for Venezuelan Equine Encephalitis Virus", 2009, pp. 118 vol. 6, Publisher: Virology Journal.

* cited by examiner

*Primary Examiner* — Shanon A Foley
(74) *Attorney, Agent, or Firm* — Elizabeth Arwine

(57) ABSTRACT

Disclosed herein are nucleotide sequences which encode a plurality of structural proteins, except the capsid, of an equine encephalitis virus, wherein the nucleotide sequence is codon-optimized for mammalian expression. The nucleotide sequences are codon-optimized for expression in humans. As disclosed herein, the nucleotide sequences confer protection against Venezuelan equine encephalitis virus (VEEV), western equine encephalitis virus (WEEV), and/or eastern equine encephalitis virus (EEEV).

19 Claims, 22 Drawing Sheets

GGGGGGGGGGGGCGCTGAGGTCTGCCTCGTGAAGAAGGTGTTGCTGACTCATACCAGGCCTGAATCGCCCCATCA
TCCAGCCAGAAAGTGAGGGAGCCACGGTTGATGAGAGCTTTGTTGTAGGTGGACCAGTTGGTGATTTTGAACTTT
TGCTTTGCCACGGAACGGTCTGCGTTGTCGGGAAGATGCGTGATCTGATCCTTCAACTCAGCAAAAGTTCGATTT
ATTCAACAAAGCCGCCGTCCCGTCAAGTCAGCGTAATGCTCTGCCAGTGTTACAACCAATTAACCAATTCTGATT
AGAAAAACTCATCGAGCATCAAATGAAACTGCAATTTATTCATATCAGGATTATCAATACCATATTTTTGAAAAA
GCCGTTTCTGTAATGAAGGAGAAAACTCACCGAGGCAGTTCCATAGGATGGCAAGATCCTGGTATCGGTCTGCGA
TTCCGACTCGTCCAACATCAATACAACCTATTAATTTCCCCTCGTCAAAAATAAGGTTATCAAGTGAGAAATCAC
CATGAGTGACGACTGAATCCGGTGAGAATGGCAAAAGCTTATGCATTTCTTTCCAGACTTGTTCAACAGGCCAGC
CATTACGCTCGTCATCAAAATCACTCGCATCAACCAAACCGTTATTCATTCGTGATTGCGCCTGAGCGAGACGAA
ATACGCGATCGCTGTTAAAAGGACAATTACAAACAGGAATCGAATGCAACCGGCGCAGGAACACTGCCAGCGCAT
CAACAATATTTTCACCTGAATCAGGATATTCTTCTAATACCTGGAATGCTGTTTTCCCGGGGATCGCAGTGGTGA
GTAACCATGCATCATCAGGAGTACGGATAAAATGCTTGATGGTCGGAAGAGGCATAAATTCCGTCAGCCAGTTTA
GTCTGACCATCTCATCTGTAACATCATTGGCAACGCTACCTTTGCCATGTTTCAGAAACAACTCTGGCGCATCGG
GCTTCCCATACAATCGATAGATTGTCGCACCTGATTGCCCGACATTATCGCGAGCCCATTTATACCCATATAAAT
CAGCATCCATGTTGGAATTTAATCGCGGCCTCGAGCAAGACGTTTCCCGTTGAATATGGCTCATAACACCCCTTG
TATTACTGTTTATGTAAGCAGACAGTTTTATTGTTCATGATGATATATTTTTATCTTGTGCAATGTAACATCAGA
GATTTTGAGACACAACGTGGCTTTCCCCCCCCCCCCGGCATGCCTGCAGGTCGACATAAATCAATATTGGCTATT
GGCCATTGCATACGTTGTATCTATATCATAATATGTACATTTATATTGGCTCATGTCCAATATGACCGCCATGTT
GACATTGATTATTGACTAGTTATTAATAGTAATCAATTACGGGGTCATTAGTTCATAGCCCATATATGGAGTTCC
GCGTTACATAACTTACGGTAAATGGCCCGCCTCGTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCA
CTTGGCAGTACATCAAGTGTATCATATGCCAAGTCCGGCCCCCTATTGACGTCAATGACGGTAAATGGCCCGCCT
GGCATTATGCCCAGTACATGACCTTACGGGACTTTCCTACTTGGCAGTACATCTACGTATTAGTCATCGCTATTA
CCATGGTGATGCGGTTTTGGCAGTACACCAATGGGCGTGGATAGCGGTTTGACTCACGGGGATTTCCAAGTCTCC
ACCCCATTGACGTCAATGGGAGTTTGTTTTGGCACCAAAATCAACGGGACTTTCCAAAATGTCGTAATAACCCCG
CCCCGTTGACGCAAATGGGCGGTAGGCGTGTACGGTGGGAGGTCTATATAAGCAGAGCTCGTTTAGTGAACCGTC
AGATCGCCTGGAGACGCCATCCACGCTGTTTTGACCTCCATAGAAGACACCGGGACCGATCCAGCCTCCGCGGCC
GGGAACGGTGCATTGGAACGCGGATTCCCCGTGCCAAGAGTGACGTAAGTACCGCCTATAGACTCTATAGGCACA
CCCCTTTGGCTCTTATGCATGCTATACTGTTTTTGGCTTGGGGCCTATACACCCCCGCTCCTTATGCTATAGGTG
ATGGTATAGCTTAGCCTATAGGTGTGGGTTATTGACCATTATTGACCACTCCCCTATTGGTGACGATACTTTCCA
TTACTAATCCATAACATGGCTCTTTGCCACAACTATCTCTATTGGCTATATGCCAATACTCTGTCCTTCAGAGAC
TGACACGGACTCTGTATTTTTACAGGATGGGGTCCCATTTATTATTTACAAATTCACATATACAACAACGCCGTC
CCCCGTGCCCGCAGTTTTTATTAAACATAGCGTGGGATCTCCACGCGAATCTCGGGTACGTGTTCCGGACATGGG
CTCTTCTCCGGTAGCGGCGGAGCTTCCACATCCGAGCCCTGGTCCCATGCCTCCAGCGGCTCATGGTCGCTCGGC
AGCTCCTTGCTCCTAACAGTGGAGGCCAGACTTAGGCACAGCACAATGCCCACCACCACCAGTGTGCCGCACAAG
GCCGTGGCGGTAGGGTATGTGTCTGAAAATGAGCTCGGAGATTGGGCTCGCACCGTGACGCAGATGGAAGACTTA
AGGCAGCGGCAGAAGAAGATGCAGGCAGCTGAGTTGTTGTATTCTGATAAGAGTCAGAGGTAACTCCCGTTGCGG
TGCTGTTAACGGTGGAGGGCAGTGTAGTCTGAGCAGTACTCGTTGCTGCCGCGCGCGCCACCAGACATAATAGCT
GACAGACTAACAGACTGTTCCTTTCCATGGGTCTTTTCTGCAGTCACCGTCCAAGCTTGCGGCCGCGCCACC*AG
ATCTACGTATGATCAGCCTCGACTGTGCCTTCTAGTTGCCAGCCATCTGTTGTTTGCCCCTCCCCCGTGCCTTCC
TTGACCCTGGAAGGTGCCACTCCCACTGTCCTTTCCTAATAAAATGAGGAAATTGCATCGCATTGTCTGAGTAGG
TGTCATTCTATTCTGGGGGGTGGGGTGGGGCAGGACAGCAAGGGGGAGGATTGGGAAGACAATAGCAGGCATGCT
GGGGATGCGGTGGGCTCTATGGCTTCTGAGGCGGAAAGAACCAGCTGGGGCTCGACAGCTCGACTCTAGAATTGC
TTCCTCGCTCACTGACTCGCTGCGCTCGGTCGTTCGGCTGCGGCGAGCGGTATCAGCTCACTCAAAGGCGGTAAT
ACGGTTATCCACAGAATCAGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCACAAAAATCGACGCTCAAG
TCAGAGGTGGCGAAACCCGACAGGACTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGGGAAGCGTGGCGCTTTCTCAATGCTC
ACGCTGTAGGTATCTCAGTTCGGTGTAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAAGACACGACTTATCGCCACTGGCAGC
AGCCACTGGTAACAGGATTAGCAGAGCGAGGTATGTAGGCGGTGCTACAGAGTTCTTGAAGTGGTGGCCTAACTA
CGGCTACACTAGAAGGACAGTATTTGGTATCTGCGCTCTGCTGAAGCCAGTTACCTTCGGAAAAAGAGTTGGTAG
CTCTTGATCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGAAAACTCACGTTAAGG
GATTTTGGTCATGAGATTATCAAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACCTATCTCAGCGATCTG
TCTATTTCGTTCATCCATAGTTGCCTGACTC

* represents the inserted $EEV_{CO}$ sequence

Fig. 31

SEQUENCE LISTING

```
<160> NUMBER OF SEQ ID NOS: 9

<210> SEQ ID NO 1
<211> LENGTH: 2949
<212> TYPE: DNA
<213> ORGANISM: Artificial Sequence
<220> FEATURE:
<223> OTHER INFORMATION: Based on equine encephalitis virus

<400> SEQUENCE: 1
atgagcctgg tgaccaccat gtgcctgctg gccaacgtga ccttccctg cgcccagccc      60 cccatctgct acgaccggaa gcccgccgag accctggcca tgctgtccgt gaacgtggac     120
aaccccggct acgacgagct gctggaagcc gccgtgaagt gccccggcag gaagcggcgg     180
agcaccgagg aactgttcaa agagtacaag ctgacccggc cctacatggc ccggtgcatc     240
agatgcgccg tgggcagctg ccacagcccc atcgccatcg aggccgtgaa gagcgacggc     300
cacgacggct acgtgcggct gcagaccagc agccagtacg gcctggacag cagcggcaac     360
ctgaagggcc ggaccatgag atacgacatg cacggcacca tcaaagagat cccccctgcac     420 caggtgtccc tgcacaccag ccggccctgc cacatcgtgg acggccacgg ctactttctg     480
ctggccaggt gccctgccgg cgacagcatc accatggaat tcaagaaaga cagcgtgacc     540
cacagctgca gcgtgcccta cgaggtgaag ttcaaccccg tgggccggga gctgtacacc     600 caccccccg agcacggcgt ggagcaggcc tgccaggtgt acgcccacga cgcccagaac     660
```

```
aggggcgcct acgtggagat gcacctgccc ggcagcgagg tggacagctc cctggtgtcc    720
ctgagcggca gcagcgtgac cgtgaccccc cctgtgggca ccagcgccct ggtggagtgc    780
gagtgcggcg gcaccaagat cagcgagacc atcaacaaga ccaagcagtt cagccagtgc    840
accaagaaag agcagtgccg ggcctaccgg ctgcagaacg acaagtgggt gtacaacagc    900
gacaagctgc ccaaagccgc cggagccacc ctgaagggca agctgcacgt gccttttctg    960
ctggctgacg gcaagtgcac cgtgcccctg gcccccgagc ccatgatcac cttcggcttc   1020
agaagcgtga gcctgaagct gcaccccaag aaccccacct acctgaccac ccggcagctg   1080
gccgatgagc cccactacac ccacgagctg atcagcgagc ccgccgtgcg gaacttcacc   1140
gtgaccgaga agggctggga gttcgtgtgg ggcaaccacc cccccaagag gttctgggct   1200
caggaaacag cccctggcaa ccccacggc ctgcctcacg aggtgatcac ccactactac   1260
cacagatacc ccatgagcac catcctgggc ctgagcatct gccgccgccat cgccaccgtg   1320 agcgtggccg ccagcacctg gctgttctgc cggtcccggg tggcctgcct gaccccctac   1380
aggctgaccc ccaacgcccg gatccccttc tgcctggccg tgctgtgctg cgcccggacc   1440
gccagagccg agaccacctg ggagagcctg gaccacctgt ggaacaacaa ccagcagatg   1500
ttctggatcc agctgctgat ccccctggcc gccctgatcg tggtgacccg gctgctgaga   1560
tgcgtgtgct gcgtggtgcc cttcctggtg atggccgggg ctgcaggggc cggcgcctat   1620
gagcacgcca ccaccatgcc cagccaggcc ggcatcagct acaacaccat cgtgaacagg   1680
gccggctacg cccccctgcc catcagcatc acccctacca agatcaagct gatccccacc   1740
gtgaacctgg aatacgtgac ctgccactac aagaccggca tggacagccc cgccatcaag   1800
tgctgcggca gccaggaatg cacccccacc tacaggcccg acgagcagtg caaggtgttc   1860
accggcgtgt accccttcat gtggggcgga gcctactgct ctgcgacac cgagaacacc   1920 caggtgtcca aggcctacgt gatgaagtcc gacgattgcc tggccgacca cgccgaggcc   1980
tacaaggccc acaccgccag cgtgcaggcc ttcctgaaca tcaccgtggg cgagcacagc   2040
atcgtgacca ccgtgtacgt gaacggcgag acccccgtga acttcaacgg cgtgaagctg   2100
accgccggac ccctgagcac cgcctggacc cccttcgacc cggaagatcgt gcagtacgcc   2160 ggcgaaatct acaactacga cttccccgag tatggcgccg acagcctgg cgccttcggc   2220 gacatccaga gccggaccgt gagcagcagc gacctgtacg ccaacaccaa cctggtgctg   2280
cagcggccca aggccggagc catccacgtg ccctacaccc aggcccccag cggcttcgag   2340
cagtggaaga aggacaaggc cccctccctg aagttcaccg cccccttcgg ctgtgaaatc   2400
tacaccaacc ccatccgggc cgagaactgt gccgtgggct ccatccсctct ggccttcgac   2460 atccccgacc cctgttcac cagagtgtcc gagaccccca ccctgtctgc cgccgagtgc   2520
accctgaacg agtgcgtcta ctcctctgac ttcggcggca tcgccacagt gaagtacagc   2580
gccagcaaga cggcaagtg tgccgtgcac gtgcccagcg cacagccac actgaaggaa   2640 gccgccgtgg agctgaccga gcagggcagc gccaccatcc acttcagcac cgccaacatc   2700
caccccgagt tcaggctgca gatttgcacc agctacgtga catgcaaggg cgactgccac   2760 ccсcсctaagg accacatcgt gacccacccc cagtaccacg cccagacctt cacagccgcc   2820
gtgtccaaga cagcctggac ctggctgacc agcctgctgg gcggcagcgc cgtgatcatc   2880
atcatcggcc tggtgctggc caccatcgtg gccatgtacg tgctgaccaa ccagaaacac   2940
aactgatga                                                          2949
```

<210> SEQ ID NO 2
<211> LENGTH: 3771
<212> TYPE: DNA
<213> ORGANISM: Artificial Sequence
<220> FEATURE:
<223> OTHER INFORMATION: Based on equine encephalitis virus

<400> SEQUENCE: 2

```
atgttcccat tccagcccat gtaccccatg cagcccatgc cctaccggaa cccctttgcc      60
gccccctcgga ggccctggtt ccccccggacc gaccccttcc tggccatgca ggtgcaggaa    120
ctgaccagaa gcatggccaa cctgaccttc aagcagcggc gggacgcccc tcctgagggc     180
ccctccgcca agaagcccaa gaaagaggcc agccagaagc agaagggcgg agggcagggc     240
aagaagaaga aaaaccaggg gaagaagaaa gccaagaccg gcctcccaa ccccaaggcc      300
cagaacggca acaagaaaaa gaccaacaag aagcccggca gcggcagcg gatggtgatg      360
aagctggaaa gcgacaagac cttccccatc atgctggaag caagatcaa cggctacgcc     420
tgcgtggtgg gcggcaagct ctttagaccc atgcacgtgg agggcaaaat tgacaacgac    480
gtgctggccg ccctgaaaac caagaaggcc agcaagtacg acctggaata cgccgacgtg   540
ccccagaaca tgcgggccga caccttcaag tacacccacg agaagcccca gggctactac   600
agctggcacc acggagccgt gcagtacgag aacggccggt tcaccgtgcc caagggcgtc   660
ggcgccaagg gcgacagcgg cagacccatc ctggacaacc agggccgggt ggtggccatc   720
gtgctgggcg gcgtgaacga gggcagccgg accgccctga gcgtggtgat gtggaacgag   780
aagggcgtga ccgtgaagta caccctgag aactgcgagc agtggagcct ggtgaccacc     840
atgtgcctgc tggccaacgt gaccttcccc tgcgcccagc ccccatctg ctacgaccgg     900
aagcccgccg agaccctggc catgctgtcc gtgaacgtgg acaacccgg ctacgacgag    960
ctgctggaag ccgccgtgaa gtgccccggc aggaagcggc ggagcaccga ggaactgttc    1020
aaagagtaca gctgacccg gccctacatg gccggtgca tcagatgcgc cgtgggcagc    1080
tgccacagcc ccatcgccat cgaggccgtg aagagcgacg ccacgacgg ctacgtgcgg    1140
ctgcagacca gcagccagta cggcctggac agcagcggca acctgaaggg ccggaccatg   1200
agatacgaca tgcacggcac catcaaagag atccccctgc accaggtgtc cctgcacacc   1260
agccggccct gccacatcgt ggacggccac ggctactttc tgctggccag gtgccctgcc   1320
ggcgacagca tcaccatgga attcaagaaa gacagcgtga cccacagctg cagcgtgccc   1380
tacgaggtga gttcaaccc cgtgggccgg gagctgtaca cccacccccc cgagcacggc    1440
gtggagcagg cctgccaggt gtacgccac gacgcccaga cagggggcgc ctacgtggag   1500
atgcacctgc ccggcagcga ggtggacagc tccctggtgt ccctgagcgg cagcagcgtg   1560
accgtgaccc cccctgtggg caccagcgcc ctggtggagt gcgagtgcgg cggcaccaag   1620
atcagcgaga ccatcaacaa gaccaagcag ttcagccagt gcaccaagaa agagcagtgc   1680
cgggcctacc ggctgcagaa cgacaagtgg gtgtacaaca cgacaagct gcccaaagcc   1740
gccggagcca ccctgaaggg caagctgcac gtgccttttc tgctggctga cggcaagtgc   1800
accgtgcccc tggccccga gcccatgatc accttcggct tcagaagcgt gagcctgaag   1860
ctgcaccca gaaccccac ctacctgacc accggcagc tggccgatga gccccactac   1920
acccacgagc tgatcagcga gccgccgtg cggaacttca ccgtgaccga gaagggctgg   1980
gagttcgtgt gggcaacca cccccccaag aggttctggg ctcaggaaac agcccctggc   2040
aacccccacg gcctgcctca cgaggtgatc acccactact accacagata ccccatgagc   2100
```

```
accatcctgg gcctgagcat ctgcgccgcc atcgccaccg tgagcgtggc cgccagcacc    2160
tggctgttct gccggtcccg ggtggcctgc ctgaccccct acaggctgac ccccaacgcc    2220
cggatcccct tctgcctggc cgtgctgtgc tgcgcccgga ccgccagagc cgagaccacc    2280
tgggagagcc tggaccacct gtggaacaac aaccagcaga tgttctggat ccagctgctg    2340 atcccctgg ccgccctgat cgtggtgacc cggctgctga gatgcgtgtg ctgcgtggtg    2400
cccttcctgg tgatggccgg ggctgcaggg gccggcgcct atgagcacgc caccaccatg    2460
cccagccagg ccggcatcag ctacaacacc atcgtgaaca gggccggcta cgcccccctg    2520
cccatcagca tcacccctac caagatcaag ctgatcccca ccgtgaacct ggaatacgtg    2580
acctgccact acaagaccgg catggacagc cccgccatca gtgctgcgg cagccaggaa    2640 tgcaccccca cctacaggcc cgacgagcag tgcaaggtgt tcaccggcgt gtacccttc    2700 atgtggggcg gagcctactg cttctgcgac accgagaaca cccaggtgtc caaggcctac    2760
gtgatgaagt ccgacgattg cctggccgac cacgccgagg cctacaaggc ccacaccgcc    2820
agcgtgcagg ccttcctgaa catcaccgtg ggcgagcaca gcatcgtgac caccgtgtac    2880
gtgaacggcg agaccccgt gaacttcaac ggcgtgaagc tgaccgccgg acccctgagc    2940
accgcctgga ccccctcga ccggaagatc gtgcagtacg ccggcgaaat ctacaactac    3000
gacttccccg agtatggcgc cggacagcct ggcgccttcg cgacatcca gagcggacc    3060 gtgagcagca gcgacctgta cgccaacacc aacctggtgc tgcagcggcc caaggccgga    3120
gccatccacg tgccctacac ccaggccccc agcggcttcg agcagtggaa gaaggacaag    3180
gccccctccc tgaagttcac cgcccccttc ggctgtgaaa tctacaccaa ccccatccgg    3240
gccgagaact gtgccgtggg ctccatccct ctggccttcg acatccccga cgccctgttc    3300
accagagtgt ccgagacccc caccctgtct gccgccgagt gcaccctgaa cgagtgcgtc    3360
tactcctctg acttcggcgg catcgccaca gtgaagtaca gcgccagcaa gagcggcaag    3420
tgtgccgtgc acgtgcccag cggcacagcc acactgaagg aagccgccgt ggagctgacc    3480
gagcagggca gcgccaccat ccacttcagc accgccaaca tccacccga gttcaggctg    3540 cagatttgca ccagctacgt gacatgcaag ggcgactgcc accccctaa ggaccacatc    3600 gtgacccacc cccagtacca cgcccagacc ttcacagccg ccgtgtccaa gacagcctgg    3660
acctggctga ccagctgct gggcggcagc ccgtgatca tcatcatcgg cctggtgctg    3720
gccaccatcg tggccatgta cgtgctgacc aaccagaaac acaactgatg a            3771
```

<210> SEQ ID NO 3
<211> LENGTH: 2952
<212> TYPE: DNA
<213> ORGANISM: Artificial Sequence
<220> FEATURE:
<223> OTHER INFORMATION: Based on equine encephalitis virus

<400> SEQUENCE: 3

```
atgagcctgg ccaccgtgat gtgcgtgctg gccaacatca ccttcccttg cgaccagccc      60
ccctgcatgc cctgctgcta cgagaagaac ccccacgaga ccctgaccat gctggaacag     120
aactacgaca gccgggccta cgaccagctg ctggacgccg ccgtgaagtg caacgccagg     180
cggaccaggc gggacctgga cacccacttc acccagtaca agctggccag ccctacatc     240 gccgactgcc ccaactgcgg ccacagcaga tgcgacagcc catcgccat cgaggaagtg     300 agaggcgacg cccatgctgg agtcatccgg atccagacca gcgccatgtt cggcctgaaa     360
```

```
accgacggcg tggacctggc ctacatgagc ttcatgaacg gcaagaccca gaagagcatc    420
aagatcgaca acctgcacgt gcggacctcc gccccctgca gcctggtgtc ccaccacggc    480
tactacatcc tggcccagtg ccccctggc gacaccgtga ccgtgggctt ccacgacggc     540
cccaaccggc acacctgcac cgtggcccac aaggtggagt tccggcccgt gggccgggag    600
aagtaccggc acccccccga gcacggcgtg gagctgccct gcaaccggta cacccacaag    660
cgggccgacc agggccacta cgtggagatg caccagcccg gcctggtggc cgaccacagc    720
ctgctgtcca tccacagcgc caaggtgaaa atcaccgtgc ccagcggagc ccaggtgaag    780
tactactgca agtgccccga cgtgcgggag ggcatcacca gcagcgacca caccaccacc    840
tgtaccgacg tgaagcagtg cagggcctac ctgatcgaca acaagaaatg ggtgtacaac    900
agcggcaggc tgcccagagg cgagggcgac accttcaagg gcaagctgca cgtgcccttc    960
gtgcccgtga aggccaagtg catcgccacc ctggcccccg agccctggt ggagcacaag    1020 caccggaccc tgatcctgca cctgcacccc gaccacccca ccctgctgac caccagaagc    1080
ctgggcagca cgccaaccc cacccggcag tggatcgagc ggcccaccac cgtgaacttt    1140
accgtgaccg gcgagggcct ggaatacacc tggggcaacc accccccaa gagagtgtgg    1200 gcccaggaaa gcgcgaggg caaccctcac ggctggcccc acgaagtggt ggtctactac    1260
tacaacagat accccctgac caccatcatc ggcctgtgca cctgcgtggc catcatcatg    1320
gtgtcctgcg tgaccagcgt gtggctgctg tgccggaccc ggaacctgtg catcacccccc   1380 tataagctgg cccccaacgc ccaggtgccc atcctgctgg ccctgctgtg ctgcatcaag    1440
cccaccaggg ccgacgacac cctgcaggtg ctgaactacc tgtggaacaa caaccagaac    1500
ttcttctgga tgcagacact gatcccccctg gccgccctga tcgtgtgcat gcggatgctg    1560
cggtgcctgt tctgctgcgg ccctgccttc ctgctggtgt gcggagccct gggcgccgcc    1620
gcctacgagc acaccgccgt gatgcccaac aaagtgggca tcccctacaa ggccctggtg    1680
gaaaggcccg gctacgcccc cgtgcacctg cagatccagc tggtgaacac ccggatcatc    1740
cccagcacca atctggaata catcacctgc aagtacaaga ccaaggtgcc cagccccgtg    1800
gtgaagtgct gcgcgccac ccagtgcacc agcaagcccc accccgacta ccagtgccag    1860
gtgttcaccg gcgtgtaccc cttcatgtgg ggcggagcct actgcttctg cgacaccgag    1920
aacacccaga tgagcgaggc ctacgtggag cggagcgagg aatgcagcat cgaccacgcc    1980
aaggcctaca aggtgcacac cggcacagtg caggccatgg tgaacatcac ctacggcagc    2040
gtgagctggc ggagcgccga cgtgtacgtg aatggcgaga cccccgccaa gatcggcgac    2100
gccaagctga tcatcggccc cctgagcagc gcctggtccc ccttcgacaa caaagtggtg    2160
gtgtatggcc acgaggtgta caactacgac ttccccgagt acggcaccgg caaggccggc    2220
agcttcggcg acctgcagag ccggaccagc accagcaacg acctgtacgc caacaccaac    2280
ctgaagctgc agcggcccca ggccggcatc gtgcacaccc cttcacccca ggccccagc     2340 ggcttcgagc ggtggaagcg ggacaaaggc gcccctctga cgacgtggc ccccttcggc     2400 tgcagcatcg ccctggaacc cctgcgggcc gagaactgcg ccgtgggcag catccccatc    2460
agcatcgaca tccccgacgc cgccttcacc aggatctccg agaccccac cgtgagcgac    2520 ctggaatgca gatcaccga gtgcacctac gccagcgact cggcggcat cgccacagtg    2580 gcctacaagt ccagcaaggc cggaaactgc cccatccact cccctccgg cgtggccgtg    2640 atcaaagaaa cgacgtgac cctggccgag agcggcagct tcaccttcca cttcagcacc    2700
gccaacatcc accccgcctt caagctgcag gtgtgcacca gcgccgtgac ctgcaagggc    2760
```

-continued

```
gactgcaagc cccccaagga ccacatcgtg gactacccg cccagcacac cgagagcttc    2820
acctccgcca tcagcgccac cgcctggtcc tggctgaagg tgctggtcgg cggcacctcc    2880
gccttcatcg tgctgggcct gatcgccaca gccgtggtgg ccctggtgct gttcttccac    2940
cggcactgat ga                                                        2952
```

<210> SEQ ID NO 4
<211> LENGTH: 3732
<212> TYPE: DNA
<213> ORGANISM: Artificial Sequence
<220> FEATURE:
<223> OTHER INFORMATION: Based on equine encephalitis virus

<400> SEQUENCE: 4

```
atgttccctt accccaccct gaactacccc cccatggccc ccatcaaccc catggcctac      60
cgggacccta accctcccag acgccggtgg cggcccttca ccccctct ggccgcccag      120 atcgaggacc tgcggcggag cattgccagc ctgaccctga agcagagagc ccccaacct      180 cctgccggcc ctcccgccaa gcggaagaag cctgccccca gcccaagcc cgcccaggcc      240 aagaagaaga gccccctcc ccctgccaag aagcagaagc ggaagcctaa gcccggcaag      300
cggcagcgga tgtgcatgaa gctggaaagc gacaagacct tccccatcat gctgaacggc      360
caggtgaacg ctacgcctg cgtggtgggg ggcagagtgt tcaagcccct gcacgtggag      420
ggccggatcg acaacgagca gctggccgcc atcaagctga agaaggccag catctacgac      480
ctggaatacg cgacgtgcc ccagtgcatg aagtccgaca ccctgcagta caccagcgac      540 aagcccctg gcttctacaa ctggcaccac ggggccgtgc agtacgagaa caacagattc      600
accgtgccca gaggcgtggg cggcaagggc gacagcggca gacccatcct ggacaacaag      660
ggccgggtgg tggccatcgt gctgggcggc gtgaacgagg gcagccggac cgccctgagc      720
gtggtgacct ggaaccagaa aggcgtgacc gtgaaggaca ccccgagg cagcgagcct      780 tggagcctgg ccaccgtgat gtgcgtgctg gccaacatca ccttccctg cgaccagccc      840 ccctgcatgc cctgctgcta cgagaagaac cccacgaga ccctgaccat gctggaacag      900
aactacgaca gccgggccta cgaccagctg ctggacgccg ccgtgaagtg caacgccagg      960
cggaccaggc gggacctgga cacccacttc acccagtaca agctggccag gccctacatc     1020
gccgactgcc ccaactgcgg ccacagcaga tgcgacagcc ccatcgccat cgaggaagtg     1080
agaggcgacg cccatgctgg agtcatccgg atccagacca cgccatgtt cggcctgaaa     1140 accgacggcg tggacctggc ctacatgagc ttcatgaacg gcaagaccca aagagcatc     1200 aagatcgaca acctgcacgt gcggacctcc gccccctgca gcctggtgtc caccacggc     1260 tactacatcc tggcccagtg ccccctggc gacaccgtga ccgtgggctt ccacgacggc     1320
cccaaccggc acacctgcac cgtgccccac aaggtggagt ccggcccgt gggccgggag     1380 aagtaccggc acccccccga gcacggcgtg gagctgcct gcaaccggta cacccacaag     1440
cgggccgacc agggccacta cgtggagatg caccagcccg gcctggtggc cgaccacagc     1500
ctgctgtcca tccacagcgc caaggtgaaa atcaccgtgc cagcggagc ccaggtgaag     1560 tactactgca agtgccccga cgtgcgggag ggcatcacca gcagcgacca ccaccaccac     1620
tgtaccgacg tgaagcagtg cagggcctac ctgatcgaca acaagaaatg ggtgtacaac     1680
agcggcaggc tgcccagagg cgagggcgac accttcaagg gcaagctgca cgtgcccttc     1740
gtgcccgtga aggccaagtg catcgccacc ctggcccccg agcccctggt ggagcacaag     1800
```

```
caccggaccc tgatcctgca cctgcacccc gaccacccca ccctgctgac caccagaagc    1860
ctgggcagcg acgccaaccc cacccggcag tggatcgagc ggcccaccac cgtgaacttt    1920
accgtgaccg gcgagggcct ggaatacacc tggggcaacc accccccaa gagagtgtgg     1980 gcccaggaaa gcggcgaggg caaccctcac ggctggcccc acgaagtggt ggtctactac    2040
tacaacagat accccctgac caccatcatc ggcctgtgca cctgcgtggc catcatcatg    2100
gtgtcctgcg tgaccagcgt gtggctgctg tgccggaccc ggaacctgtg catcaccccc    2160
tataagctgg cccccaacgc ccaggtgccc atcctgctgg ccctgctgtg ctgcatcaag    2220
cccaccaggg ccgacgacac cctgcaggtg ctgaactacc tgtggaacaa caaccagaac    2280
ttcttctgga tgcagacact gatcccctg ccgccctga tcgtgtgcat gcggatgctg      2340
cggtgcctgt tctgctgcgg ccctgccttc ctgctggtgt gcggagccct gggcgccgcc    2400
gcctacgagc acaccgccgt gatgcccaac aaagtgggca tccccctacaa ggccctggtg   2460 gaaaggcccg gctacgcccc cgtgcacctg cagatccagc tggtgaacac ccggatcatc    2520
cccagcacca atctggaata catcacctgc aagtacaaga ccaaggtgcc cagccccgtg    2580
gtgaagtgct gcggcgccac ccagtgcacc agcaagcccc accccgacta ccagtgccag    2640
gtgttcaccg gcgtgtaccc cttcatgtgg ggcgagcct actgcttctg cgacaccgag     2700
aacacccaga tgagcgaggc ctacgtggag cggagcgagg aatgcagcat cgaccacgcc    2760
aaggcctaca aggtgcacac cggcacagtg caggccatgg tgaacatcac ctacggcagc    2820
gtgagctggc ggagcgccga cgtgtacgtg aatggcgaga ccccgccaa gatcggcgac    2880 gccaagctga tcatcggccc cctgagcagc gcctggtccc ccttcgacaa caaagtggtg   2940
gtgtatggcc acgaggtgta caactacgac ttccccgagt acggcaccgg caaggccggc   3000
agcttcggcg acctgcagag ccggaccagc accagcaacg acctgtacgc caacaccaac   3060
ctgaagctgc agcggcccca ggccggcatc gtgcacaccc ctttcaccca gccccccagc   3120
ggcttcgagc ggtggaagcg ggacaaaggc gcccctctga cgacgtggc cccttcggc     3180 tgcagcatcg ccctggaacc cctgcgggcc gagaactgcg ccgtgggcag catccccatc   3240
agcatcgaca tccccgacgc cgccttcacc aggatctccg agacccccac cgtgagcgac   3300
ctggaatgca aagatcaccga gtgcacctac gccagcgact tcggcggcat cgccacagtg   3360
gcctacaagt ccagcaaggc cggaaactgc cccatccact ccccctccgg cgtggccgtg   3420
atcaaagaaa acgacgtgac cctggccgag agcggcagct tcaccttcca cttcagcacc   3480
gccaacatcc accccgcctt caagctgcag gtgtgcacca cgccgtgac ctgcaagggc    3540 gactgcaagc ccccaaggga ccacatcgtg gactacccg cccagcacac cgagagcttc    3600
acctccgcca tcagcgccac cgcctggtcc tggctgaagg tgctggtcgg cggcacctcc   3660
gccttcatcg tgctgggcct gatcgccaca gccgtggtgg ccctggtgct gttcttccac   3720
cggcactgat ga                                                       3732
```

<210> SEQ ID NO 5
<211> LENGTH: 2940
<212> TYPE: DNA
<213> ORGANISM: Artificial Sequence
<220> FEATURE:
<223> OTHER INFORMATION: Based on equine encephalitis virus

<400> SEQUENCE: 5

```
atgagcctgg tgaccgccct gtgcgtgctg tccaacgtga ccttcccctg cgacaagccc      60
cccgtgtgct acagcctggc ccccgagcgg accctggacg tgctggaaga gaacgtggac     120
```

```
aaccccaact acgacaccct gctggaaaac gtgctgaagt gccccagcag gcggcccaag      180
cggagcatca ccgacgactt caccctgacc agccctacc tgggcttctg ccctactgc       240 cggcacagcg ccccctgctt cagccccatc aagatcgaga acgtgtggga cgagagcgac     300
gacggcagca tccggatcca ggtgtccgcc cagttcggct acaaccaggc cggcaccgcc     360
gacgtgacca agttccggta catgagctac gaccacgacc acgatatcaa ggaagatagc     420
atggaaaagc tggccatcag caccagcggc ccctgcagac ggctgggcca aagggctac     480 tttctgctgg cccagtgccc ccctggcgac agcgtgaccg tgagcatcac cagcggcgcc     540
agcgagaaca gctgcaccgt ggagaagaag atccggcgga agttcgtggg ccgggaggaa     600
tacctgttcc cccccgtgca cggcaagctg gtgaagtgcc acgtgtacga ccacctgaaa     660
gagaccagcg ccggctacat caccatgcac cggccaggcc cccacgccta caagagctac     720
ctggaagagg ccagcggcga ggtgtacatc aagccccca gcggcaagaa cgtgacctac      780
gagtgcaagt gcgcgactacagcaccggc atcgtgagca cccggaccaa gatgaacggc       840
tgcaccaagg ccaagcagtg catcgcctac aagcgggacc agaccaagtg ggtgttcaac     900
agccccgacc tgatccggca caccgaccac agcgtgcagg caaactgca catcccttc      960 cggctgaccc ccaccgtgtg ccccgtgccc ctggcccaca ccctaccgt gacaaagtgg      1020 ttcaagggca tcacactgca cctgaccgcc accggccca ccctgctgac cacccggaag      1080
ctgggcctga gggccgatgc caccgccgag tggatcaccg gcaccacctc ccggaacttc     1140
agcgtgggca gagagggcct ggaatacgtc tggggcaacc acgagcccgt gagagtgtgg     1200
gcccaggaaa gcgccccagg cgaccccac ggctggcccc acgagatcat catccactac      1260
taccaccggc accccgtgta ccgtgatcg tgctgtgcg gcgtggccct ggccatcctg       1320
gtgggcaccg ccagcagcgc cgcctgcatc gccaaggcca ggcgggactg cctgaccccc    1380
tacgccctgg cccccaacgc caccgtgcca accgccctgg ccgtgctgtg ctgcatccgg     1440
cccaccaacg ccgagaccct cggcgagacc ctgaaccacc tgtggttcaa caaccagccc    1500
ttcctgtggg cccagctgtg catcccctg gccgccctga tcatcctgtt ccggtgcttc     1560
agctgctgca tgccttttct gctggtcgcc ggcgtgtgcc tgggcaaggt ggacgccttc    1620
gagcacgcca ccaccgtgcc caacgtgccc ggcatcccct acaaggccct ggtggagagg    1680
gccggctacg ccccccctgaa cctggaaatc accgtggtgt ccagcgagct gacccctcc    1740 accaacaaag aatacgtgac ctgcaagttc cacaccgtgg tgccctcccc ccaggtgaag    1800
tgctgcggca gcctggaatg caaggccagc agcaaggccg actacacctg ccgggtgttc    1860
ggcggcgtgt accccttcat gtggggcgga gcacagtgct ctgcgactc cgagaacacc    1920 cagctgtccg aggcctacgt ggagttcgcc cccgactgca ccatcgacca cgccgtggcc    1980
ctgaaggtgc acacagccgc cctgaaagtg ggcctgcgga tcgtgtacgg caacaccacc    2040
gccaggctgg acaccttcgt gaacggcgtg accccggca gccgggga cctgaaggtg       2100 atcgccggac ccatctccgc cgccttcagc cccttcgacc acaaggtggt gatccggaag    2160
ggcctggtgt acaactacga cttccccgag tacggcgcca tgaaccctgg cgccttcggc    2220
gacatccagg ccagctccct ggacgccacc gacatcgtgg cccggaccga catccggctg    2280
ctgaagccca gcgtgaagaa catccacgtg ccctacaccc aggccgtgag cggctacgag    2340
atgtggaaga caacagcgg cagacccctg caggaaaccg ccccctcgg ctgcaagatc      2400 gaggtggagc ccctgcgggc caccaactgc gcctacggcc acatccccat cagcatcgac    2460
```

| | |
|---|---|
| atccccgacg ccgccttcgt gcggagcagc gagagcccca ccatcctgga agtgagctgt | 2520 |
| accgtggccg actgcatcta cagcgccgac ttcggcggct ccctgaccct gcagtacaag | 2580 |
| gccaaccggg agggccactg ccccgtgcac agccacagca ccaccgccgt gctgaaagag | 2640 |
| gccaccaccc acgtcaccgc cacaggcagc atcaccctgc acttcagcac cagctccccc | 2700 |
| caggccaact tcatcgtgag cctgtgcggc aagaaaacca cctgcaacgc cgagtgcaag | 2760 |
| cccccctgccg accacatcat cggcgagcct cacaaggtgg accaggaatt ccaggccgcc | 2820 |
| gtcagcaaga ccagctggaa ctggctgctg gccctgttcg gcggagccag cagcctgatc | 2880 |
| gtggtgggcc tgattgtgct ggtgtgcagc agcatgctga tcaacacccg gcggtgatga | 2940 |

<210> SEQ ID NO 6
<211> LENGTH: 3714
<212> TYPE: DNA
<213> ORGANISM: Artificial Sequence
<220> FEATURE:
<223> OTHER INFORMATION: Based on equine encephalitis virus

<400> SEQUENCE: 6

| | |
|---|---|
| atgttcccct accccagct gaacttcccc ccgtgtacc ccaccaaccc catggcctac | 60 |
| cgggacccta tccacctag acgccggtgg cggcccttca ccccctct ggccgcccag | 120 |
| atcgaggacc tgcggcggag cattgccaac ctgaccttca gcagagagc ccccaaccct | 180 |
| cctccaggac cccctcccaa gaagaagaag tccgccccca gcccaagcc cacccagcct | 240 |
| aagaagaaaa agcagcaggc caagaaaacc aagcggaagc ctaagcccgg caagcggcag | 300 |
| cggatgtgca tgaagctgga aagcgacaag accttcccca tcatgctgaa cggccaggtg | 360 |
| aacggctacg cctgcgtggt gggcgggaga ctgatgaagc ccctgcacgt ggagggcaag | 420 |
| atcgacaacg agcagctggc cgccgtgaag ctgaagaaag ccagcatgta cgacctggaa | 480 |
| tacggcgacg tgccccagaa catgaagtcc gacacccttgc agtacaccag cgacaagccc | 540 |
| cctggcttct acaactggca ccatggcgcc gtgcagtacg agaacggccg gttcaccgtg | 600 |
| cccagaggcg tgggcggcaa gggcgacagc ggcagaccca tcctggacaa ccggggcaga | 660 |
| gtggtggcca tcgtgctggg cggagccaac gagggcaccc ggacagccct gagcgtggtg | 720 |
| acctggaacc agaaaggcgt gaccatcaag gacacccccg agggcagcga gccctggagc | 780 |
| ctggtgaccg ccctgtgcgt gctgtccaac gtgaccttcc cctgcgacaa gccccccgtg | 840 |
| tgctacagcc tggcccccga gcggaccctg gacgtgctgg aagagaacgt ggacaaccce | 900 |
| aactacgaca ccctgctgga aaacgtgctg aagtgcccca gcaggcggcc caagcggagc | 960 |
| atcaccgacg acttcacccct gaccagcccc tacctgggct ctgcccccta ctgccggcac | 1020 |
| agcgccccct gcttcagccc catcaagatc gagaacgtgt gggacgagag cgacgacggc | 1080 |
| agcatccgga tccaggtgtc cgcccagttc ggctacaacc aggccggcac cgccgacgtg | 1140 |
| accaagttcc ggtacatgag ctacgaccac gaccacgata tcaaggaaga tagcatggaa | 1200 |
| aagctggcca tcagcaccag cggcccctgc agacggctgg ccacaaggg ctactttctg | 1260 |
| ctggcccagt gccccccggg cgacagcgtg accgtgagca tcaccagcgg cgccagcgag | 1320 |
| aacagctgca ccgtggagaa gaagatccgg cggaagttcg tgggccggga ggaatacctg | 1380 |
| ttccccccg tgcacggcaa gctggtgaag tgccacgtgt acgaccacct gaaagagacc | 1440 |
| agcgccggct acatcaccat gcaccggcca ggccccacg cctacaagag ctacctggaa | 1500 |
| gaggccagcg cgaggtgta catcaagccc cccagcggca gaacgtgac ctacgagtgc | 1560 |
| aagtgcggcg actacagcac cggcatcgtg agcacccgga ccaagatgaa cggctgcacc | 1620 |

```
aaggccaagc agtgcatcgc ctacaagcgg gaccagacca agtgggtgtt caacagcccc    1680
gacctgatcc ggcacaccga ccacagcgtg cagggcaaac tgcacatccc cttccggctg    1740
acccccaccg tgtgccccgt gcccctggcc cacacccta ccgtgacaaa gtggttcaag     1800
ggcatcacac tgcacctgac cgccacccgg cccaccctgc tgaccacccg gaagctgggc    1860
ctgagggccg atgccaccgc cgagtggatc accggcacca cctcccggaa cttcagcgtg    1920
ggcagagagg gcctggaata cgtctggggc aaccacgagc ccgtgagagt gtgggcccag    1980
gaaagcgccc caggcgaccc ccacggctgg ccccacgaga tcatcatcca ctactaccac    2040
cggcaccccg tgtacaccgt gatcgtgctg tgcggcgtgg ccctggccat cctggtgggc    2100
accgccagca gcgccgcctg catcgccaag gccaggcggg actgcctgac cccctacgcc    2160
ctggcccca cgccaccgt gccaaccgcc tggccgtgc tgtgctgcat ccggcccacc       2220
aacgccgaga ccttcggcga ccctgaac cacctgtggt tcaacaacca gcccttcctg      2280
tgggcccagc tgtgcatccc cctggccgcc ctgatcatcc tgttccggtg cttcagctgc    2340
tgcatgcctt ttctgctggt cgccggcgtg tgcctgggca aggtggacgc cttcgagcac    2400
gccaccaccg tgcccaacgt gcccggcatc ccctacaagg ccctggtgga gagggccggc    2460
tacgccccc tgaacctgga aatcaccgtg gtgtccagcg agctgacccc ctccaccaac     2520
aaagaatacg tgacctgcaa gttccacacc gtggtgccct cccccaggt gaagtgctgc    2580
ggcagcctgg aatgcaaggc cagcagcaag gccgactaca cctgccgggt gttcggcggc    2640
gtgtaccct tcatgtgggg cggagcacag tgcttctgcg actccgagaa cacccagctg    2700
tccgaggcct acgtggagtt cgcccccgac tgcaccatcg accacgccgt ggccctgaag   2760
gtgcacacag ccgccctgaa agtgggcctg cggatcgtgt acggcaacac caccgccagg    2820
ctggacacct tcgtgaacgg cgtgacccc ggcagcagcg ggaccctgaa ggtgatcgcc     2880
ggacccatct ccgccgcctt cagccccttc gaccacaagg tggtgatccg gaagggcctg    2940
gtgtacaact acgacttccc cgagtacggc gccatgaacc ctggcgcctt cggcgacatc    3000
caggccagct ccctggacgc caccgacatc gtggcccgga ccgacatccg gctgctgaag    3060
cccagcgtga agaacatcca cgtgccctac acccaggccg tgagcggcta cgagatgtgg    3120
aagaacaaca gcggcagacc cctgcaggaa accgccccct tcggctgcaa gatcgaggtg    3180
gagcccctgc gggccaccaa ctgcgcctac ggccacatcc ccatcagcat cgacatcccc    3240
gacgccgcct tcgtgcggag cagcgagagc cccaccatcc tggaagtgag ctgtaccgtg    3300
gccgactgca tctacagcgc cgacttcggc ggctccctga cctgcagta caaggccaac    3360
cgggagggcc actgccccgt gcacagccac agcaccaccg ccgtgctgaa agaggccacc    3420
acccacgtca ccgccacagg cagcatcacc ctgcacttca gcaccagctc ccccaggcc    3480
aacttcatcg tgagcctgtg cggcaagaaa accacctgca acgccgagtg caagccccct    3540
gccgaccaca tcatcggcga gcctcacaag gtggaccagg aattccaggc cgccgtcagc    3600
aagaccagct ggaactggct gctggccctg ttcggcggag ccagcagcct gatcgtggtg    3660
ggcctgattg tgctggtgtg cagcagcatg ctgatcaaca cccggcggtg atga         3714
```

<210> SEQ ID NO 7
<211> LENGTH: 7179
<212> TYPE: DNA
<213> ORGANISM: Artificial Sequence
<220> FEATURE:
<223> OTHER INFORMATION: Based on equine encephalitis virus

<400> SEQUENCE: 7

```
gggggggggg ggcgctgagg tctgcctcgt gaagaaggtg ttgctgactc ataccaggcc      60
tgaatcgccc catcatccag ccagaaagtg agggagccac ggttgatgag agctttgttg     120
taggtggacc agttggtgat tttgaacttt gctttgcca cggaacggtc tgcgttgtcg     180
ggaagatgcg tgatctgatc cttcaactca gcaaaagttc gatttattca acaaagccgc     240
cgtcccgtca agtcagcgta atgctctgcc agtgttacaa ccaattaacc aattctgatt     300
agaaaaactc atcgagcatc aaatgaaact gcaatttatt catatcagga ttatcaatac     360
catattttg aaaaagccgt ttctgtaatg aaggagaaaa ctcaccgagg cagttccata     420
ggatggcaag atcctggtat cggtctgcga ttccgactcg tccaacatca atacaaccta     480
ttaatttccc ctcgtcaaaa ataaggttat caagtgagaa atcaccatga gtgacgactg     540
aatccggtga gaatggcaaa agcttatgca tttctttcca gacttgttca acaggccagc     600
cattacgctc gtcatcaaaa tcactcgcat caaccaaacc gttattcatt cgtgattgcg     660
cctgagcgag acgaaatacg cgatcgctgt taaaaggaca attacaaaca ggaatcgaat     720
gcaaccggcg caggaacact gccagcgcat caacaatatt ttcacctgaa tcaggatatt     780
cttctaatac ctggaatgct gttttcccgg ggatcgcagt ggtgagtaac catgcatcat     840
caggagtacg gataaaatgc ttgatggtcg gaagaggcat aaattccgtc agccagttta     900
gtctgaccat ctcatctgta acatcattgg caacgctacc tttgccatgt ttcagaaaca     960
actctggcgc atcgggcttc ccatacaatc gatagattgt cgcacctgat tgcccgacat    1020
tatcgcgagc ccatttatac ccatataaat cagcatccat gttggaattt aatcgcggcc    1080
tcgagcaaga cgtttcccgt tgaatatggc tcataacacc ccttgtatta ctgtttatgt    1140
aagcagacag ttttattgtt catgatgata tatttttatc ttgtgcaatg taacatcaga    1200
gattttgaga cacaacgtgg ctttcccccc cccccggca tgcctgcagg tcgacataaa    1260
tcaatattgg ctattggcca ttgcatacgt tgtatctata tcataatatg tacatttata    1320
ttggctcatg tccaatatga ccgccatgtt gacattgatt attgactagt tattaatagt    1380
aatcaattac gggtcatta gttcatagcc catatatgga gttccgcgtt acataactta    1440
cggtaaatgg cccgcctcgt gaccgcccaa cgaccccgc ccattgacgt caataatgac    1500
gtatgttccc atagtaacgc caatagggac tttccattga cgtcaatggg tggagtattt    1560
acggtaaact gcccacttgg cagtacatca agtgtatcat atgccaagtc cggcccccta    1620
ttgacgtcaa tgacggtaaa tggcccgcct ggcattatgc ccagtacatg accttacggg    1680
actttcctac ttggcagtac atctacgtat tagtcatcgc tattaccatg gtgatgcggt    1740
tttggcagta caccaatggg cgtggatagc ggtttgactc acgggatttt ccaagtctcc    1800
accccattga cgtcaatggg agtttgtttt ggcaccaaaa tcaacgggac tttccaaaat    1860
gtcgtaataa ccccgcccg ttgacgcaaa tgggcggtag cgtgtacgg tgggaggtct    1920
atataagcag agctcgttta gtgaaccgtc agatcgcctg gagacgccat ccacgctgtt    1980
ttgacctcca tagaagacac cgggaccgat ccagcctccg cggccgggaa cggtgcattg    2040
gaacgcggat tccccgtgcc aagagtgacg taagtaccgc ctatagactc tataggcaca    2100
cccctttggc tcttatgcat gctatactgt ttttggcttg gggcctatac accccgctc    2160
cttatgctat aggtgatggt atagcttagc ctataggtgt gggttattga ccattattga    2220
ccactcccct attggtgacg atactttcca ttactaatcc ataacatggc tctttgccac    2280
aactatctct attggctata tgccaatact ctgtccttca gagactgaca cggactctgt    2340
```

```
atttttacag gatggggtcc catttattat ttacaaattc acatatacaa caacgccgtc   2400 cccgtgccc gcagttttta ttaaacatag cgtgggatct ccacgcgaat ctcgggtacg    2460
tgttccggac atgggctctt ctccggtagc ggcggagctt ccacatccga gccctggtcc   2520
catgcctcca gcggctcatg gtcgctcggc agctccttgc tcctaacagt ggaggccaga   2580
cttaggcaca gcacaatgcc caccaccacc agtgtgccgc acaaggccgt ggcggtaggg   2640
tatgtgtctg aaaatgagct cggagattgg gctcgcaccg tgacgcagat ggaagactta   2700
aggcagcggc agaagaagat gcaggcagct gagttgttgt attctgataa gagtcagagg   2760
taactcccgt tgcggtgctg ttaacggtgg agggcagtgt agtctgagca gtactcgttg   2820
ctgccgcgcg cgccaccaga cataatagct gacagactaa cagactgttc ctttccatgg   2880
gtcttttctg cagtcaccgt ccaagcttgc ggccgcgcca ccatgagcct ggtgaccacc   2940
atgtgcctgc tggccaacgt gaccttcccc tgcgcccagc cccccatctg ctacgaccgg   3000
aagcccgccg agaccctggc catgctgtcc gtgaacgtgg acaacccecgg ctacgacgag   3060 ctgctggaag ccgccgtgaa gtgccccggc aggaagcggc ggagcaccga ggaactgttc   3120
aaagagtaca agctgacccg gccctacatg gcccggtgca tcagatgcgc cgtgggcagc   3180
tgccacagcc ccatcgccat cgaggccgtg aagagcgacg ccacgacgg ctacgtgcgg   3240 ctgcagacca gcagccagta cggcctggac agcagcggca acctgaaggg ccggaccatg   3300
agatacgaca tgcacggcac catcaaagag atcccctgc accaggtgtc cctgcacacc   3360
agccggccct gccacatcgt ggacggccac ggctactttc tgctggccag gtgccctgcc   3420
ggcgacagca tcaccatgga attcaagaaa gacagcgtga cccacagctg cagcgtgccc   3480
tacgaggtga agttcaaccc cgtgggccgg gagctgtaca cccacccecc cgagcacggc   3540 gtggagcagg cctgccaggt gtacgcccac gacgcccaga cagggggcgc ctacgtggag   3600
atgcacctgc ccggcagcga ggtggacagc tccctggtgt ccctgagcgg cagcagcgtg   3660
accgtgaccc cccctgtggg caccagcgcc ctggtggagt gcgagtgcgg cggcaccaag   3720
atcagcgaga ccatcaacaa gaccaagcag ttcagccagt gcaccaagaa agagcagtgc   3780
cgggcctacc ggctgcagaa cgacaagtgg gtgtacaaca cgacaagct gcccaaagcc   3840 gccggagcca ccctgaaggg caagctgcac gtgccttttc tgctggctga cggcaagtgc   3900 accgtgccc tggcccccga gcccatgatc accttcggct tcagaagcgt gagcctgaag   3960
ctgcacccca gaaccccac ctacctgacc acccggcagc tggccgatga gccccactac   4020
acccacgagc tgatcagcga gccgccgtg cggaacttca ccgtgaccga aagggctgg   4080 gagttcgtgt ggggcaacca ccccccaag aggttctggg ctcaggaaac agcccctggc   4140 aaccccacg gcctgcctca cgaggtgatc acccactact accacagata ccccatgagc   4200
accatcctgg gctgagcat ctgcgccgcc atcgccaccg tgagcgtggc cgccagcacc   4260
tggctgttct gccggtcccg ggtggcctgc ctgaccccct acaggctgac ccccaacgcc   4320 cggatccect tctgcctggc cgtgctgtgc tgcgcccgga ccgccagagc cgagaccacc   4380
tgggagagcc tggaccacct gtggaacaac aaccagcaga tgttctggat ccagctgctg   4440 atcccctgg ccgccctgat cgtggtgacc cggctgctga gatgcgtgtg ctgcgtggtg   4500
cccttcctgg tgatggccgg ggctgcaggg gccggcgcct atgagcacgc caccaccatg   4560
cccagccagg ccggcatcag ctacaacacc atcgtgaaca gggccggcta cgcccccctg   4620
cccatcagca tcaccccctac caagatcaag ctgatcccca ccgtgaacct ggaatacgtg   4680
```

```
acctgccact acaagaccgg catggacagc ccgccatca agtgctgcgg cagccaggaa    4740
tgcaccccca cctacaggcc cgacgagcag tgcaaggtgt tcaccggcgt gtacccttc    4800
atgtggggcg agcctactg cttctgcgac accgagaaca cccaggtgtc caaggcctac    4860
gtgatgaagt ccgacgattg cctggccgac acgccgagg cctacaaggc ccacaccgcc    4920
agcgtgcagg ccttcctgaa catcaccgtg gcgagcaca gcatcgtgac caccgtgtac    4980
gtgaacggcg agacccccgt gaacttcaac ggcgtgaagc tgaccgccgg accccctgagc   5040
accgctgga ccccttcga ccggaagatc gtgcagtacg ccggcgaaat ctacaactac    5100
gacttccccg agtatggcgc cggacagcct ggcgccttcg cgacatcca gagccggacc    5160
gtgagcagca gcgacctgta cgccaacacc aacctggtgc tgcagcggcc caaggccgga    5220
gccatccacg tgccctacac ccaggccccc agcggcttcg agcagtggaa gaaggacaag    5280
gccccctccc tgaagttcac cgcccccttc ggctgtgaaa tctacaccaa ccccatccgg    5340
gccgagaact gtgccgtggg ctccatccct ctggccttcg acatccccga cgccctgttc    5400
accagagtgt ccgagacccc cacccctgtct gccgccgagt gcaccctgaa cgagtgcgtc    5460
tactcctctg acttcggcgg catcgccaca gtgaagtaca gcgccagcaa gagcggcaag    5520
tgtgccgtgc acgtgcccag cggcacagcc acactgaagg aagccgccgt ggagctgacc    5580
gagcagggca gcgccaccat ccacttcagc accgccaaca tccaccccga gttcaggctg    5640
cagatttgca ccagctacgt gacatgcaag ggcgactgcc accccctaa ggaccacatc    5700
gtgacccacc cccagtacca cgcccagacc ttcacagccg ccgtgtccaa gacagcctgg    5760
acctggctga ccagctgct gggcggcagc gccgtgatca tcatcatcgg cctggtgctg    5820
gccaccatcg tggccatgta cgtgctgacc aaccagaaac acaactgatg aagatctacg    5880
tatgatcagc ctcgactgtg ccttctagtt gccagccatc tgttgtttgc cctccccccg    5940
tgccttcctt gaccctggaa ggtgccactc ccactgtcct ttcctaataa aatgaggaaa    6000
ttgcatcgca ttgtctgagt aggtgtcatt ctattctggg gggtggggtg gggcaggaca    6060
gcaaggggga ggattgggaa gacaatagca ggcatgctgg ggatgcggtg ggctctatgg    6120
cttctgaggc ggaaagaacc agctggggct cgacagctcg actctagaat tgcttcctcg    6180
ctcactgact cgctgcgctc ggtcgttcgg ctgcggcgag cggtatcagc tcactcaaag    6240
gcggtaatac ggttatccac agaatcaggg gataacgcag gaaagaacat gtgagcaaaa    6300
ggccagcaaa aggccaggaa ccgtaaaaag gccgcgttgc tggcgttttt ccataggctc    6360
cgcccccctg acgagcatca aaaaatcga cgctcaagtc agaggtggcg aaacccgaca    6420
ggactataaa gataccaggc gtttcccct ggaagctccc tcgtgcgctc tcctgttccg    6480
accctgccgc ttaccggata cctgtccgcc tttctccctt cgggaagcgt ggcgctttct    6540
caatgctcac gctgtaggta tctcagttcg gtgtaggtcg ttcgctccaa gctgggctgt    6600
gtgcacgaac cccccgttca gcccgaccgc tgcgccttat ccggtaacta tcgtcttgag    6660
tccaacccgg taagacacga cttatcgcca ctggcagcag ccactggtaa caggattagc    6720
agagcgaggt atgtaggcgg tgctacagag ttcttgaagt ggtggcctaa ctacggctac    6780
actagaagga cagtatttgg tatctgcgct ctgctgaagc cagttacctt cggaaaaaga    6840
gttggtagct cttgatccgg caaacaaacc accgctggta gcggtggttt ttttgtttgc    6900
aagcagcaga ttacgcgcag aaaaaaagga tctcaagaag atcctttgat cttttctacg    6960
gggtctgacg ctcagtggaa cgaaaactca cgttaaggga ttttggtcat gagattatca    7020
aaaggatct tcacctagat ccttttaaat taaaaatgaa gttttaaatc aatctaaagt    7080
```

-continued

| | |
|---|---|
| atatatgagt aaacttggtc tgacagttac caatgcttaa tcagtgaggc acctatctca | 7140 |
| gcgatctgtc tatttcgttc atccatagtt gcctgactc | 7179 |

<210> SEQ ID NO 8
<211> LENGTH: 7182
<212> TYPE: DNA
<213> ORGANISM: Artificial Sequence
<220> FEATURE:
<223> OTHER INFORMATION: Based on equine encephalitis virus

<400> SEQUENCE: 8

| | |
|---|---|
| ggggggggggg ggcgctgagg tctgcctcgt gaagaaggtg ttgctgactc ataccaggcc | 60 |
| tgaatcgccc catcatccag ccagaaagtg agggagccac ggttgatgag agctttgttg | 120 |
| taggtggacc agttggtgat tttgaacttt tgctttgcca cggaacggtc tgcgttgtcg | 180 |
| ggaagatgcg tgatctgatc cttcaactca gcaaaagttc gatttattca acaaagccgc | 240 |
| cgtcccgtca agtcagcgta atgctctgcc agtgttacaa ccaattaacc aattctgatt | 300 |
| agaaaaactc atcgagcatc aaatgaaact gcaatttatt catatcagga ttatcaatac | 360 |
| catattttg aaaaagccgt ttctgtaatg aaggagaaaa ctcaccgagg cagttccata | 420 |
| ggatggcaag atcctggtat cggtctgcga ttccgactcg tccaacatca atacaaccta | 480 |
| ttaatttccc ctcgtcaaaa ataaggttat caagtgagaa atcaccatga gtgacgactg | 540 |
| aatccggtga gaatggcaaa agcttatgca tttctttcca gacttgttca acaggccagc | 600 |
| cattacgctc gtcatcaaaa tcactcgcat caaccaaacc gttattcatt cgtgattgcg | 660 |
| cctgagcgag acgaaatacg cgatcgctgt taaaaggaca attacaaaca ggaatcgaat | 720 |
| gcaaccggcg caggaacact gccagcgcat caacaatatt ttcacctgaa tcaggatatt | 780 |
| cttctaatac ctggaatgct gttttcccgg ggatcgcagt ggtgagtaac catgcatcat | 840 |
| caggagtacg gataaaatgc ttgatggtcg gaagaggcat aaattccgtc agccagttta | 900 |
| gtctgaccat ctcatctgta acatcattgg caacgctacc tttgccatgt ttcagaaaca | 960 |
| actctggcgc atcgggcttc ccatacaatc gatagattgt cgcacctgat tgcccgacat | 1020 |
| tatcgcgagc ccatttatac ccatataaat cagcatccat gttggaattt aatcgcggcc | 1080 |
| tcgagcaaga cgtttcccgt tgaatatggc tcataacacc ccttgtatta ctgtttatgt | 1140 |
| aagcagacag ttttattgtt catgatgata tattttatc ttgtgcaatg taacatcaga | 1200 |
| gattttgaga cacaacgtgg ctttccccccc ccccccggca tgcctgcagg tcgacataaa | 1260 |
| tcaatattgg ctattggcca ttgcatacgt tgtatctata tcataatatg tacatttata | 1320 |
| ttggctcatg tccaatatga ccgccatgtt gacattgatt attgactagt tattaatagt | 1380 |
| aatcaattac gggtcatta gttcatagcc catatatgga gttccgcgtt acataactta | 1440 |
| cggtaaatgg cccgcctcgt gaccgcccaa cgacccccgc ccattgacgt caataatgac | 1500 |
| gtatgttccc atagtaacgc caatagggac tttccattga cgtcaatggg tggagtattt | 1560 |
| acggtaaact gcccacttgg cagtacatca agtgtatcat atgccaagtc cggcccccta | 1620 |
| ttgacgtcaa tgacggtaaa tggcccgcct ggcattatgc ccagtacatg accttacggg | 1680 |
| actttcctac ttggcagtac atctacgtat tagtcatcgc tattaccatg gtgatgcggt | 1740 |
| tttggcagta caccaatggg cgtggatagc ggtttgactc acggggattt ccaagtctcc | 1800 |
| accccattga cgtcaatggg agtttgtttt ggcaccaaaa tcaacgggac tttccaaaat | 1860 |
| gtcgtaataa ccccgccccg ttgacgcaaa tgggcggtag gcgtgtacgg tgggaggtct | 1920 |

-continued

```
atataagcag agctcgttta gtgaaccgtc agatcgcctg gagacgccat ccacgctgtt    1980
ttgacctcca tagaagacac cgggaccgat ccagcctccg cggccgggaa cggtgcattg    2040
gaacgcggat tccccgtgcc aagagtgacg taagtaccgc ctatagactc tataggcaca    2100
ccccttggc tcttatgcat gctatactgt ttttggcttg gggcctatac accccgctc     2160
cttatgctat aggtgatggt atagcttagc ctataggtgt gggttattga ccattattga    2220
ccactcccct attggtgacg atactttcca ttactaatcc ataacatggc tctttgccac    2280
aactatctct attggctata tgccaatact ctgtccttca gagactgaca cggactctgt    2340
atttttacag gatggggtcc catttattat ttacaaattc acatatacaa caacgccgtc    2400
ccccgtgccc gcagttttta ttaaacatag cgtgggatct ccacgcgaat ctcgggtacg    2460
tgttccggac atgggctctt ctccggtagc ggcggagctt ccatatccga gccctggtcc    2520
catgcctcca gcggctcatg gtcgctcggc agctccttgc tcctaacagt ggaggccaga    2580
cttaggcaca gcacaatgcc caccaccacc agtgtgccgc acaaggccgt ggcggtaggg    2640
tatgtgtctg aaaatgagct cggagattgg gctcgcaccg tgacgcagat ggaagactta    2700
aggcagcggc agaagaagat gcaggcagct gagttgttgt attctgataa gagtcagagg    2760
taactcccgt tgcggtgctg ttaacggtgg agggcagtgt agtctgagca gtactcgttg    2820
ctgccgcgcg cgccaccaga cataatagct gacagactaa cagactgttc ctttccatgg    2880
gtcttttctg cagtcaccgt ccaagcttgc ggccgcgcca ccatgagcct ggccaccgtg    2940
atgtgcgtgc tggccaacat caccttccct tgcgaccagc cccctgcat gccctgctgc    3000
tacgagaaga ccccccacga gaccctgacc atgctggaac agaactacga cagccgggcc    3060
tacgaccagc tgctggacgc cgccgtgaag tgcaacgcca ggcggaccag cgggacctg    3120
gacacccact tcacccagta caagctggcc aggccctaca tcgccgactg ccccaactgc    3180
ggccacagca gatgcgacag ccccatcgcc atcgaggaag tgagaggcga cgcccatgct    3240
ggagtcatcc ggatccagac cagcgccatg ttcggcctga aaaccgacgg cgtggacctg    3300
gcctacatga gcttcatgaa cggcaagacc cagaagagca tcaagatcga caacctgcac    3360
gtgcggacct ccgccccctg cagcctggtg tcccaccacg gctactacat cctggcccag    3420
tgccccctg gcgacaccgt gaccgtgggc ttccacgacg gccccaaccg gcacacctgc    3480
accgtggccc acaaggtgga gttccggccc gtgggccggg agaagtaccg gcaccccccc    3540
gagcacggcg tggagctgcc ctgcaaccgg tacacccaca gcgggccgga ccagggccac    3600
tacgtggaga tgcaccagcc cggcctggtg gccgaccaca gctgctgtc catccacagc    3660
gccaaggtga aaatcaccgt gcccagcgga gcccaggtga agtactactg caagtgcccc    3720
gacgtgcggg agggcatcac cagcagcgac cacaccacca cctgtaccga cgtgaagcag    3780
tgcagggcct acctgatcga caacaagaaa tgggtgtaca cagcggcag gctgcccaga    3840
ggcgagggcg acaccttcaa gggcaagctg cacgtgccct tcgtgcccgt gaaggccaag    3900
tgcatcgcca cctggccccc cgagcccctg gtggagcaca agcaccggac cctgatcctg    3960
cacctgcacc ccgaccaccc caccctgctg accaccagaa gcctgggcag cgacgccaac    4020
cccaccggc agtggatcga gcggcccacc accgtgaact taccgtgac cggcgagggc    4080
ctggaataca cctggggcaa ccaccccccc aagagagtgt gggcccagga aagcggcgag    4140
ggcaaccctc acggctggcc ccacgaagtg gtggtctact actacaacag ataccccctg    4200
accaccatca tcggcctgtg cacctgcgtg gccatcatca tggtgtcctg cgtgaccagc    4260
gtgtggctgc tgtgccggac ccggaacctg tgcatcaccc cctataagct ggcccccaac    4320
```

```
gcccaggtgc ccatcctgct ggccctgctg tgctgcatca agcccaccag ggccgacgac    4380
accctgcagg tgctgaacta cctgtggaac aacaaccaga acttcttctg gatgcagaca    4440
ctgatccccc tggccgccct gatcgtgtgc atgcggatgc tgcggtgcct gttctgctgc    4500
ggccctgcct tcctgctggt gtgcggagcc ctgggcgccg ccgcctacga gcacaccgcc    4560
gtgatgccca acaaagtggg catcccctac aaggccctgg tggaaaggcc cggctacgcc    4620
cccgtgcacc tgcagatcca gctggtgaac accggatca tccccagcac caatctggaa    4680
tacatcacct gcaagtacaa gaccaaggtg cccagccccg tggtgaagtg ctgcggcgcc    4740
acccagtgca ccagcaagcc ccaccccgac taccagtgcc aggtgttcac cggcgtgtac    4800
cccttcatgt ggggcggagc ctactgcttc tgcgacaccg agaacaccca gatgagcgag    4860
gcctacgtgg agcggagcga ggaatgcagc atcgaccacg ccaaggccta caaggtgcac    4920
accggcacag tgcaggccat ggtgaacatc acctacggca gcgtgagctg cggagcgcc    4980 gacgtgtacg tgaatggcga gaccccgcc aagatcggcg acgccaagct gatcatcggc    5040
cccctgagca gcgcctggtc cccttcgac aacaaagtgg tggtgtatgg ccacgaggtg    5100
tacaactacg acttccccga gtacggcacc ggcaaggccg gcagcttcgg cgacctgcag    5160
agccggacca gcaccagcaa cgacctgtac gccaacacca cctgaagct gcagcggccc    5220 caggccggca tcgtgcacac ccctttcacc caggccccca gcggcttcga gcggtggaag    5280
cgggacaaag gcgcccctct gaacgacgtg gccccttcg gctgcagcat cgccctggaa    5340
cccctgcggg ccgagaactg cgccgtgggc agcatcccca tcagcatcga catccccgac    5400
gccgccttca ccaggatctc cgagaccccc accgtgagcg acctggaatg caagatcacc    5460
gagtgcacct acgccagcga cttcggcggc atcgccacag tggcctacaa gtccagcaag    5520
gccggaaact gccccatcca ctcccctcc ggcgtggccg tgatcaaaga aaacgacgtg    5580
accctggccg agagcggcag cttcaccttc cacttcagca ccgccaacat ccaccccgcc    5640
ttcaagctgc aggtgtgcac cagcgccgtg acctgcaagg gcgactgcaa gccccccaag    5700
gaccacatcg tggactaccc cgcccagcac accgagagct tcacctccgc catcagcgcc    5760
accgcctggt cctggctgaa ggtgctggtc ggcggcacct ccgccttcat cgtgctgggc    5820
ctgatcgcca cagccgtggt ggccctggtg ctgttcttcc accggcactg atgaagatct    5880
acgtatgatc agcctcgact gtgccttcta gttgccagca atctgttgtt tgcccctccc    5940
ccgtgccttc cttgaccctg gaaggtgcca ctcccactgt cctttcctaa taaaatgagg    6000
aaattgcatc gcattgtctg agtaggtgtc attctattct gggggtggg gtggggcagg    6060 acagcaaggg ggaggattgg gaagacaata gcaggcatgc tggggatgcg gtgggctcta    6120
tggcttctga gcggaaaga accagctggg gctcgacagc tcgactctag aattgcttcc    6180
tcgctcactg actcgctgcg ctcggtcgtt cggctgcggc gagcggtatc agctcactca    6240
aaggcggtaa tacggttatc cacagaatca ggggataacg caggaaagaa catgtgagca    6300
aaaggccagc aaaaggccag gaaccgtaaa aaggccgcgt tgctggcgtt tttccatagg    6360 ctccgcccc ctgacgagca tcacaaaaat cgacgctcaa gtcagaggtg gcgaaacccg    6420
acaggactat aaagatacca ggcgtttccc cctggaagct ccctcgtgcg ctctcctgtt    6480
ccgaccctgc cgcttaccgg atacctgtcc gcctttctcc cttcgggaag cgtggcgctt    6540
tctcaatgct cacgctgtag gtatctcagt tcggtgtagg tcgttcgctc caagctgggc    6600
tgtgtgcacg aaccccccgt tcagcccgac cgctgcgcct tatccggtaa ctatcgtctt    6660
```

| | |
|---|---:|
| gagtccaacc cggtaagaca cgacttatcg ccactggcag cagccactgg taacaggatt | 6720 |
| agcagagcga ggtatgtagg cggtgctaca gagttcttga agtggtggcc taactacggc | 6780 |
| tacactagaa ggacagtatt tggtatctgc gctctgctga agccagttac cttcggaaaa | 6840 |
| agagttggta gctcttgatc cggcaaacaa accaccgctg gtagcggtgg ttttttttgtt | 6900 |
| tgcaagcagc agattacgcg cagaaaaaaa ggatctcaag aagatccttt gatcttttct | 6960 |
| acggggtctg acgctcagtg gaacgaaaac tcacgttaag ggattttggt catgagatta | 7020 |
| tcaaaaagga tcttcaccta gatccttttta aattaaaaat gaagttttaa atcaatctaa | 7080 |
| agtatatatg agtaaacttg gtctgacagt taccaatgct taatcagtga ggcacctatc | 7140 |
| tcagcgatct gtctatttcg ttcatccata gttgcctgac tc | 7182 |

<210> SEQ ID NO 9
<211> LENGTH: 7170
<212> TYPE: DNA
<213> ORGANISM: Artificial Sequence
<220> FEATURE:
<223> OTHER INFORMATION: Based on equine encephalitis virus

<400> SEQUENCE: 9

| | |
|---|---:|
| gggggggggg ggcgctgagg tctgcctcgt gaagaaggtg ttgctgactc ataccaggcc | 60 |
| tgaatcgccc catcatccag ccagaaagtg agggagccac ggttgatgag agctttgttg | 120 |
| taggtggacc agttggtgat tttgaacttt tgctttgcca cggaacggtc tgcgttgtcg | 180 |
| ggaagatgcg tgatctgatc cttcaactca gcaaaagttc gatttattca acaaagccgc | 240 |
| cgtcccgtca agtcagcgta atgctctgcc agtgttacaa ccaattaacc aattctgatt | 300 |
| agaaaaactc atcgagcatc aaatgaaact gcaatttatt catatcagga ttatcaatac | 360 |
| catattttttg aaaaagccgt ttctgtaatg aaggagaaaa ctcaccgagg cagttccata | 420 |
| ggatggcaag atcctggtat cggtctgcga ttccgactcg tccaacatca atacaaccta | 480 |
| ttaatttccc ctcgtcaaaa ataaggttat caagtgagaa atcaccatga gtgacgactg | 540 |
| aatccggtga gaatggcaaa agcttatgca tttctttcca gacttgttca acaggccagc | 600 |
| cattacgctc gtcatcaaaa tcactcgcat caaccaaacc gttattcatt cgtgattgcg | 660 |
| cctgagcgag acgaaatacg cgatcgctgt taaaaggaca attacaaaca ggaatcgaat | 720 |
| gcaaccggcg caggaacact gccagcgcat caacaatatt ttcacctgaa tcaggatatt | 780 |
| cttctaatac ctggaatgct gttttcccgg ggatcgcagt ggtgagtaac catgcatcat | 840 |
| caggagtacg gataaaatgc ttgatggtcg gaagaggcat aaattccgtc agccagttta | 900 |
| gtctgaccat ctcatctgta acatcattgg caacgctacc tttgccatgt ttcagaaaca | 960 |
| actctggcgc atcgggcttc ccatacaatc gatagattgt cgcacctgat tgcccgacat | 1020 |
| tatcgcgagc ccatttatac ccatataaat cagcatccat gttggaattt aatcgcggcc | 1080 |
| tcgagcaaga cgtttcccgt tgaatatggc tcataacacc ccttgtatta ctgtttatgt | 1140 |
| aagcagacag ttttattgtt catgatgata tttttttatc ttgtgcaatg taacatcaga | 1200 |
| gattttgaga cacaacgtgg ctttcccccc ccccccggca tgcctgcagg tcgacataaa | 1260 |
| tcaatattgg ctattggcca ttgcatacgt tgtatctata tcataatatg tacatttata | 1320 |
| ttggctcatg tccaatatga ccgccatgtt gacattgatt attgactagt tattaatagt | 1380 |
| aatcaattac ggggtcatta gttcatagcc catatatgga gttccgcgtt acataactta | 1440 |
| cggtaaatgg cccgcctcgt gaccgcccaa cgacccccgc ccattgacgt caataatgac | 1500 |
| gtatgttccc atagtaacgc caatagggac tttccattga cgtcaatggg tggagtattt | 1560 |

```
acggtaaaact gcccacttgg cagtacatca agtgtatcat atgccaagtc cggcccccta   1620
ttgacgtcaa tgacggtaaa tggcccgcct ggcattatgc ccagtacatg accttacggg   1680
actttcctac ttggcagtac atctacgtat tagtcatcgc tattaccatg gtgatgcggt   1740
tttggcagta caccaatggg cgtggatagc ggtttgactc acggggattt ccaagtctcc   1800
accccattga cgtcaatggg agtttgtttt ggcaccaaaa tcaacgggac tttccaaaat   1860
gtcgtaataa ccccgccccg ttgacgcaaa tgggcggtag gcgtgtacgg tgggaggtct   1920
atataagcag agctcgttta gtgaaccgtc agatcgcctg gagacgccat ccacgctgtt   1980
ttgacctcca tagaagacac cgggaccgat ccagcctccg cggccgggaa cggtgcattg   2040
gaacgcggat tccccgtgcc aagagtgacg taagtaccgc ctatagactc tataggcaca   2100
cccctttggc tcttatgcat gctatactgt ttttggcttg gggcctatac accccgctc   2160 cttatgctat aggtgatggt atagcttagc ctataggtgt gggttattga ccattattga   2220
ccactcccct attggtgacg atactttcca ttactaatcc ataacatggc tctttgccac   2280
aactatctct attggctata tgccaatact ctgtccttca gagactgaca cggactctgt   2340 attttttacag gatggggtcc catttattat ttacaaattc acatatacaa caacgccgtc   2400
ccccgtgccc gcagttttta ttaaacatag cgtgggatct ccacgcgaat ctcgggtacg   2460
tgttccggac atgggctctt ctccggtagc ggcggagctt ccacatccga gccctggtcc   2520
catgcctcca gcggctcatg gtcgctcggc agctccttgc tcctaacagt ggaggccaga   2580
cttaggcaca gcacaatgcc caccaccacc agtgtgccgc acaaggccgt ggcggtaggg   2640
tatgtgtctg aaaatgagct cggagattgg gctcgcaccg tgacgcagat ggaagactta   2700
aggcagcggc agaagaagat gcaggcagct gagttgttgt attctgataa gagtcagagg   2760
taactcccgt tgcggtgctg ttaacggtgg agggcagtgt agtctgagca gtactcgttg   2820
ctgccgcgcg cgccaccaga cataatagct gacagactaa cagactgttc ctttccatgg   2880
gtcttttctg cagtcaccgt ccaagcttgc ggccgcgcca ccatgagcct ggtgaccgcc   2940
ctgtgcgtgc tgtccaacgt gaccttcccc tgcgacaagc ccccgtgtg ctacagcctg   3000 gccccgagc ggaccctgga cgtgctggaa gagaacgtgg acaaccccaa ctacgacacc   3060
ctgctggaaa acgtgctgaa gtgccccagc aggcggccca gcggagcat caccgacgac   3120 ttcacccctga ccagccccta cctgggcttc tgccccatcat gccggcacag cgcccccatgc   3180 ttcagcccca tcaagatcga aacgtgtgg gacgagagcg acgacggcag catccggatc   3240
caggtgtccg cccagttcgg ctacaaccag gccggcaccg ccgacgtgac caagttccgg   3300
tacatgagct acgaccacga ccacgatatc aaggaagata gcatggaaaa gctggccatc   3360
agcaccagcg gccctgcag acggctgggc cacaagggc actttctgct ggcccagtgc   3420 cccctggcg acagcgtgac cgtgagcatc accagcggcg ccagcgagaa cagctgcacc   3480
gtggagaaga agatccggcg gaagttcgtg gccggagg aatacctgtt ccccccgtg   3540 cacggcaagc tggtgaagtg ccacgtgtac gaccacctga aagagaccag cgccggctac   3600
atcaccatgc accggccagg ccccacgcc tacaagagct acctggaaga ggccagcggc   3660
gaggtgtaca tcaagccccc cagcggcaag aacgtgacct acgagtgcaa gtgcggcgac   3720
tacagcaccg gcatcgtgag caccccgacc aagatgaacg gctgcaccaa ggccaagcag   3780
tgcatcgcct acaagcggga ccagaccaag tgggtgttca acagccccga cctgatccgg   3840
cacaccgacc acagcgtgca gggcaaactg cacatcccct tccggctgac ccccaccgtg   3900
```

```
tgccccgtgc ccctggccca caccctacc gtgacaaagt ggttcaaggg catcacactg    3960
cacctgaccg ccaccggcc cacctgctg accacccgga agctgggcct gagggccgat    4020
gccaccgccg agtggatcac cggcaccacc tcccggaact tcagcgtggg cagagagggc    4080
ctggaatacg tctggggcaa ccacgagccc gtgagagtgt gggcccagga aagcgcccca    4140
ggcgaccccc acggctggcc ccacgagatc atcatccact actaccaccg gcaccccgtg    4200
tacaccgtga tcgtgctgtg cggcgtggcc ctggccatcc tggtgggcac cgccagcagc    4260
gccgcctgca tcgccaaggc caggcgggac tgcctgaccc cctacgccct ggccccaac    4320 gccaccgtgc caaccgccct ggccgtgctg tgctgcatcc ggcccaccaa cgccgagacc    4380
ttcggcgaga ccctgaacca cctgtggttc aacaaccagc ccttcctgtg ggcccagctg    4440
tgcatccccc tggccgccct gatcatcctg ttccggtgct tcagctgctg catgcctttt    4500
ctgctggtcg ccggcgtgtg cctgggcaag gtggacgcct tcgagcacgc caccaccgtg    4560
cccaacgtgc ccggcatccc ctacaaggcc ctggtggaga gggccggcta cgccccctg    4620 aacctggaaa tcaccgtggt gtccagcgag ctgacccct ccaccaacaa agaatacgtg    4680
acctgcaagt tccacaccgt ggtgccctcc ccaggtga agtgctgcgg cagcctggaa    4740
tgcaaggcca gcagcaaggc cgactacacc tgccgggtgt tcggcggcgt gtaccccttc    4800
atgtggggcg gagcacagtg cttctgcgac tccagaaca cccagctgtc cgaggcctac    4860
gtggagttcg ccccccgactg caccatcgac cacgccgtgg ccctgaaggt gcacacagcc    4920
gccctgaaag tgggcctgcg gatcgtgtac ggcaacacca ccgccaggct ggacaccttc    4980
gtgaacggcg tgaccccgg cagcagccgg gacctgaagg tgatcgccgg acccatctcc    5040
gccgccttca gccccttcga ccacaaggtg gtgatccgga agggcctggt gtacaactac    5100
gacttccccg agtacggcgc catgaaccct ggcgccttcg cgacatcca ggccagctcc    5160 ctggacgcca ccgacatcgt ggcccggacc gacatccggc tgctgaagcc cagcgtgaag    5220
aacatccacg tgcccatcac ccaggccgtg agcggctacg agatgtggaa gaacaacagc    5280
ggcagacccc tgcaggaaac cgcccccttc ggctgcaaga tcgaggtgga gccctgcgg    5340 gccaccaact gcgcctacgg ccacatcccc atcagcatcg acatcccga cgccgccttc    5400 gtgcggagca gcgagagccc caccatcctg aagtgagct gtaccgtggc cgactgcatc    5460
tacagcgccg acttcggcgg ctccctgacc ctgcagtaca aggccaaccg ggagggccac    5520
tgccccgtgc acagccacag caccaccgcc gtgctgaaag aggccaccac ccacgtcacc    5580
gccacaggca gcatcaccct gcacttcagc accagctccc cccaggccaa cttcatcgtg    5640
agcctgtgcg gcaagaaaac cacctgcaac gccgagtgca gccccctgc cgaccacatc    5700 atcggcgagc ctcacaaggt ggaccaggaa ttccaggccg ccgtcagcaa gaccagctgg    5760
aactggctgc tggccctgtt cggcggagcc agcagcctga tcgtggtggg cctgattgtg    5820
ctggtgtgca gcagcatgct gatcaacacc cggcggtgat gaagatctac gtatgatcag    5880
cctcgactgt gccttctagt tgccagccat ctgttgtttg cccctccccc gtgccttcct    5940
tgaccctgga aggtgccact cccactgtcc tttcctaata aaatgaggaa attgcatcgc    6000
attgtctgag taggtgtcat tctattctgg ggggtgggt ggggcaggac agcaagggg    6060 aggattggga agacaatagc aggcatgctg gggatgcggt gggctctatg gcttctgagg    6120
cggaaagaac cagctgggc tcgacagctc gactctagaa ttgcttcctc gctcactgac    6180
tcgctgcgct cggtcgttcg gctgcggcga gcggtatcag ctcactcaaa ggcggtaata    6240
cggttatcca cagaatcagg ggataacgca ggaaagaaca tgtgagcaaa aggccagcaa    6300
```

```
aaggccagga accgtaaaaa ggccgcgttg ctggcgtttt tccataggct ccgccccct    6360 gacgagcatc acaaaaatcg acgctcaagt cagaggtggc gaaacccgac aggactataa   6420
agataccagg cgtttccccc tggaagctcc ctcgtgcgct ctcctgttcc gaccctgccg   6480
cttaccggat acctgtccgc ctttctccct tcgggaagcg tggcgctttc tcaatgctca   6540
cgctgtaggt atctcagttc ggtgtaggtc gttcgctcca agctgggctg tgtgcacgaa   6600
ccccccgttc agcccgaccg ctgcgcctta tccggtaact atcgtcttga gtccaacccg   6660
gtaagacacg acttatcgcc actggcagca gccactggta acaggattag cagagcgagg   6720
tatgtaggcg gtgctacaga gttcttgaag tggtggccta actacggcta cactagaagg   6780
acagtatttg gtatctgcgc tctgctgaag ccagttacct tcggaaaaag agttggtagc   6840
tcttgatccg gcaaacaaac caccgctggt agcggtggtt ttttgtttg caagcagcag    6900 attacgcgca gaaaaaaagg atctcaagaa gatcctttga tcttttctac ggggtctgac   6960
gctcagtgga acgaaaactc acgttaaggg attttggtca tgagattatc aaaaaggatc   7020
ttcacctaga tccttttaaa ttaaaaatga agttttaaat caatctaaag tatatatgag   7080
taaacttggt ctgacagtta ccaatgctta atcagtgagg cacctatctc agcgatctgt   7140
ctatttcgtt catccatagt tgcctgactc                                    7170
```

EQUINE ENCEPHALITIS VIRUS VACCINES AND METHODS OF USING THEREOF

CROSS-REFERENCE TO RELATED APPLICATIONS

This application claims the benefit of U.S. Provisional Ser. No. 61/620,122, filed 4 Apr. 2012, which is herein incorporated by reference in its entirety.

REFERENCE TO A SEQUENCE LISTING SUBMITTED VIA EFS-WEB

The content of the ASCII text file of the sequence listing named "20120523_034047_057_seq_ST25" which is 54.6 kb in size was created on 23 May 2012 and electronically submitted via EFS-Web herewith the application is incorporated herein by reference in its entirety.

ACKNOWLEDGEMENT OF GOVERNMENT SUPPORT

This invention was made by employees of the United States Army Medical Research and Materiel Command, which is an agency of the United States Government. The Government has certain rights in this invention.

BACKGROUND OF THE INVENTION

1. Field of the Invention

The present invention generally relates to nucleic acid molecules derived from equine encephalitis viruses and compositions and methods thereof.

2. Description of the Related Art

Venezuelan equine encephalitis virus (VEEV), eastern equine encephalitis virus (EEEV), and western equine encephalitis virus (WEEV) are non-segmented, positive-sense RNA viruses of the genus *Alphavirus* in the family Togaviridae. See Griffin (2001) "*Alphaviruses*", p. 917-962, in FIELDS VIROLOGY, vol. 4. Lippincott, Williams, and Wilkins, Philadelphia, Pa. Naturally transmitted by mosquitoes through rodent or bird hosts, VEEV, EEEV, and WEEV are highly pathogenic for equines and humans and have caused periodic epizootics throughout North, Central, and South America. See Tsai (1991) Infect Dis Clin North Am 5:73-102. Human infection with these New World alphaviruses typically results in an acute, incapacitating disease characterized by fever, headache, lymphopenia, myalgia, and malaise. See Bale (1993) Med Clin North Am 77:25-42. Severe neurological disease, including fatal encephalitis, can also result from VEEV, EEEV, and WEEV infection of humans. Although the human case-fatality rates are estimated to be low for VEEV (≤1%) and WEEV (8-15%), EEEV is the most severe of the arbovirus encephalitides with a human case-fatality rate estimated to be 30-70%. See Steele et al. (2007) "alphavirus Encephalitides" p. 241-270, in MEDICAL ASPECTS OF BIOLOGICAL WARFARE. BORDEN INSTITUTE (U.S. Army Walter Reed), Washington, D.C. However, numerous documented laboratory accidents and the results of animal studies have demonstrated that VEEV, EEEV, and WEEV are also highly infectious in aerosols, and infection with aerosolized virus could potentially result in higher mortality than that observed with natural infection. See Franz et al. (2001) Clin Lab Med 21:435-73; Hanson (1967) Science 158:1283-6; and Kortepeter et al. (2001) J Environ Health 63:21-4. In addition to producing incapacitating or lethal infections and being infectious in aerosols, these encephalitic alphaviruses are also easily grown to high titers in inexpensive and unsophisticated cell culture systems and are relatively stable. As a result, VEEV, EEEV, and WEEV represent significant potential biological defense threats and are classified as Category B priority biodefense agents by both the Centers for Disease Control and Prevention and the National Institute of Allergy and Infectious Diseases.

Although there are no licensed human vaccines for the encephalitic alphaviruses, live-attenuated and formalin-inactivated vaccines are currently being utilized under Investigational New Drug (IND) status to protect laboratory workers and other at-risk personnel. A live-attenuated vaccine for VEEV, TC-83, provides long-lasting immunity and protection from both subcutaneous and aerosol VEEV challenges; however, it causes adverse reactions in approximately 25% of recipients, and approximately 20% of recipients fail to develop a detectable neutralizing antibody response. See McKinney et al. (1963) Am J Trop Med Hyg 12:597-603; and Pittman et al. (1996) Vaccine 14:337-43. C-84 (formalin-inactivated TC-83 VEEV vaccine), and EEEV and WEEV formalin-inactivated vaccines are well tolerated, but they require frequent boosting to elicit detectable neutralizing antibody responses in humans and have provided poor protection against aerosol viral challenge in animal studies. See Cole et al. (1973) Appl Microbiol 25:262-5; Bartelloni et al. (1970) Am J Trop Med Hyg 19:123-6; and Bartelloni et al. (1971) Am J Trop Med Hyg 20:146-9. Due to the significant limitations associated with the existing live-attenuated and formalin-inactivated vaccines currently being utilized under IND status, the development of improved vaccines that can safely and effectively protect against encephalitic alphavirus infections in humans is needed.

Next-generation VEEV vaccines, including live-attenuated, inactivated, attenuated Sindbis/VEEV chimeric viruses, alphavirus replicons, and DNA vaccines, are all currently at various stages of development. See Paessler & Weaver (2009) Vaccine 27 Suppl 4:D80-5. Genetic vaccination with DNA plasmids expressing immunogenic proteins has numerous inherent advantages as a platform for the development of next-generation vaccines. Among the benefits of this method are that DNA vaccines can be rapidly and cost-effectively produced without the need to propagate a pathogen, do not require the inactivation of infectious organisms, avoid problems of preexisting or vector-induced immunity due to lack of a host immune response to the plasmid backbone, and have exhibited a favorable safety profile in numerous human clinical trials. See Dupuy & Schmaljohn (2009) Expert Rev Vaccines 8:1739-54.

In previous studies, mice vaccinated with a DNA vaccine expressing the structural proteins (C-E3-E2-6K-E1) of VEEV subtype IAB (strain Trinidad Donkey) by particle-mediated epidermal delivery (PMED) or "gene gun", in which plasmid DNA-coated gold particles are delivered intradermally in a ballistic manner, developed strong overall antibody responses against VEEV IAB. Unfortunately, the VEEV-neutralizing antibody responses were low, and only 80% protection against lethal aerosol challenge was observed. See Riemenschneider et al. (2003) Vaccine 21:4071-80. Cynomolgus macaques vaccinated with this VEEV DNA vaccine by PMED developed detectable levels of VEEV IAB-neutralizing antibodies, but only partial protection was observed upon aerosol challenge. See Dupuy et al. (2010) Vaccine 28:7345-50.

In other studies to develop a human vaccine for encephalitic alphaviruses, directed molecular evolution or "gene shuffling" of the envelope protein genes was used as an attempt to improve the neutralizing antibody response to VEEV, EEEV, and WEEV DNA vaccines. DNA vaccines expressing representative variants from a library in which the E2 envelope glycoprotein genes of five parent viruses (VEEV subtypes IAB and IE, Mucambo virus, EEEV (strain PE6), and WEEV (strain CBA87) were recombined and the E1 envelope glycoprotein gene of VEEV IAB was held constant elicited significantly increased neutralizing antibody titers to VEEV IAB compared to the wild-type parent VEEV DNA vaccine and provided improved protection against aerosol VEEV IAB challenge in mice. See Dupuy et al. (2009) Vaccine 27:4152-60. Unfortunately, in addition to the in vitro gene recombination being technically difficult and the screening of variants for improved immunogenicity being labor-intensive, the studies failed to result in variant envelope glycoprotein vaccines having improved immunogenicity against EEEV and WEEV as compared to the wild-type parent EEEV and WEEV DNA vaccines.

Therefore, a need still exists for safe and effective vaccines to protect against equine encephalitis viruses (EEVs) such as VEEV, EEEV, and WEEV.

SUMMARY OF THE INVENTION

The present invention provides nucleotide sequence which encodes a plurality of structural proteins, except the capsid, of an equine encephalitis virus, wherein the nucleotide sequence is codon-optimized for mammalian expression. In some embodiments, the nucleotide sequences are codon-optimized for expression in humans. In some embodiments, the structural proteins of the plurality of structural proteins are selected from the group consisting of E3, E2, 6K and E1. In some embodiments, the plurality of structural proteins comprises, consists essentially of, or consists of E3, E2, 6K and E1. In some embodiments, the equine encephalitis virus is Venezuelan equine encephalitis virus (VEEV), western equine encephalitis virus (WEEV), or eastern equine encephalitis virus (EEEV). In some embodiments, the vector sequence is that of eukaryotic expression vector pWRG7077. In some embodiments, the nucleotide sequence has at least about 85%, preferably about 90%, more preferably about 95%, or most preferably about 99% or more sequence identity to SEQ ID NO:1, SEQ ID NO:3, or SEQ ID NO:5. In some embodiments, the nucleotide sequence is selected from the group consisting of SEQ ID NO:1, SEQ ID NO:3, and SEQ ID NO:5. In some embodiments, the nucleotide sequence are provided in the form of a plasmid, i.e. are contained within a vector sequence, such as the eukaryotic expression vector pWRG7077.

In some embodiments, the present invention provides compositions comprising, consisting essentially of, or consisting of one or more $EEV_{CO}$ polynucleotides and/or one or more $EEV_{CO}$ antibodies raised against the one or more $EEV_{CO}$ polynucleotides. Such $EEV_{CO}$ polynucleotides comprise, consist essentially of, or consist of a nucleotide sequence which encodes a plurality of structural proteins, except the capsid, of an equine encephalitis virus, wherein the nucleotide sequence is codon-optimized for mammalian expression. In some embodiments, the nucleotide sequences are codon-optimized for expression in humans. In some embodiments, the structural proteins of the plurality of structural proteins are selected from the group consisting of E3, E2, 6K and E1. In some embodiments, the plurality of structural proteins comprises, consists essentially of, or consists of E3, E2, 6K and E1. In some embodiments, the equine encephalitis virus is Venezuelan equine encephalitis virus (VEEV), western equine encephalitis virus (WEEV), or eastern equine encephalitis virus (EEEV). In some embodiments, the $EEV_{CO}$ polynucleotides are contained within a vector sequence such as the eukaryotic expression vector pWRG7077. In some embodiments, the nucleotide sequence has at least about 85%, preferably about 90%, more preferably about 95%, or most preferably about 99% or more sequence identity to SEQ ID NO:1, SEQ ID NO:3, or SEQ ID NO:5. In some embodiments, the nucleotide sequence is selected from the group consisting of SEQ ID NO:1, SEQ ID NO:3, and SEQ ID NO:5. In some embodiments, the $EEV_{CO}$ polynucleotide is provided in the form of an $EEV_{CO}$ plasmid, i.e. contained within a vector sequence such as the eukaryotic expression vector pWRG7077. In some embodiments, the sequence of the $EEV_{CO}$ plasmid has at least about 85%, preferably about 90%, more preferably about 95%, or most preferably about 99% or more sequence identity to SEQ ID NO:7, SEQ ID NO:8, or SEQ ID NO:9. In some embodiments, the compositions of the present invention further comprise pharmaceutically acceptable carriers and/or adjuvants. In some embodiments, the one or more $EEV_{CO}$ polynucleotides are provided in the compositions in immunogenic amounts and/or therapeutically effective amounts. In some embodiments, the one or more $EEV_{CO}$ antibodies are provided in the compositions in therapeutically effective amounts.

In some embodiments, the present invention provides methods of eliciting an immune response in a subject, preferably a mammalian subject, more preferably a primate, most preferably a human, which comprises, consists essentially of, or consists of administering to the subject at least one immunogenic amount of (a) at least one $EEV_{CO}$ polynucleotide or at least one $EEV_{CO}$ plasmid as disclosed herein, (b) at least one plasmid comprising, consisting essentially of, or consisting of a vector sequence and a nucleotide sequence that has at least about 85%, preferably about 90%, more preferably about 95%, or most preferably about 99% or more sequence identity to SEQ ID NO:1, SEQ ID NO:3, or SEQ ID NO:5; (c) at least one plasmid comprising, consisting essentially of, or consisting of a vector sequence and a nucleotide sequence selected from the group consisting of SEQ ID NO:1, SEQ ID NO:3, and SEQ ID NO:5; (d) a composition comprising, consisting essentially of, or consisting of one or more plasmids according to (a)-(c) above; or (e) a composition comprising, consisting essentially of, or consisting of nucleotide sequences having SEQ ID NO:1, SEQ ID NO:3, and SEQ ID NO:5, wherein the nucleotide sequences may be contained within one or more vector sequences. In some embodiments, the $EEV_{CO}$ polynucleotides comprise, consist essentially of, or consist of a nucleotide sequence which encodes a plurality of structural proteins, except the capsid, of an equine encephalitis virus, wherein the nucleotide sequence is codon-optimized for mammalian expression. In some embodiments, the nucleotide sequences are codon-optimized for expression in humans. In some embodiments, the structural proteins of the plurality of structural proteins are selected from the group consisting of E3, E2, 6K and E1. In some embodiments, the plurality of structural proteins comprises, consists essentially of, or consists of E3, E2, 6K and E1. In some embodiments, the equine encephalitis virus is Venezuelan equine encephalitis virus (VEEV), western equine encephalitis virus (WEEV), or eastern equine encephalitis virus (EEEV). In some embodiments the $EEV_{CO}$ polynucleotides are contained within a vector sequence such as the eukaryotic expression vector pWRG7077. In some embodiments, the immune response is a cellular immune response.

In some embodiments, the immune response is one that is observable and/or measurable using methods known in the art. In some embodiments, the amount of the immune response is a total IgG antibody response and/or a neutralizing antibody response that is significantly more than that provided by a corresponding $EEV_{WT}$ control. In some embodiments, the amount of the immune response is a total IgG antibody response and/or a neutralizing antibody response that is substantially similar to that provided by TC-83. In some embodiments, the immunogenic amount is one that results in an immunogenic response as compared to a negative control. In some embodiments, the immunogenic amount is about 10-1250 µg/kg subject. In some embodiments, the immunogenic amount is administered as separate doses at different times. In some embodiments, an additional immunogenic amount, e.g. booster dose, is subsequently administered. In some embodiments, the immunogenic amounts are administered by a particle-mediated epidermal delivery method.

In some embodiments, the present invention provides methods of immunizing a subject, preferably a mammalian subject, more preferably a primate, most preferably a human, against one or more equine encephalitis viruses which comprises, consists essentially of, or consists of administering to the subject at least one immunogenic amount of (a) at least one $EEV_{CO}$ polynucleotide or at least one $EEV_{CO}$ plasmid as disclosed herein, (b) at least one plasmid comprising, consisting essentially of, or consisting of a vector sequence and a nucleotide sequence that has at least about 85%, preferably about 90%, more preferably about 95%, or most preferably about 99% or more sequence identity to SEQ ID NO:1, SEQ ID NO:3, or SEQ ID NO:5; (c) at least one plasmid comprising, consisting essentially of, or consisting of a vector sequence and a nucleotide sequence selected from the group consisting of SEQ ID NO:1, SEQ ID NO:3, and SEQ ID NO:5; (d) a composition comprising, consisting essentially of, or consisting of one or more plasmids according to (a)-(c) above; or (e) a composition comprising, consisting essentially of, or consisting of nucleotide sequences having SEQ ID NO:1, SEQ ID NO:3, and SEQ ID NO:5, wherein the nucleotide sequences may be contained within one or more vector sequences. In some embodiments, the $EEV_{CO}$ polynucleotides comprise, consist essentially of, or consist of a nucleotide sequence which encodes a plurality of structural proteins, except the capsid, of an equine encephalitis virus, wherein the nucleotide sequence is codon-optimized for mammalian expression. In some embodiments, the nucleotide sequences are codon-optimized for expression in humans. In some embodiments, the structural proteins of the plurality of structural proteins are selected from the group consisting of E3, E2, 6K and E1. In some embodiments, the plurality of structural proteins comprises, consists essentially of, or consists of E3, E2, 6K and E1. In some embodiments, the equine encephalitis virus is Venezuelan equine encephalitis virus (VEEV), western equine encephalitis virus (WEEV), or eastern equine encephalitis virus (EEEV). In some embodiments the $EEV_{CO}$ polynucleotides are contained within a vector sequence such as the eukaryotic expression vector pWRG7077. In some embodiments, the immune response is a cellular immune response. In some embodiments, the immune response is one that is observable and/or measurable using methods known in the art. In some embodiments, the amount of the immune response is a total IgG antibody response and/or a neutralizing antibody response that is significantly more than that provided by a corresponding $EEV_{WT}$ control. In some embodiments, the amount of the immune response is a total IgG antibody response and/or a neutralizing antibody response that is substantially similar to that provided by TC-83. In some embodiments, the immunogenic amount is one that results in an immunogenic response as compared to a negative control. In some embodiments, the immunogenic amount is about 10-1250 µg/kg subject. In some embodiments, the immunogenic amount is administered as separate doses at different times. In some embodiments, an additional immunogenic amount, e.g. booster dose, is subsequently administered. In some embodiments, the immunogenic amounts are administered by a particle-mediated epidermal delivery method. In some embodiments, the immunogenic amount confers to the subject 100% survivability against exposure to one or more equine encephalitis viruses selected from the group consisting of Venezuelan equine encephalitis virus (VEEV), western equine encephalitis virus (WEEV), or eastern equine encephalitis virus (EEEV). In some embodiments, the one or more equine encephalitis viruses are aerosolized. In some embodiments, the immunogenic amount is administered by a particle-mediated epidermal delivery method.

In some embodiments, the present invention provides a vaccine which comprises, consists essentially of, or consists of an immunogenic amount of polynucleotides having SEQ ID NO:1, SEQ ID NO:3, SEQ ID NO:5, SEQ ID NO:7, SEQ ID NO:8, or SEQ ID NO:9. In some embodiments, the vaccine may further comprise one or more pharmaceutically acceptable carriers and/or adjuvants. In some embodiments, when administered to a mammalian subject, preferably a primate, more preferably a human, the vaccine confers to the subject 100% survivability against exposure to one or more equine encephalitis viruses selected from the group consisting of Venezuelan equine encephalitis virus (VEEV), western equine encephalitis virus (WEEV), or eastern equine encephalitis virus (EEEV). In some embodiments, the one or more equine encephalitis viruses are aerosolized. In some embodiments, the vaccine is administered by a particle-mediated epidermal delivery method.

In some embodiments, the present invention provides kits which comprise one or more $EEV_{CO}$ polynucleotides, one or more $EEV_{CO}$ plasmids, one or more $EEV_{CO}$ antibodies, and/or compositions thereof packaged together with a delivery device for administration to a subject. The kits may further include instructions for use. The one or more $EEV_{CO}$ polynucleotides, one or more $EEV_{CO}$ plasmids, one or more $EEV_{CO}$ antibodies, and/or compositions may be provided in single unit dosage forms and the kits may comprise one or more single unit dosages.

In some embodiments, the present invention provides one or more $EEV_{CO}$ polynucleotides, one or more $EEV_{CO}$ plasmids, one or more $EEV_{CO}$ antibodies, and/or compositions thereof for use as a medicament. In some embodiments, the present invention provides use of one or more $EEV_{CO}$ polynucleotides, one or more $EEV_{CO}$ plasmids, one or more $EEV_{CO}$ antibodies, and/or compositions thereof for the immunization of a subject. In some embodiments, the present invention provides one or more $EEV_{CO}$ polynucleotides, one or more $EEV_{CO}$ plasmids, one or more $EEV_{CO}$ antibodies, and/or compositions thereof for the immunization of a subject. In some embodiments, the present invention provides one or more $EEV_{CO}$ polynucleotides, one or more $EEV_{CO}$ plasmids, one or more $EEV_{CO}$ antibodies, and/or compositions thereof for use in immunizing a subject against infection by an EEV, wherein the one or more $EEV_{CO}$ polynucleotides, one or more $EEV_{CO}$ plasmids, one or more EEV$_{CO}$ antibodies, and/or compositions thereof are administered by a dosage regime which results in an immune response in the subject.

In some embodiments, the present invention is directed to use of one or more EEV$_{CO}$ polynucleotides, one or more EEV$_{CO}$ plasmids, one or more EEV$_{CO}$ antibodies, and/or compositions thereof. In some embodiments, the present invention is directed to use of SEQ ID NO:1, SEQ ID NO:3, SEQ ID NO:5, SEQ ID NO:7, SEQ ID NO:8, and/or SEQ ID NO:9. In some embodiments, the present invention is directed to use of one or more EEV$_{CO}$ polynucleotides, one or more EEV$_{CO}$ plasmids, one or more EEV$_{CO}$ antibodies, and/or compositions thereof for eliciting an immune response in a subject and/or immunizing a subject against infection by an EEV. In some embodiments, the present invention is directed to use of SEQ ID NO:1, SEQ ID NO:3, SEQ ID NO:5, SEQ ID NO:7, SEQ ID NO:8, and/or SEQ ID NO:9 for eliciting an immune response in a subject and/or immunizing a subject against infection by an EEV. In some embodiments, the present invention is directed to use of one or more EEV$_{CO}$ polynucleotides, one or more EEV$_{CO}$ plasmids, one or more EEV$_{CO}$ antibodies, and/or compositions thereof for the manufacture of a medicament for eliciting an immune response in a subject and/or immunizing a subject against infection by an EEV, wherein the medicament is administered in an immunogenic amount and/or by a particle-mediated epidermal delivery method. In some embodiments, the present invention is directed to use of SEQ ID NO:1, SEQ ID NO:3, SEQ ID NO:5, SEQ ID NO:7, SEQ ID NO:8, and/or SEQ ID NO:9 for the manufacture of a medicament for eliciting an immune response in a subject and/or immunizing a subject against infection by an EEV, wherein the medicament is administered in an immunogenic amount and/or by a particle-mediated epidermal delivery method. In some embodiments, the present invention provides one or more EEV$_{CO}$ polynucleotides, one or more EEV$_{CO}$ plasmids, one or more EEV$_{CO}$ antibodies, and/or compositions thereof for use in immunizing against an EEV, wherein the one or more EEV$_{CO}$ polynucleotides, the one or more EEV$_{CO}$ plasmids, the one or more EEV$_{CO}$ antibodies, and/or the compositions thereof is/are administered in an immunogenic amount and/or by a particle-mediated epidermal delivery method.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIGS. 3A and 3B are graphs summarizing the antibody responses of vaccinated mice. Female BALB/c mice (N=6 per group) were vaccinated twice at a 3-week interval with 5 μg of the VEEV$_{CO}$ plasmid delivered by i.m. injection with and without EP. Serum samples obtained 3 weeks after each vaccination were assayed for total IgG anti-VEEV antibodies by ELISA and for VEEV-neutralizing antibodies by PRNT. The group mean log$_{10}$ ELISA (FIG. 3A) and PRNT$_{80}$ (FIG. 3B) titers along with the SEM are shown. *$p<0.05$, $p<0.01$, and ***$p<0.0001$ for comparison between titers with and without EP.

FIGS. 4A and 4B are graphs summarizing the antibody responses of vaccinated mice. Female BALB/c mice (N=10 per group) were vaccinated twice at a 3-week interval with 5 μg of empty vector DNA, VEEV$_{COCAP}$ or VEEV$_{CO}$ plasmid delivered by i.m. EP. Positive control mice (N=10) each received a single vaccination with 0.5 ml of the live-attenuated VEEV IND vaccine TC-83 ($1\times10^4$ PFU) delivered by subcutaneous injection. Serum samples obtained 3 weeks after each vaccination were assayed for total IgG anti-VEEV antibodies by ELISA and for VEEV-neutralizing antibodies by PRNT. The group mean log$_{10}$ ELISA (FIG. 4A) and PRNT$_{80}$ (FIG. 4B) titers along with the SEM are shown. $p<0.01$, $p<0.001$, and ***$p<0.0001$ for comparison between titers for VEEV$_{COCAP}$, VEEV$_{CO}$, and TC-83.

FIG. 7 shows the antibody responses of vaccinated rabbits. Female New Zealand White rabbits (N=5) were vaccinated with 500 μg of the VEEV$_{CO}$ plasmid delivered by i.m. EP on days 0, 28, and 230 (indicated by arrowheads). Serum samples obtained from the rabbits on days 0, 28, 42, 230, 266, and 349 were analyzed for VEEV-neutralizing antibodies by PRNT. The group mean log$_{10}$ PRNT$_{80}$ titers along with the SEM are shown. *p<0.05 and ***p<0.005 for comparison between titers after boosting DNA vaccinations.

FIG. 8 is a graph showing the antibody responses of vaccinated nonhuman primates. Adult male cynomolgus macaques (N=4 per group) were vaccinated with 500 μg of the empty vector DNA plasmid or 500 μg or 50 μg of the VEEV$_{CO}$ plasmid delivered by i.m. EP at days 0 and 56 (indicated by arrowheads). Serum samples obtained from the macaques on days 0, 28, 56, 84, and 112 were analyzed for VEEV-neutralizing antibodies by PRNT. The group mean $\log_{10}$ PRNT$_{80}$ titers along with the SEM are shown. *****p<0.0001 for comparison between titers after boosting DNA vaccinations.

FIGS. 9A, 9B and 9C are graphs showing the data for the aerosol challenge of vaccinated macaques. Adult male cynomolgus macaques (N=4 per group) vaccinated with 500 μg of the empty vector DNA plasmid or 500 μg or 50 μg of the VEEV$_{CO}$ plasmid delivered by i.m. EP at days 0 and 56 were challenged with a calculated dose of $3 \times 10^8$ PFU (~300 ED$_{50}$) of VEEV IAB by the aerosol route. After challenge, the macaques were monitored for serum viremia by plaque assay (FIG. 9A), for fever responses by telemetry (FIG. 9B), and for lymphopenia by determining PBL counts (FIG. 9C). The group mean viremias, temperature elevations, and percent changes in peripheral blood lymphocyte (PBL) counts along with the SEM are shown. *p<0.05 and ****p<0.001 for comparison between the mean temperature elevations of macaques vaccinated with empty vector and VEEV$_{CO}$ plasmid.

FIG. 10A is a graph summarizing the antibody responses of vaccinated mice. Female BALB/c mice (N=10 per group) were vaccinated three times at a 3-week interval with 4 μg of empty vector DNA or VEEV$_{WT}$ plasmid or with 4 μg each of the VEEV$_{WT}$, EEEV$_{WT}$, and WEEV$_{WT}$ plasmids delivered by PMED. Positive control mice (N=10) each received a single vaccination with 0.5 ml of the live-attenuated VEEV IND vaccine TC-83 ($1 \times 10^4$ PFU) delivered by subcutaneous injection. Serum samples obtained 3 weeks after each vaccination were assayed for total IgG anti-VEEV antibodies by ELISA, and the serum samples obtained 3 weeks after the last vaccination were assayed for VEEV-neutralizing antibody responses by PRNT. The group mean $\log_{10}$ ELISA and PRNT$_{80}$ titers along with the SEM are shown.

FIG. 10B is a graph showing the survival of vaccinated mice. Female BALB/c mice (N=10 per group) vaccinated three times at a 3-week interval with 4 μg of empty vector DNA or VEEV$_{WT}$ plasmid or with 4 μg each of the VEEV$_{WT}$, EEEV$_{WT}$, and WEEV$_{WT}$ plasmids delivered by PMED and positive control mice (N=10) receiving a single vaccination with 0.5 ml of the live-attenuated VEEV IND vaccine TC-83 ($1 \times 10^4$ PFU) delivered by subcutaneous injection were challenged 4 weeks after the final vaccination with about $10^4$ PFU ($\geq 1,000$ LD$_{50}$) of VEEV IAB by the aerosol route. Kaplan-Meier survival analysis is shown indicating the percentage of surviving mice at each day of a 28-day post-challenge observation period.

FIGS. 11A and 11B are graphs summarizing the antibody responses of vaccinated mice. Female BALB/c mice (N=10 per group) were vaccinated twice at a 3-week interval with 5 μg of empty vector DNA or VEEV$_{CO}$ or 5 μg each of the VEEV$_{CO}$, EEEV$_{CO}$, and WEEV$_{CO}$ plasmids delivered by i.m. EP. Positive control mice (N=10) each received a single vaccination with 0.5 ml of the live-attenuated VEEV IND vaccine TC-83 ($1 \times 10^4$ PFU) delivered by subcutaneous injection. Serum samples obtained 3 weeks after each vaccination were assayed for total IgG anti-VEEV antibodies by ELISA and for VEEV-neutralizing antibodies by PRNT. The group mean $\log_{10}$ ELISA (FIG. 11A) and PRNT$_{80}$ (FIG. 11B) titers along with the SEM are shown.

FIG. 12 is a graph showing the survival of vaccinated mice. Female BALB/c mice (N=10 per group) vaccinated twice at a 3-week interval with 5 μg of empty vector DNA or VEEV$_{CO}$ or 5 μg each of the VEEV$_{CO}$, EEEV$_{CO}$, and WEEV$_{CO}$ plasmids delivered by i.m. EP and positive control mice (N=10) receiving a single vaccination with 0.5 ml of the live-attenuated VEEV IND vaccine TC-83 ($1 \times 10^4$ PFU) delivered by subcutaneous injection were challenged 4 weeks after the final vaccination with about $10^4$ PFU ($\geq 1,000$ LD$_{50}$) of VEEV IAB by the aerosol route. Kaplan-Meier survival analysis is shown indicating the percentage of surviving mice at each day of a 28-day post-challenge observation period.

FIG. 13 is a graph showing the cellular immune responses of vaccinated mice. Female BALB/c mice (N=6 per group) were vaccinated twice at a 3-week interval with 5 μg of empty vector or VEEV$_{CO}$ plasmid or 5 μg each of the VEEV$_{CO}$, EEEV$_{CO}$, and WEEV$_{CO}$ plasmids delivered by i.m. EP. Two weeks after the second vaccination, splenocytes were isolated and restimulated with no peptide, Concanavalin A, pools of overlapping peptides representing the unrelated β-Galactosidase protein, or pools of overlapping peptides representing the VEEV IAB E2 or E1 envelope glycoproteins and analyzed by IFN-γ ELISpot. The mean spot forming units (SFU) per $10^6$ cells along with the SEM for each group are shown (FIG. 12).

FIG. 14 shows the antibody responses of vaccinated rabbits. Female New Zealand White rabbits (N=5) were vaccinated with 500 μg of the VEEV$_{CO}$ plasmid or 500 μg each of the VEEV$_{CO}$, EEEV$_{CO}$, and WEEV$_{CO}$ plasmids delivered by i.m. EP on days 0, 28, and 230 (indicated by arrowheads). Serum samples obtained from the rabbits on days 0, 28, 42, 230, 266, and 349 were analyzed for VEEV-neutralizing antibodies by PRNT. The mean $\log_{10}$ PRNT$_{80}$ titers along with the SEM for each group are shown.

FIG. 15A is a graph summarizing the antibody responses of vaccinated mice. Female BALB/c mice (N=10 per group) were vaccinated three times at a 3-week interval with 4 μg of empty vector DNA or EEEV$_{WT}$ plasmid or with 4 μg each of the EEEV$_{WT}$, VEEV$_{WT}$, and WEEV$_{WT}$ plasmids delivered by PMED. Positive control mice (N=10) each received a single vaccination with 0.5 ml of the formalin-inactivated EEEV IND vaccine delivered by subcutaneous injection. Serum samples obtained 3 weeks after each vaccination were assayed for total IgG anti-VEEV antibodies by ELISA, and the serum samples obtained 3 weeks after the last vaccination were also assayed for VEEV-neutralizing antibody responses by PRNT. The group mean $\log_{10}$ ELISA and PRNT$_{80}$ titers along with the SEM are shown.

FIG. 15B is a graph showing the survival of vaccinated mice. Female BALB/c mice (N=10 per group) vaccinated three times at a 3-week interval with 4 μg of empty vector DNA or EEEV$_{WT}$ plasmid or with 4 μg each of the EEEV$_{WT}$, VEEV$_{WT}$, and WEEV$_{WT}$ plasmids delivered by PMED and positive control mice (N=10) receiving a single vaccination with 0.5 ml of the formalin-inactivated EEEV IND vaccine delivered by subcutaneous injection were challenged 4 weeks after the final vaccination with about $10^4$ PFU (~300 LD$_{50}$) of EEEV PE6 by the aerosol route. Kaplan-Meier survival analysis is shown indicating the percentage of surviving mice at each day of a 28-day post-challenge observation period.

FIGS. 16A and 16B are graphs summarizing the in vitro expression analysis in transfected cells. Radiolabeled lysates of COS-7 cells transiently transfected with 5 μg of empty vector, EEEV$_{WT}$, or EEEV$_{CO}$ DNA were immune precipitated with EEEV hyperimmune mouse ascitic fluids (HMAF) and analyzed by SDS-PAGE and phosphor imaging (FIG. 16A). COS-7 cells transiently transfected with 5-500 ng of empty vector, EEEV$_{WT}$, or EEEV$_{CO}$ DNA were permeabilized, stained with an EEEV E2- or E1-specific mouse mAb and a AlexaFluor488-labeled goat anti-mouse secondary antibody, and analyzed by flow cytometry. The mean percentage of cells positive for EEEV E2 and E1 (FIG. 16B) expression out of 10,000 events and the standard error of the means (SEM) are shown.

FIGS. 17A and 17B are graphs summarizing the antibody responses of vaccinated mice. Female BALB/c mice (N=6 per group) were vaccinated three times at 3-week intervals with 25 μg of empty vector DNA plasmid or 25, 5, or 1 μg of either the EEEV$_{WT}$ construct or the EEEV$_{CO}$ plasmid delivered by i.m. EP. Serum samples obtained 3 weeks after each vaccination were assayed for total IgG anti-VEEV antibodies by ELISA and for VEEV-neutralizing antibodies by PRNT. The mean log$_{10}$ ELISA (FIG. 17A) and PRNT$_{80}$ (FIG. 17B) titers along with the standard error of the mean (SEM) for each group are shown.

FIG. 19 is a graph showing the survival of vaccinated mice. Female BALB/c mice (N=10 per group) vaccinated twice at a 3-week interval with 5 μg of empty vector DNA or EEEV$_{CO}$ or 5 μg each of the EEEV$_{CO}$, VEEV$_{CO}$, and WEEV$_{CO}$ plasmids delivered by i.m. EP and positive control mice (N=10) receiving a single vaccination with 0.5 ml of the formalin-inactivated EEEV IND vaccine delivered by subcutaneous injection were challenged 4 weeks after the final vaccination with about $10^4$ PFU (~300 LD$_{50}$) of EEEV FL91-4679 by the aerosol route. Kaplan-Meier analysis is shown indicating the percentage of surviving mice at each day of a 28-day post-challenge observation period.

FIG. 20 shows the antibody responses of vaccinated rabbits. Female New Zealand White rabbits (N=5) were vaccinated with 500 μg of the EEEV$_{CO}$ plasmid or 500 μg each of the EEEV$_{CO}$, VEEV$_{CO}$, and WEEV$_{CO}$ plasmids delivered by i.m. EP on days 0, 28, and 230 (indicated by arrowheads). Serum samples obtained from the rabbits on days 0, 28, 42, 230, 266, and 349 were analyzed for EEEV-neutralizing antibodies by PRNT. The mean log$_{10}$ PRNT$_{80}$ titers along with the SEM for each group are shown.

FIG. 21 is a graph showing the antibody responses of vaccinated nonhuman primates. Adult cynomolgus macaques of both sexes (N=4 per group) were vaccinated with 500 μg of the empty vector DNA plasmid, 500 μg of the EEEV$_{CO}$ plasmid, or 500 μg each of the EEEV$_{CO}$, VEEV$_{CO}$, and WEEV$_{CO}$ plasmids delivered by i.m. EP at days 0, 28, and 56. Serum samples obtained from the macaques on days 0, 28, 56, and 84 were analyzed for EEEV-neutralizing antibodies by PRNT. The log$_{10}$ PRNT$_{80}$ titers are shown along with a bar representing the mean titer for each group.

FIG. 23A is a graph summarizing the antibody responses of vaccinated mice. Female BALB/c mice (N=10 per group) were vaccinated three times at a 3-week interval with 4 μg of empty vector DNA or WEEV$_{WT}$ plasmid or with 4 μg each of the WEEV$_{WT}$, VEEV$_{WT}$, and EEEV$_{WT}$ plasmids delivered by PMED. Positive control mice (N=10) each received a single vaccination with 0.5 ml of the formalin-inactivated WEEV IND vaccine delivered by subcutaneous injection. Serum samples obtained 3 weeks after each vaccination were assayed for total IgG anti-WEEV antibodies by ELISA, and the serum samples obtained 3 weeks after the last vaccination were also assayed for WEEV-neutralizing antibody responses by PRNT. The group mean log$_{10}$ ELISA and PRNT$_{80}$ titers along with the SEM are shown.

FIG. 23B is a graph showing the survival of vaccinated mice. Female BALB/c mice (N=10 per group) vaccinated three times at a 3-week interval with 4 μg of empty vector DNA or WEEV$_{WT}$ plasmid or with 4 μg each of the WEEV$_{WT}$, VEEV$_{WT}$, and EEEV$_{WT}$ plasmids delivered by PMED and positive control mice (N=10) receiving a single vaccination with 0.5 ml of the formalin-inactivated WEEV IND vaccine delivered by subcutaneous injection were challenged 4 weeks after the final vaccination with about $10^4$ PFU of WEEV CBA87 by the aerosol route. Kaplan-Meier survival analysis is shown indicating the percentage of surviving mice at each day of a 28-day post-challenge observation period.

FIG. 24 is a graph summarizing the in vitro expression analysis in transfected cells. Radiolabeled lysates of COS-7 cells transiently transfected with 5 μg of empty vector, WEEV$_{WT}$, or WEEV$_{CO}$ DNA were immune precipitated with WEEV hyperimmune mouse ascitic fluids (HMAF) and analyzed by SDS-PAGE and phosphor imaging.

FIGS. 25A and 25B are graphs summarizing the antibody responses of vaccinated mice. Female BALB/c mice (N=6 per group) were vaccinated three times at 3-week intervals with 25 μg of empty vector DNA plasmid or 25, 5, or 1 μg of either the WEEV$_{WT}$ construct or the WEEV$_{CO}$ plasmid delivered by i.m. EP. Serum samples obtained 3 weeks after each vaccination were assayed for total IgG anti-WEEV antibodies by ELISA and for WEEV-neutralizing antibodies by PRNT. The mean log$_{10}$ ELISA (FIG. 25A) and PRNT$_{80}$ (FIG. 25B) titers along with the standard error of the mean (SEM) for each group are shown.

FIGS. 26A and 26B are graphs summarizing the antibody responses of vaccinated mice. Female BALB/c mice (N=10 per group) were vaccinated twice at a 3-week interval with 5 μg of empty vector DNA or WEEV$_{CO}$ or 5 μg each of the WEEV$_{CO}$, VEEV$_{CO}$, and EEEV$_{CO}$ plasmids delivered by i.m. EP. Positive control mice (N=10) each received a single vaccination with 0.5 ml of the formalin-inactivated WEEV IND vaccine delivered by subcutaneous injection. Serum samples obtained 3 weeks after each vaccination were assayed for total IgG anti-WEEV antibodies by ELISA and for WEEV-neutralizing antibodies by PRNT. The mean log$_{10}$ ELISA (FIG. 26A) and PRNT$_{80}$ (FIG. 26B) titers along with the SEM for each group are shown.

FIG. 27 is a graph showing the survival of vaccinated mice. Female BALB/c mice (N=10 per group) vaccinated twice at a 3-week interval with 5 μg of empty vector DNA or WEEV$_{CO}$ or 5 μg each of the WEEV$_{CO}$, VEEV$_{CO}$, and EEEV$_{CO}$ plasmids delivered by i.m. EP and positive control mice (N=10) receiving a single vaccination with 0.5 ml of the formalin-inactivated WEEV IND vaccine delivered by subcutaneous injection were challenged 4 weeks after the final vaccination with about 10$^4$ PFU of WEEV CBA87 by the aerosol route. Kaplan-Meier survival analysis is shown indicating the percentage of surviving mice at each day of a 28-day post-challenge observation period.

FIG. 28 shows the antibody responses of vaccinated rabbits. Female New Zealand White rabbits (N=5) were vaccinated with 500 μg of the WEEV$_{CO}$ plasmid or 500 μg each of the WEEV$_{CO}$, VEEV$_{CO}$, and EEEV$_{CO}$ plasmids delivered by i.m. EP on days 0, 28, and 230 (indicated by arrowheads). Serum samples obtained from the rabbits on days 0, 28, 42, 230, 266, and 349 were analyzed for WEEV-neutralizing antibodies by PRNT. The mean log$_{10}$ PRNT$_{80}$ titers along with the SEM for each group are shown.

FIG. 29 is a graph showing the antibody responses of vaccinated nonhuman primates. Adult cynomolgus macaques of both sexes (N=4 per group) were vaccinated with 500 μg of the empty vector DNA plasmid, 500 μg of the WEEV$_{CO}$ plasmid, or 500 μg each of the WEEV$_{CO}$, VEEV$_{CO}$, and EEEV$_{CO}$ plasmids delivered by i.m. EP at days 0, 28, and 56. Serum samples obtained from the macaques on days 0, 28, 56, and 84 were analyzed for WEEV-neutralizing antibodies by PRNT. The log$_{10}$ PRNT$_{80}$ titers are shown along with a bar representing the mean titer for each group.

FIGS. 30A, 30B and 30C schematically show the VEEV$_{CO}$, EEEV$_{CO}$, and WEEV$_{CO}$ plasmids and their entire sequences, respectively, as exemplified in the experiments disclosed herein.

FIG. 31 shows the sequences of the plasmids exemplified in the experiments disclosed herein, where * represents the inserted EEV$_{CO}$ sequence such that: when * is VEEV$_{CO}$ (SEQ ID NO:1), the VEEV$_{CO}$ plasmid sequence is SEQ ID NO:7; when * is EEEV$_{CO}$ (SEQ ID NO:3), the EEEV$_{CO}$ plasmid sequence is SEQ ID NO:8; and when * is WEEV$_{CO}$ (SEQ ID NO:5), the WEEV$_{CO}$ plasmid sequence is SEQ ID NO:9. Although not provided in the sequence listing, it is noted that the sequences of the corresponding EEV$_{COCAP}$ plasmids merely contain the given EEV$_{COCAP}$ sequence where * is indicated.

DETAILED DESCRIPTION OF THE INVENTION

Figure 1:
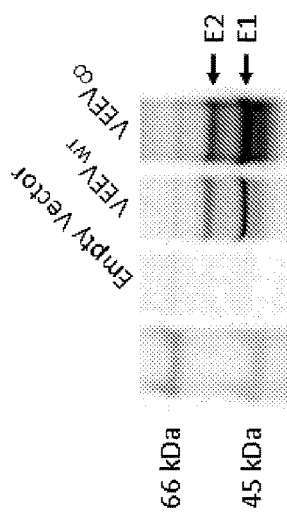
FIGS. 1 and 2 are graphs summarizing the in vitro expression analysis in transfected cells. Radiolabeled lysates of COS-7 cells transiently transfected with 5 μg of empty vector, VEEV$_{WT}$, or VEEV$_{CO}$ DNA were immune precipitated with VEEV IAB hyperimmune mouse ascitic fluids (HMAF) and analyzed by SDS-PAGE and phosphor imaging (FIG. 1). COS-7 cells transiently transfected with 5-250 ng of VEEV$_{WT}$, VEEV$_{CO}$, or VEEV$_{COCAP}$ DNA were permeabilized, stained with a VEEV E2- or E1-specific mouse mAb and a AlexaFluor488-labeled goat anti-mouse secondary antibody, and analyzed by flow cytometry. The mean percentage of cells positive for VEEV E2 and E1 (FIG. 2) expression out of 10,000 events and the standard error of the means (SEM) are shown.

The present invention provides nucleic acid molecules and constructs which may be used as vaccines against VEEV, EEEV, and/or WEEV, and compositions and methods for vaccinating subjects, such as human subjects, against VEEV, EEEV, and/or WEEV.

The nucleic acid molecules and constructs according to the present invention comprise codon-optimized sequences that encode structural proteins of EEVs and exclude sequences that encode the capsid proteins of EEVs.

A. VEEV

As exemplified herein, a wild-type VEEV DNA plasmid (VEEV$_{WT}$) was constructed by inserting the cloned 26S structural genes (C-E3-E2-6K-E1) of VEEV subtype IAB strain Trinidad donkey (Genbank accession number L01442) behind the cytomegalovirus immediate early promoter of the eukaryotic expression vector pWRG7077, as previously described. See Riemenschneider et al. (2003) Vaccine 21:4071-80, which is herein incorporated by reference. Codon optimized VEEV subtype IAB structural genes with the capsid gene (VEEV$_{COCAP}$) and lacking the capsid gene (VEEV$_{CO}$) were generated by subjecting the cloned wild type 26S structural genes (C-E3-E2-6K-E1) and the cloned wild type 26S structural genes lacking the capsid sequence (E3-E2-6K-E1), respectively, of VEEV subtype IAB strain Trinidad donkey (Genbank accession number L01442) to a GeneOptimizer™ bioinformatic algorithm (Geneart, Regensburg, Germany) for mammalian expression and then synthesized using methods known in the art. DNA plasmids were constructed by cloning the synthesized codon optimized genes into the NotI and BglII restriction sites of pWRG7077 using methods known in the art.

The sequences of the nucleic acid molecules are as follows:

VEEV$_{CO}$:
(SEQ ID NO: 1)
ATGAGCCTGGTGACCACCATGTGCCTGCTGGCCAACGTGACCTTCCCCTG

CGCCCAGCCCCCCATCTGCTACGACCGGAAGCCCGCCGAGACCCTGGCCA

TGCTGTCCGTGAACGTGGACAACCCCGGCTACGACGAGCTGCTGGAAGCC

GCCGTGAAGTGCCCCGGCAGGAAGCGGCGGAGCACCGAGGAACTGTTCAA

AGAGTACAAGCTGACCCGGCCCTACATGGCCCGGTGCATCAGATGCGCCG

TGGGCAGCTGCCACAGCCCCATCGCCATCGAGGCCGTGAAGAGCGACGGC

CACGACGGCTACGTGCGGCTGCAGACCAGCAGCCAGTACGGCCTGGACAG

CAGCGGCAACCTGAAGGGCCGGACCATGAGATACGACATGCACGGCACCA

TCAAAGAGATCCCCCTGCACCAGGTGTCCCTGCACACCAGCCGGCCCTGC

CACATCGTGGACGGCCACGGCTACTTTCTGCTGGCCAGGTGCCCTGCCGG

CGACAGCATCACCATGGAATTCAAGAAAGACAGCGTGACCCACAGCTGCA

GCGTGCCCTACGAGGTGAAGTTCAACCCCGTGGGCCGGGAGCTGTACACC

CACCCCCCCGAGCACGGCGTGGAGCAGGCCTGCCAGGTGTACGCCCACGA

CGCCCAGAACAGGGGCGCCTACGTGGAGATGCACCTGCCCGGCAGCGAGG

TGGACAGCTCCCTGGTGTCCCTGAGCGGCAGCAGCGTGACCGTGACCCCC

CCTGTGGGCACCAGCGCCCTGGTGGAGTGCGAGTGCGGCGGCACCAAGAT

CAGCGAGACCATCAACAAGACCAAGCAGTTCAGCCAGTGCACCAAGAAAG

AGCAGTGCCGGGCCTACCGGCTGCAGAACGACAAGTGGGTGTACAACAGC

GACAAGCTGCCCAAAGCCGCCGGAGCCACCCTGAAGGGCAAGCTGCACGT

GCCTTTTCTGCTGGCTGACGGCAAGTGCACCGTGCCCCTGGCCCCCGAGC

CCATGATCACCTTCGGCTTCAGAAGCGTGAGCCTGAAGCTGCACCCCAAG

AACCCCACCTACCTGACCACCCGGCAGCTGGCCGATGAGCCCCACTACAC

CCACGAGCTGATCAGCGAGCCCGCCGTGCGGAACTTCACCGTGACCGAGA

AGGGCTGGGAGTTCGTGTGGGGCAACCACCCCCCCAAGAGGTTCTGGGCT

CAGGAAACAGCCCCTGGCAACCCCCACGGCCTGCCTCACGAGGTGATCAC

CCACTACTACCACAGATACCCCATGAGCACCATCCTGGGCCTGAGCATCT

GCGCCGCCATCGCCACCGTGAGCGTGGCCGCCAGCACCTGGCTGTTCTGC

-continued

CGGTCCCGGGTGGCCTGCCTGACCCCCTACAGGCTGACCCCCAACGCCCG
GATCCCCTTCTGCCTGGCCGTGCTGTGCTGCGCCCGGACCGCCAGAGCCG
AGACCACCTGGGAGAGCCTGGACCACCTGTGGAACAACAACCAGCAGATG
TTCTGGATCCAGCTGCTGATCCCCCTGGCCGCCCTGATCGTGGTGACCCG
GCTGCTGAGATGCGTGTGCTGCGTGGTGCCCTTCCTGGTGATGGCCGGGG
CTGCAGGGGCCGGCGCCTATGAGCACGCCACCACCATGCCCAGCCAGGCC
GGCATCAGCTACAACACCATCGTGAACAGGGCCGGCTACGCCCCCCTGCC
CATCAGCATCACCCCTACCAAGATCAAGCTGATCCCCACCGTGAACCTGG
AATACGTGACCTGCCACTACAAGACCGGCATGGACAGCCCCGCCATCAAG
TGCTGCGGCAGCCAGGAATGCACCCCCACCTACAGGCCCGACGAGCAGTG
CAAGGTGTTCACCGGCGTGTACCCCTTCATGTGGGGCGGAGCCTACTGCT
TCTGCGACACCGAGAACACCCAGGTGTCCAAGGCCTACGTGATGAAGTCC
GACGATTGCCTGGCCGACCACGCCGAGGCCTACAAGGCCCACACCGCCAG
CGTGCAGGCCTTCCTGAACATCACCGTGGGCGAGCACAGCATCGTGACCA
CCGTGTACGTGAACGGCGAGACCCCCGTGAACTTCAACGGCGTGAAGCTG
ACCGCCGGACCCCTGAGCACCGCCTGGACCCCCTTCGACCGGAAGATCGT
GCAGTACGCCGGCGAAATCTACAACTACGACTTCCCCGAGTATGGCGCCG
GACAGCCTGGCGCCTTCGGCGACATCCAGAGCCGGACCGTGAGCAGCAGC
GACCTGTACGCCAACACCAACCTGGTGCTGCAGCGGCCCAAGGCCGGAGC
CATCCACGTGCCCTACACCCAGGCCCCCAGCGGCTTCGAGCAGTGGAAGA
AGGACAAGGCCCCCTCCCTGAAGTTCACCGCCCCCTTCGGCTGTGAAATC
TACACCAACCCCATCCGGGCCGAGAACTGTGCCGTGGGCTCCATCCCTCT
GGCCTTCGACATCCCCGACGCCCTGTTCACCAGAGTGTCCGAGACCCCCA
CCCTGTCTGCCGCCGAGTGCACCCTGAACGAGTGCGTCTACTCCTCTGAC
TTCGGCGGCATCGCCACAGTGAAGTACAGCGCCAGCAAGAGCGGCAAGTG
TGCCGTGCACGTGCCCAGCGGCACAGCCACACTGAAGGAAGCCGCCGTGG
AGCTGACCGAGCAGGGCAGCGCCACCATCCACTTCAGCACCGCCAACATC
CACCCCGAGTTCAGGCTGCAGATTTGCACCAGCTACGTGACATGCAAGGG
CGACTGCCACCCCCCTAAGGACCACATCGTGACCCACCCCCAGTACCACG
CCCAGACCTTCACAGCCGCCGTGTCCAAGACAGCCTGGACCTGGCTGACC
AGCCTGCTGGGCGGCAGCGCCGTGATCATCATCATCGGCCTGGTGCTGGC
CACCATCGTGGCCATGTACGTGCTGACCAACCAGAAACACAACTGATGA.
As used herein, a plasmid containing
SEQ ID NO: 1 is referred to as
"VEEV$_{CO}$ plasmid".

VEEV$_{COCAP}$:
(SEQ ID NO: 2)
ATGTTCCCATTCCAGCCCATGTACCCCATGCAGCCCATGCCCTACCGGAA
CCCCTTTGCCGCCCCTCGGAGGCCCTGGTTCCCCCGGACCGACCCCTTCC
TGGCCATGCAGGTGCAGGAACTGACCAGAAGCATGGCCAACCTGACCTTC
AAGCAGCGGCGGGACGCCCCTCCTGAGGGCCCCTCCGCCAAGAAGCCCAA
GAAAGAGGCCAGCCAGAAGCAGAAGGGCGGAGGGCAGGGCAAGAAGAAGA
AAAACCAGGGGAAGAAGAAAGCCAAGACCGGCCCTCCCAACCCCAAGGCC

-continued

CAGAACGGCAACAAGAAAAAGACCAACAAGAAGCCCGGCAAGCGGCAGCG
GATGGTGATGAAGCTGGAAAGCGACAAGACCTTCCCCATCATGCTGGAAG
GCAAGATCAACGGCTACGCCTGCGTGGTGGGCGGCAAGCTCTTTAGACCC
ATGCACGTGGAGGGCAAAATTGACAACGACGTGCTGGCCGCCCTGAAAAC
CAAGAAGGCCAGCAAGTACGACCTGGAATACGCCGACGTGCCCCAGAACA
TGCGGGCCGACACCTTCAAGTACACCCACGAGAAGCCCCAGGGCTACTAC
AGCTGGCACCACGGAGCCGTGCAGTACGAGAACGGCCGGTTCACCGTGCC
CAAGGGCGTCGGCGCCAAGGGCGACAGCGGCAGACCCATCCTGGACAACC
AGGGCCGGGTGGTGGCCATCGTGCTGGGCGGCGTGAACGAGGGCAGCCGG
ACCGCCCTGAGCGTGGTGATGTGGAACGAGAAGGGCGTGACCGTGAAGTA
CACCCCTGAGAACTGCGAGCAGTGGAGCCTGGTGACCACCATGTGCCTGC
TGGCCAACGTGACCTTCCCCTGCGCCCAGCCCCCCATCTGCTACGACCGG
AAGCCCGCCGAGACCCTGGCCATGCTGTCCGTGAACGTGGACAACCCCGG
CTACGACGAGCTGCTGGAAGCGCCGTGAAGTGCCCCGGCAGGAAGCGGC
GGAGCACCGAGGAACTGTTCAAAGAGTACAAGCTGACCCGGCCCTACATG
GCCCGGTGCATCAGATGCGCCGTGGGCAGCTGCCACAGCCCCATCGCCAT
CGAGGCCGTGAAGAGCGACGGCCACGACGGCTACGTGCGGCTGCAGACCA
GCAGCCAGTACGGCCTGGACAGCAGCGGCAACCTGAAGGGCCGGACCATG
AGATACGACATGCACGGCACCATCAAAGAGATCCCCCTGCACCAGGTGTC
CCTGCACACCAGCCGGCCCTGCCACATCGTGGACGGCCACGGCTACTTTC
TGCTGGCCAGGTGCCCTGCCGGCGACAGCATCACCATGGAATTCAAGAAA
GACAGCGTGACCCACAGCTGCAGCGTGCCCTACGAGGTGAAGTTCAACCC
CGTGGGCCGGGAGCTGTACACCCACCCCCCCGAGCACGGCGTGGAGCAGG
CCTGCCAGGTGTACGCCCACGACGCCCAGAACAGGGGCGCCTACGTGGAG
ATGCACCTGCCCGGCAGCGAGGTGGACAGCTCCCTGGTGTCCCTGAGCGG
CAGCAGCGTGACCGTGACCCCCCCTGTGGGCACCAGCGCCCTGGTGGAGT
GCGAGTGCGGCGGCACCAAGATCAGCGAGACCATCAACAAGACCAAGCAG
TTCAGCCAGTGCACCAAGAAAGAGCAGTGCCGGGCCTACCGGCTGCAGAA
CGACAAGTGGGTGTACAACAGCGACAAGCTGCCCAAAGCCGCCGGAGCCA
CCCTGAAGGGCAAGCTGCACGTGCCTTTTCTGCTGGCTGACGGCAAGTGC
ACCGTGCCCCTGGCCCCCGAGCCCATGATCACCTTCGGCTTCAGAAGCGT
GAGCCTGAAGCTGCACCCCAAGAACCCCACCTACCTGACCACCCGGCAGC
TGGCCGATGAGCCCCACTACACCCACGAGCTGATCAGCGAGCCCGCCGTG
CGGAACTTCACCGTGACCGAGAAGGGCTGGGAGTTCGTGTGGGGCAACCA
CCCCCCCAAGAGGTTCTGGGCTCAGGAAACAGCCCCTGGCAACCCCCACG
GCCTGCCTCACGAGGTGATCACCCACTACTACCACAGATACCCCATGAGC
ACCATCCTGGGCCTGAGCATCTGCGCCGCCATCGCCACCGTGAGCGTGGC
CGCCAGCACCTGGCTGTTCTGCCGGTCCCGGGTGGCCTGCCTGACCCCCT
ACAGGCTGACCCCCAACGCCCGGATCCCCTTCTGCCTGGCCGTGCTGTGC
TGCGCCCGGACCGCCAGAGCCGAGACCACCTGGGAGAGCCTGGACCACCT

```
-continued
GTGGAACAACAACCAGCAGATGTTCTGGATCCAGCTGCTGATCCCCTGG

CCGCCCTGATCGTGGTGACCCGGCTGCTGAGATGCGTGTGCTGCGTGGTG

CCCTTCCTGGTGATGGCCGGGGCTGCAGGGGCCGGCGCCTATGAGCACGC

CACCACCATGCCCAGCCAGGCCGGCATCAGCTACAACACCATCGTGAACA

GGGCCGGCTACGCCCCCCTGCCCATCAGCATCACCCCTACCAAGATCAAG

CTGATCCCCACCGTGAACCTGGAATACGTGACCTGCCACTACAAGACCGG

CATGGACAGCCCCGCCATCAAGTGCTGCGGCAGCCAGGAATGCACCCCCA

CCTACAGGCCCGACGAGCAGTGCAAGGTGTTCACCGGCGTGTACCCCTTC

ATGTGGGGCGGAGCCTACTGCTTCTGCGACACCGAGAACACCCAGGTGTC

CAAGGCCTACGTGATGAAGTCCGACGATTGCCTGGCCGACCACGCCGAGG

CCTACAAGGCCCACACCGCCAGCGTGCAGGCCTTCCTGAACATCACCGTG

GGCGAGCACAGCATCGTGACCACCGTGTACGTGAACGGCGAGACCCCCGT

GAACTTCAACGGCGTGAAGCTGACCGCCGGACCCCTGAGCACCGCCTGGA

CCCCCTTCGACCGGAAGATCGTGCAGTACGCCGGCGAAATCTACAACTAC

GACTTCCCCGAGTATGGCGCCGGACAGCCTGGCGCCTTCGGCGACATCCA

GAGCCGGACCGTGAGCAGCAGCGACCTGTACGCCAACACCAACCTGGTGC

TGCAGCGGCCCAAGGCCGGAGCCATCCACGTGCCCTACACCCAGGCCCCC

AGCGGCTTCGAGCAGTGGAAGAAGGACAAGGCCCCCTCCCTGAAGTTCAC

CGCCCCCTTCGGCTGTGAAATCTACACCAACCCCATCCGGGCCGAGAACT

GTGCCGTGGGCTCCATCCCTCTGGCCTTCGACATCCCCGACGCCCTGTTC

ACCAGAGTGTCCGAGACCCCCACCCTGTCTGCCGCCGAGTGCACCCTGAA

CGAGTGCGTCTACTCCTCTGACTTCGGCGGCATCGCCACAGTGAAGTACA

GCGCCAGCAAGAGCGGCAAGTGTGCCGTGCACGTGCCCAGCGGCACAGCC

ACACTGAAGGAAGCCGCCGTGGAGCTGACCGAGCAGGGCAGCGCCACCAT

CCACTTCAGCACCGCCAACATCCACCCCGAGTTCAGGCTGCAGATTTGCA

CCAGCTACGTGACATGCAAGGGCGACTGCCACCCCCCTAAGGACCACATC

GTGACCCACCCCCAGTACCACGCCCAGACCTTCACAGCCGCCGTGTCCAA

GACAGCCTGGACCTGGCTGACCAGCCTGCTGGGCGGCAGCGCCGTGATCA

TCATCATCGGCCTGGTGCTGGCCACCATCGTGGCCATGTACGTGCTGACC

AACCAGAAACACAACTGATGA.
As used herein, a plasmid containing
SEQ ID NO: 2 is referred to as
"VEEV_{COCAP} plasmid".
```

The live-attenuated VEEV vaccine, TC-83, was manufactured by the National Drug Company (Philadelphia, Pa.).

To evaluate the protective efficacy of $VEEV_{CO}$ (SEQ ID NO:1) as a DNA vaccine, an established and well-characterized aerosol challenge model of VEEV infection in cynomolgus macaques was used. See Pratt et al. (2003) Vaccine 21:3854-62; Pratt et al. (1998) Vaccine 16:1056-64; Reed et al. (2005) Vaccine 23:3139-47; and Reed et al. (2004) J Infect Dis 189:1013-7. Previously, it was found that cynomolgus macaques vaccinated with three doses of $VEEV_{WT}$ DNA delivered by PMED developed low levels of VEEV-neutralizing antibodies and were only partially protected from aerosol VEEV challenge. See Dupuy et al. (2010) Vaccine 28:7345-50. As disclosed herein, it was unexpectedly found that cynomolgus macaques receiving two EP vaccinations with a dose as low as 50 μg of $VEEV_{CO}$ plasmid developed increased VEEV-neutralizing antibody titers as compared to macaques receiving the $VEEV_{WT}$ plasmid by PMED. In addition, these macaques had no detectable serum viremia and had reduced febrile reactions, lymphopenia, and clinical signs of disease as compared to negative control macaques after aerosol VEEV challenge. The macaques vaccinated with the $VEEV_{CO}$ plasmid displayed no neurological signs of disease after challenge. Thus, the present invention provides a nucleic acid vaccine that, at relatively low doses, provides protection against viremia and manifestation of disease symptoms that is at least similar to that provided by TC-83 and C-84.

Methods

In Vitro Expression Analysis.

Transient transfection, radiolabeling, and immune precipitation were performed as described previously. See Schmaljohn et al. (1997) J Virol 71:9563-9. Briefly, COS-7 cells grown in complete DMEM (Invitrogen, Carlsbad, Calif.) in 25-cm² culture flasks at 37° C. with 5% $CO_2$ were transfected with 5 μg of the appropriate DNA plasmid by using FuGene 6 reagent (Roche Diagnostics, Indianapolis, Ind.) according to the manufacturer's recommendations. After 24 h, the cells were starved for 30 min in methionine- and cysteine-free medium and then radiolabeled for 4 hours in medium containing 200 μCi of Promix ([$^{35}$S]methionine and [$^{35}$S]cysteine; Amersham Biosciences, Piscataway, N.J.) per 25-cm² flask. Cell lysates were made using 4% Zwittergent (Calbiochem, San Diego, Calif.) buffer containing Complete Protease Inhibitor Cocktail (Roche), and the lysates were normalized for protein concentration by BCA protein assay (Pierce Biotechnology, Rockford, Ill.). Immune precipitation of 200 μl of labeled lysate was performed with 10 μl of VEEV IAB hyperimmune mouse ascitic fluids and 150 μl of Protein G-Sepharose (Sigma-Aldrich, St. Louis, Mo.). Reduced samples (25 μl each) were analyzed by SDS-PAGE on a 4-12% Bis-Tris gradient gel (Invitrogen) by using MOPS running buffer (Invitrogen) at 200 V. The gel was fixed, dried, and analyzed using a Cyclone phosphorimager and OptiQuant software (PerkinElmer, Waltham, Mass.).

Flow cytometry of transiently transfected cells was performed as described previously. See Badger et al. (2011) Vaccine 29:6728-35. Briefly, COS-7 cells were transfected with 5-250 ng of the appropriate DNA plasmid as described above. After 40 h, the cells were washed with PBS (Invitrogen) and detached by using trypsin-EDTA (Sigma-Aldrich). The detached cells were washed three times in 4° C. FACS buffer (2% FBS and 0.1% Sodium Azide in 1×PBS) and fixed by adding BD Cytofix buffer (Becton-Dickinson, Franklin Lakes, N.J.) and incubating at 4° C. for 15 min. The fixed cells were washed as described above and permeabilized by adding BD Perm/Wash buffer (Becton-Dickinson) and incubating at 4° C. for 15 min. The permeabilized cells were washed as described above and a 1:100 dilution of the 1A4A-1 VEEV E2-specific or the 3B2A9 E1-specific mouse monoclonal antibody (mAb) (kind gifts of Dr. John T. Roehrig, Centers for Disease Control, Fort Collins, Colo.) was added to the cells. After incubation at 4° C. for 30 min, the cells were washed as described above and a 1:400 dilution of AlexaFluor488-labeled goat anti-mouse secondary antibody (Invitrogen) was added to the cells. After incubation at 4° C. for 20 min, the stained cells were washed as described above and analyzed on a FACSCalibur flow cytometer (Becton-Dickinson) to determine the percentage of cells positive for VEEV E2 or E1 envelope glycoprotein expression per 10,000 events.

Animals and Vaccinations.

Female BALB/c mice (6-8 weeks old) were vaccinated with plasmid solutions, i.e. VEEV$_{CO}$ plasmid, VEEV$_{COCAP}$ plasmid, and VEEV$_{WT}$ plasmid, diluted to the appropriate concentration in calcium- and magnesium-free PBS (Invitrogen) by i.m. EP using the TriGrid™ Delivery System (TDS) (Ichor Medical Systems, San Diego, Calif.) as described previously. See Luxembourg et al. (2008) Vaccine 26:4025-33. Briefly, mice anesthetized with i.m. injection of a diluted acepromazine/ketamine/xylazine mixture or with isofluorane gas were injected into one tibialis anterior muscle with 20 µl of a plasmid solution using a ³⁄₁₀ cm³ U-100 insulin syringe (Becton-Dickinson) inserted into the center of a TriGrid™ electrode array with 2.5 mm electrode spacing. Injection of the plasmid solution was followed immediately by electrical stimulation at amplitude of 250 V/cm, and the total duration was 40 ms over a 400 ms interval. Some control vaccinations consisted of i.m. injection of the plasmid solutions as described above without the application of electrical stimulation. The live-attenuated VEEV IND vaccine TC-83 was delivered by subcutaneous injection.

Female New Zealand White rabbits (3-3.5 kg) were anesthetized with isofluorane gas and vaccinated with the plasmid solutions diluted to the appropriate concentration by i.m. EP with the Ichor TDS essentially as described above for mice. However, rabbits were injected with 0.5 ml of plasmid solution into one quadriceps muscle with a 1-cm³ syringe (Becton-Dickinson) with a 23-gauge needle, and a TriGrid electrode array with 6.0-mm electrode spacing was used.

Healthy adult male cynomolgus macaques (≥5 kg) obtained from the nonhuman primate colony at USAMRIID lacking serum neutralizing antibodies against VEEV subtype IAB, VEEV subtype IE, VEEV subtype IIIA, and EEEV and WEEV as determined by plaque reduction neutralization tests (PRNT) (as described herein) were anesthetized by i.m. injection of Telazol and vaccinated with plasmid solution diluted to the appropriate concentration by i.m. EP with the Ichor TDS as described above for rabbits.

All animal research was conducted in compliance with the Animal Welfare Act and other federal statutes and regulations relating to animals and experiments involving animals and adheres to principles stated in the "Guide for the Care and Use of Laboratory Animals," Institute of Laboratory Animal Resources, Commission on Life Sciences, National Research Council, National Academy Press, Washington, D.C., 1996. The USAMRIID facility where this animal research was conducted is fully accredited by the Association for the Assessment and Accreditation of Laboratory Animal Care International.

Immunological Assays.

At various times after vaccination, blood samples were collected from anesthetized mice by retro-orbital bleed, from anesthetized rabbits by central auricular artery bleed, and from anesthetized macaques by femoral vein bleed, and serum was recovered by centrifugation. Total IgG anti-VEEV endpoint antibody titers were determined for serum samples by standard ELISA using sucrose-purified, irradiated whole VEEV IAB antigen as described previously. See Hodgson et al. (1999) Vaccine 17:1151-60. Briefly, two-fold serial dilutions of sera starting at 1:100 were incubated with 250 ng per well of antigen in 96-well plates. Horseradish Peroxidase (HRP)-conjugated anti-mouse IgG or anti-rabbit IgG secondary antibodies (Sigma-Aldrich) and ABTS peroxidase substrate (KPL, Gaithersburg, Md.) were used for detection. For antibody isotyping ELISA, HRP-conjugated anti-mouse IgG1 and anti-mouse IgG2a secondary antibodies (Bethyl Laboratories, Montgomery, Tex.) were used. The optical density at 405 nm was determined using a SpectraMax M2e microplate reader (Molecular Devices, Sunnyvale, Calif.) and the endpoint titers were calculated using Softmax Pro v5 (Molecular Devices).

The VEEV IAB-neutralizing antibody titers were determined for serum samples by PRNT as described previously. See Hodgson (1999). Briefly, two-fold serial dilutions of sera were mixed with equal volumes of medium containing 200 PFU of virus and incubated for 24 hours at 4° C. The virus/antibody mixtures were then used to infect confluent monolayers of Vero cells contained in six-well plates for 1 hour at 37° C. after which an overlay consisting of 0.6% agar in complete EBME (Invitrogen) without phenol red was added. The plates were stained 24 hours later by the addition of an overlay containing 5% neutral red and 0.6% agar in complete EBME without phenol red, and the plaques were counted 24 hours after staining. The antibody titers required for 80% reduction in the number of plaques (PRNT$_{80}$) were then calculated for each serum sample.

Anti-VEEV cellular immune responses were analyzed by IFN-γ ELISPOT assay using standard methods as described previously. See Taguchi et al. (1990) J Immunol Methods 128:65-73. Briefly, splenocytes isolated from individual spleens obtained from vaccinated mice using BD Falcon 100 µM nylon cell strainers (Becton-Dickinson) were resuspended in complete RPMI 1640 medium (Mediatech, Manassas, Va.). The resuspended splenocytes from each spleen were then added at a concentration of 2×10⁵ cells per well to triplicate wells of MultiScreen$_{HTS}$ IP 0.45 µm PVDF filter 96-well plates (Millipore, Billerica, Mass.) previously coated with mouse IFN-γ ELISPOT capture antibody (Becton-Dickinson). The splenocytes were then cultured with no peptide, 10 µg/ml of Concanavalin A (Sigma-Aldrich), 20 µg/ml of β-galactosidase peptide TPHPARIGL (New England Peptide, Gardner, Mass.), or 10 µg/ml of pooled 15-mer peptides with an 11-base overlap spanning the VEEV IAB E2 or E1 envelope glycoprotein (Pepscan, Lelystad, The Netherlands) for 24 hours at 37° C. with 5% CO$_2$. Secreted IFN-γ was detected by aspirating the cell suspension and successively incubating the plate for 2 hour at room temperature with mouse IFN-γ ELISPOT detection antibody (Becton-Dickinson), for 1 hour at room temperature with streptavidin-HRP (Becton-Dickinson), and for 20 minutes at room temperature with AEC substrate (Becton-Dickinson). The substrate reaction was then stopped by washing the plates with deionized H$_2$O, the plates were dried for 2 hours at room temperature, and the spots were enumerated.

Aerosol Challenge of Mice.

Mice were placed into a Class III biological safety cabinet located inside a biosafety level-3 containment suite and exposed in a whole-body aerosol chamber to a VEEV aerosol created by a Collison nebulizer for 10 minutes as previously described. See Hart et al. (1997) Vaccine 15:363-9. VEEV subtype IAB (strain Trinidad donkey) was diluted to an appropriate starting concentration in Hank's balanced salt solution (HBSS) containing 1% fetal bovine serum for use in aerosol generation. Samples collected from the all-glass impinger (AGI) attached to the aerosol chamber were analyzed by plaque assay on Vero cells using standard methods as previously described to determine the inhaled dose of VEEV. See Pratt et al. (1998) Vaccine 16:1056-64. The mice were monitored twice daily for clinical signs of illness and death for 28 days post-challenge and any moribund animals were euthanized. After the post-challenge observation period was completed, Kaplan-Meier survival analysis of the protection data was performed.

Aerosol Challenge of Macaques.

Before aerosol exposure, macaques were anesthetized by i.m. injection of 6 mg/kg of Telazol and a whole-body plethysmograph was taken for 3 minutes to determine the respiratory capacity of the animal. The macaques were then inserted into a Class III biological safety cabinet located inside a biosafety level-3 containment suite and exposed in a head-only aerosol chamber to a VEEV aerosol created by a Collison nebulizer for 10 minutes as previously described. See Pratt (1998) and Reed et al. (2004) J Infect Dis 189: 1013-7. VEEV IAB (strain Trinidad donkey) was diluted to an appropriate starting concentration in HBSS containing 1% fetal bovine serum for use in aerosol generation. Samples collected from the all-glass impinger (AGI) attached to the aerosol chamber were analyzed by plaque assay on Vero cells using standard methods as described above to determine the inhaled dose of VEEV. The macaques were monitored at least twice daily for clinical signs of illness for 28 days post-challenge. The macaques were observed for neurological signs of infection, changes in activity and behavior, and response to stimuli using predetermined criteria. The observers were blinded and were not aware of which macaques belonged to which groups.

On days −3 to −1 relative to aerosol exposure and for 7 days post-challenge, the macaques were anesthetized with 3 mg/kg of Telazol and blood samples were collected to assess viremia and lymphopenia. Serum viremia was measured by plaque assay as described above. Complete blood counts were determined with a Coulter T-series instrument (Beckman Coulter, Brea, Calif.) and a manual differential count. TA10TA-D70 radiotelemetry implants (Data Sciences International, St. Paul, Minn.) were surgically implanted subcutaneously on the dorsal surface and macaques were allowed ≥30 days to recover from surgery and to acclimate before VEEV exposure. Body temperatures were recorded every 15 minutes by using the DataQuest A.R.T. 2.1 System (Data Sciences International). Temperature monitoring was initiated 14 days before VEEV exposure to develop baseline temperature data to fit an autoregressive integrated moving average (ARIMA) model, as previously described. See Pratt (1998) and Reed (2004). Forecasted values for the post-challenge time periods were based on the training model extrapolated forward in time. Residual temperature changes after exposure were determined by subtracting the predicted temperature from the actual temperature recorded for each point.

Statistical Analysis.

$Log_{10}$ transformations were applied to whole-virus ELISA titers and $PRNT_{80}$ titers. Mixed model analysis of variance (ANOVA) with Tukey's post hoc tests was used to compare titers between groups at each time point. Kaplan Meier survival analysis was performed for the mouse challenge study data, with log rank tests used for comparison of survival curves. The effects of whole-virus ELISA titers and $PRNT_{80}$ titers on the probability of survival were assessed using a backwards-selection logistic regression model. Analyses were conducted using SAS v9.2 (SAS Institute, Cary, N.C.).

Results

Figure 2:
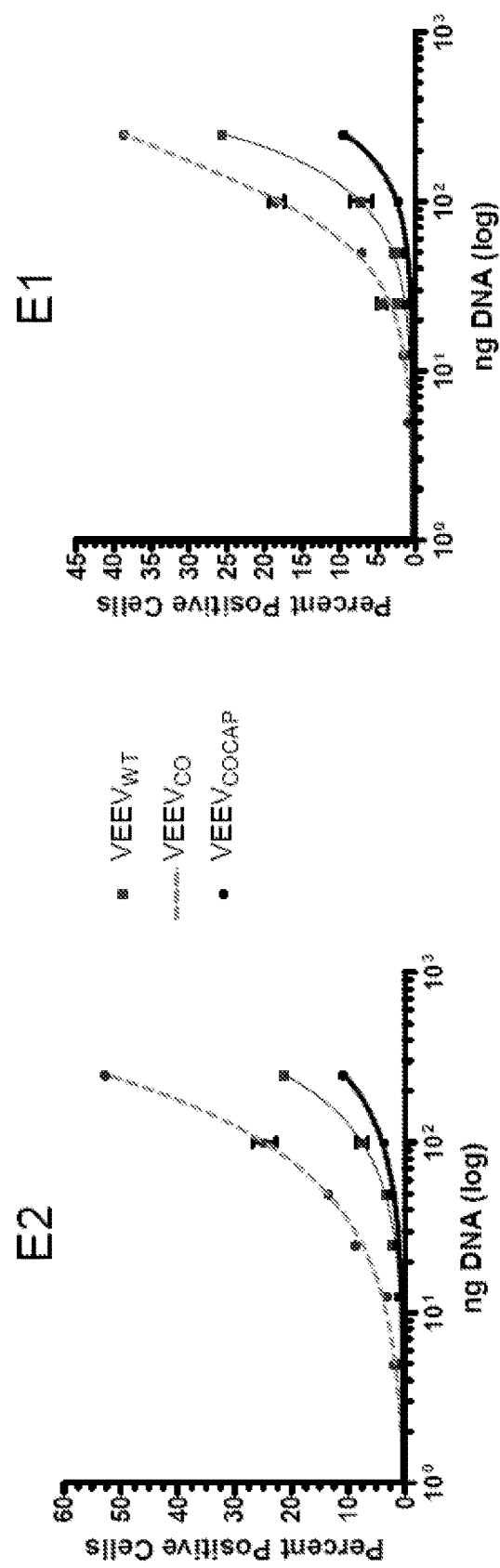

In Vitro Expression Analysis. To determine if the $VEEV_{CO}$ vaccine construct showed improved expression of the envelope glycoproteins as compared to the previous $VEEV_{WT}$ construct, the proteins expressed in transiently transfected mammalian cells were detected by immune precipitation assay. The expression of the E2 and E1 envelope glycoproteins from the $VEEV_{CO}$ DNA was increased approximately fivefold relative to that of the $VEEV_{WT}$ construct in this assay (FIG. 1). To further quantify the relative in vitro expression levels of these constructs, the percent of cells positive for E2 and E1 expression after transient transfection of 5-250 ng of each DNA vaccine plasmid was determined by flow cytometry. In this assay, the potential impact of codon optimization of the capsid protein was also examined by including the $VEEV_{COCAP}$ plasmid. A significant increase in the mean percent of cells positive for E2 and E1 expression was observed for the $VEEV_{CO}$ DNA plasmid at all concentrations except for the 5-ng sample for both E2 and E1 and for the 25-ng sample for E1 ($p<0.05$) (FIG. 2). It was unexpectedly found that the percentage of cells positive for E2 and E1 expression were lower for $VEEV_{COCAP}$ as compared to $VEEV_{WT}$ for the 50-250 ng samples.

Immunogenicity in Mice.

To determine whether i.m. EP delivery is an effective mode of administration for the $VEEV_{CO}$ plasmid, groups of six female BALB/c mice were vaccinated by i.m. EP three times at 3-week intervals with 25 μg, 5 μg, or 1 μg of the $VEEV_{CO}$ plasmid, or for comparison, with the vaccine used in our earlier studies, which expresses the capsid gene as well as the envelope protein genes of wild-type VEEV ($VEEV_{WT}$). A negative control group received the plasmid vector with no insert.

Graphs summarizing the antibody responses of vaccinated mice were generated. Female BALB/c mice (N=6 per group) were vaccinated three times at 3-week intervals with 25 μg of empty vector DNA plasmid or 25, 5, or 1 μg of either the $VEEV_{WT}$ construct or the $VEEV_{co}$ plasmid delivered by i.m. EP. Serum samples obtained 3 weeks after each vaccination were assayed for total IgG anti-VEEV antibodies by ELISA and for VEEV-neutralizing antibodies by PRNT. The group mean $log_{10}$ ELISA and $PRNT_{80}$ titers along with the standard error of the mean (SEM) were determined. *$p<0.05$, *$p<0.005$, and ***$p<0.0001$ for comparison between titers for $VEEV_{CO}$ and $VEEV_{WT}$.

Serum samples obtained 3 weeks after each vaccination were assayed for total anti-VEEV IgG antibodies by ELISA and for VEEV-neutralizing antibodies by PRNT. The mean ELISA titers of mice vaccinated with the $VEEV_{CO}$ plasmid were significantly higher than those of mice vaccinated with the $VEEV_{WT}$ construct for the 5 μg dose groups after a single vaccination and for the 1 μg dose groups after each of the three vaccinations (data not shown). After two or three vaccinations with the 5 μg dose and after each of the three vaccinations with the 25 μg dose, the mice receiving these two plasmids displayed similar mean ELISA titers ($p>0.05$). Within each group, there was no significant increase in the mean titers observed after two or three vaccinations.

The mean $PRNT_{80}$ titer elicited by mice vaccinated with the $VEEV_{CO}$ plasmid was significantly higher than that observed for mice vaccinated with the $VEEV_{WT}$ construct for all dose groups at all days ($p<0.01$-$0.0001$) (data not shown). Interestingly, the mean $PRNT_{80}$ titer of mice vaccinated with 1 μg of the $VEEV_{CO}$ plasmid was higher than that of mice receiving 25 μg of the $VEEV_{WT}$ construct after each of the three vaccinations. As observed for the total IgG antibody titers, there was only a small difference in the level of antibodies measured by PRNT after two or three vaccinations.

Figures 3A, 3B:
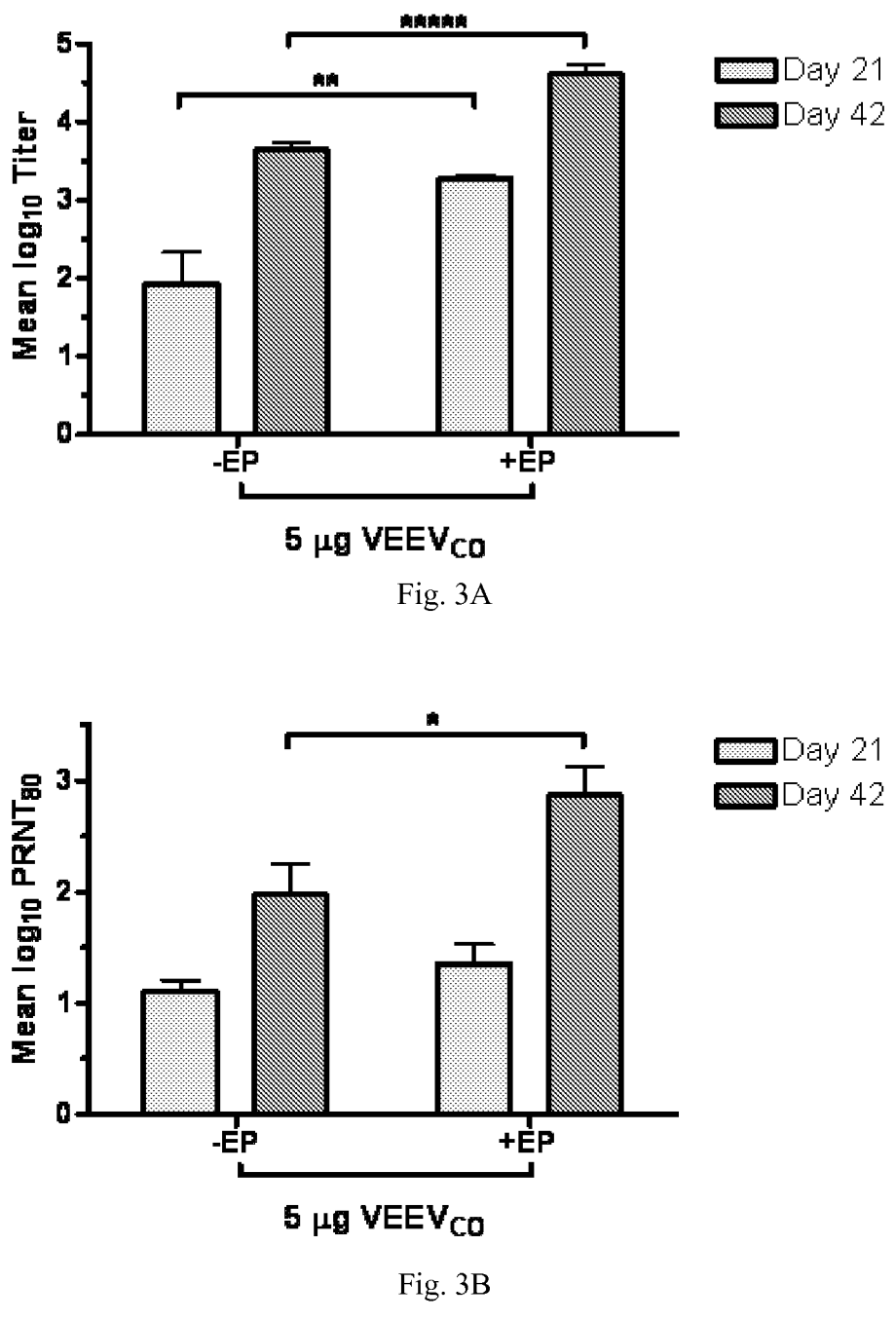

To directly assess the effect of EP, a separate experiment was conducted in which groups of six female BALB/c mice were vaccinated twice at a 3-week interval with 5 μg of the $VEEV_{CO}$ plasmid delivered by i.m. injection with and without EP. After the second vaccination, both the mean ELISA (FIG. 3A) and PRNT (FIG. 3B) antibody titers were significantly higher in mice receiving the vaccine with EP as compared to those receiving it by injection only.

$VEEV_{CO}$ vs. $VEEV_{COCAP}$: As a first step toward assessing the protective efficacy of the $VEEV_{CO}$ plasmid delivered by i.m. EP, a challenge study was performed in mice. In this study, the potential contribution of the capsid protein was also examined by including a codon optimized construct expressing all of the structural proteins of VEEV including capsid ($VEEV_{COCAP}$ plasmid). Groups of 10 female BALB/c mice were vaccinated twice at a 3-week interval with 5 µg of these codon optimized plasmid or with 5 µg of empty vector by i.m. EP. A positive control group was also included in this experiment in which the mice were given a single subcutaneous injection of the live-attenuated VEEV IND vaccine, TC-83 ($1 \times 10^4$ PFU).

Figures 4A, 4B:
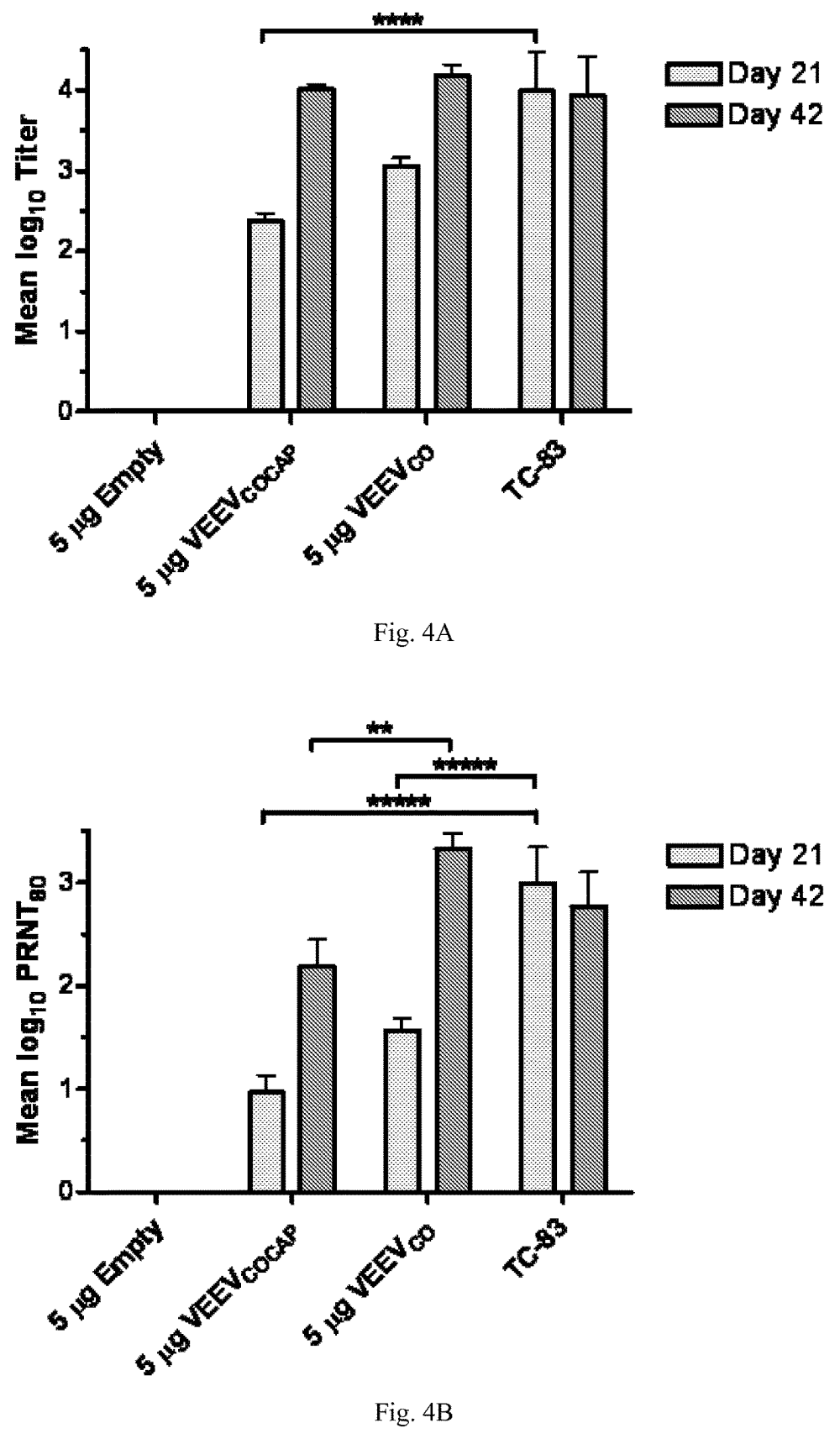

There was no statistical difference in the mean ELISA titers observed for serum samples collected 3 weeks after one or two vaccinations with the $VEEV_{CO}$ plasmid or $VEEV_{COCAP}$ plasmid; however, for both of these groups, the second vaccination significantly boosted the antibody titer as compared to that measured after one vaccination (FIG. 4A). Comparing the overall antibody responses elicited by the $VEEV_{CO}$ plasmid and the $VEEV_{COCAP}$ plasmid to that resulting from vaccination TC-83 revealed that the $VEEV_{CO}$ plasmid and TC-83 elicited similar titers after a single vaccination, whereas two vaccinations with the $VEEV_{COCAP}$ plasmid were required to match that obtained with TC-83. While the mean neutralizing antibody titers of mice receiving two vaccinations with the $VEEV_{CO}$ plasmid were similar to those of mice vaccinated with TC-83, those of mice receiving two vaccinations with the $VEEV_{COCAP}$ plasmid remained significantly lower than those vaccinated with TC-83 (FIG. 4B).

Figure 5:
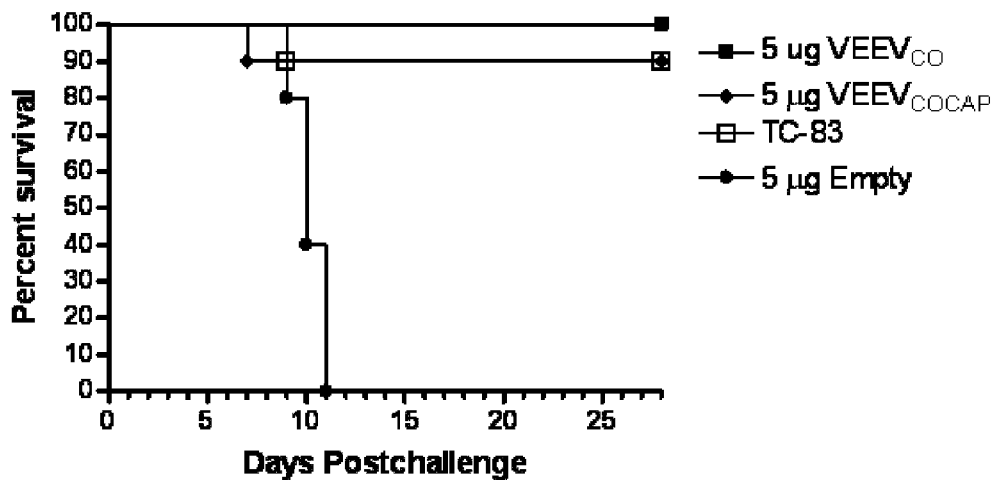
FIG. 5 is a graph showing the survival of vaccinated mice. Female BALB/c mice (N=10 per group) vaccinated twice at a 3-week interval with 5 μg of empty vector DNA, VEEV$_{COCAP}$, or VEEV$_{CO}$ plasmid delivered by i.m. EP and positive control mice (N=10) receiving a single vaccination with 0.5 ml of the live-attenuated VEEV IND vaccine TC-83 ($1\times10^4$ PFU) delivered by subcutaneous injection were challenged 4 weeks after the final vaccination with about $10^4$ PFU ($\geq1,000$ LD$_{50}$) of VEEV IAB by the aerosol route. Kaplan-Meier survival analysis is shown indicating the percentage of surviving mice at each day of a 28-day post-challenge observation period.

To assess vaccine efficacy, the mice from all groups were challenged four weeks after the final vaccination with about $10^4$ PFU ($\geq 1,000$ $LD_{50}$) of VEEV IAB strain Trinidad donkey administered by the aerosol route. Control mice, which were vaccinated with the empty vector, all displayed signs of illness after challenge including ruffled fur, loss of appetite, inactivity, and hunched backs, and all died or were euthanized due to morbidity (FIG. 5). Consistent with results from previous aerosol challenge studies (Dupuy et al. (2009) Vaccine 27:4152-60; and Riemenschneider et al. (2003) Vaccine 21:4071-80), 90% of the mice receiving TC-83 survived the challenge, and the single mouse that did not survive the challenge did not respond to the vaccine and had no detectable VEEV-neutralizing antibody response after vaccination. Likewise, one mouse in the group receiving the $VEEV_{COCAP}$ plasmid did not develop a detectable VEEV-neutralizing antibody response and died after challenge. All mice vaccinated with the $VEEV_{CO}$ plasmid developed neutralizing antibodies to VEEV, showed no signs of illness, and survived the challenge. Of note, mice receiving only a single vaccination with 5 µg of the $VEEV_{CO}$ plasmid were also completely protected from aerosol VEEV challenge (data not shown).

Cell-Mediated Immune Responses of Vaccinated Mice.

Figure 6A:
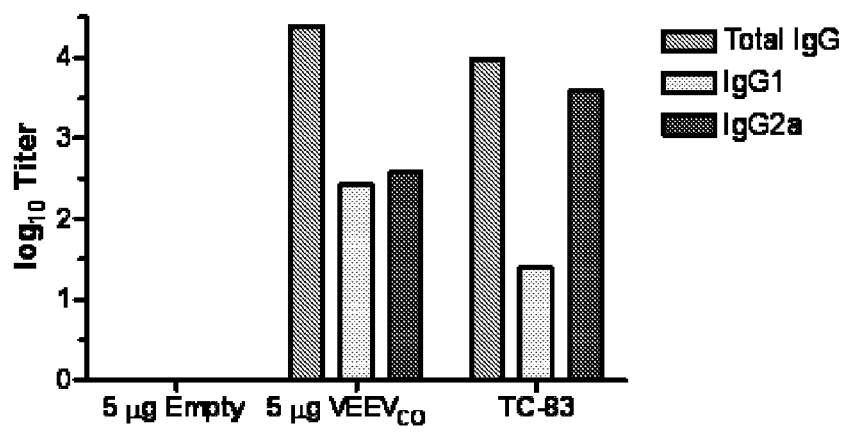
FIGS. 6A and 6B are graphs showing the cellular immune responses of vaccinated mice. Pooled sera obtained on day 42 from mice vaccinated with empty vector DNA, VEEV$_{CO}$ plasmid, and TC-83 from the challenge study were assayed for total IgG, IgG1, and IgG2 anti-VEEV antibodies by ELISA and the titers are shown (FIG. 6A). Female BALB/c mice (N=6 per group) were vaccinated twice at a 3-week interval with 5 μg of empty vector or VEEV$_{CO}$ plasmid delivered by i.m. EP. Two weeks after the second vaccination, splenocytes were isolated and restimulated with no peptide, Concanavalin A, pools of overlapping peptides representing the unrelated β-Galactosidase protein, or pools of overlapping peptides representing the VEEV IAB E2 or E1 envelope glycoproteins and analyzed by IFN-γ ELISpot. The group mean spot forming units (SFU) per $10^6$ cells along with the SEM are shown (FIG. 6B). *$p<0.05$ for comparison between IFN-γ responses for VEEV E2 and E1 peptide pools.

Although the most widely accepted correlate of protective immunity against VEEV is antibody responses directed against the envelope glycoproteins (Bennett et al. (2000) Vaccine 19:337-47; Hart et al. (2001) Vaccine 20:616-22; and Phillpotts et al. (2002) Vaccine 20:1497-504), recent studies have indicated a possible role for certain populations of T-lymphocytes in protection against VEEV in mice. See Brooke et al. (2010) J Virol 84:4556-68; Jones et al. (2003) Virus Res 91:255-9; Paessler et al. (2007) Virology 367: 307-23; and Yun et al. (2009) Vaccine 27:4064-73. Thus, as an indirect measure of the ability of the $VEEV_{CO}$ plasmid to elicit cell mediated immune responses, IgG antibody subtypes in pooled sera obtained from mice in the challenge study after their second vaccination was assayed. Mice vaccinated with TC-83 had a preponderance of IgG2a antibodies associated with a predicted Th1 skew in immune response (FIG. 6A). In contrast, mice vaccinated with the $VEEV_{CO}$ plasmid delivered by i.m. EP had comparable IgG1 and IgG2a antibody titers indicative of a more balanced Th1/Th2 immune response.

Figure 6B:
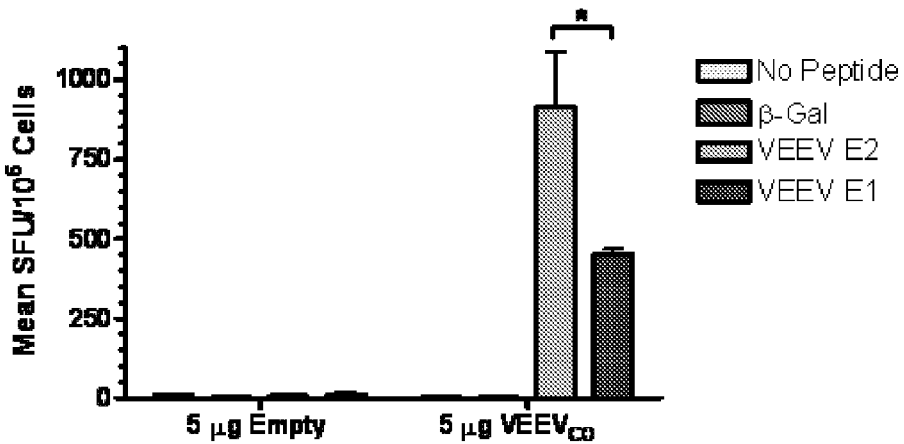

To directly evaluate the possibility that the $VEEV_{CO}$ plasmid could elicit cell-mediated immune responses, groups of female BALB/c mice (N=6) were vaccinated twice at a 3-week interval 5 µg of empty vector or $VEEV_{CO}$ plasmid delivered by i.m. EP. Two weeks after the second vaccination, splenocytes isolated from the vaccinated mice were restimulated with no peptide, Concanavalin A, a β-galactosidase control peptide, or pools of overlapping peptides spanning the VEEV IAB E2 or E1 envelope glycoproteins and analyzed by IFN-γ ELISPOT. Splenocytes restimulated with Concanavalin A produced a number of spots that were too numerous to count (data not shown). Although splenocytes restimulated with no peptide or with the β-galactosidase peptide failed to produce a response in this assay, those restimulated with pooled peptides representing the VEEV E2 or E1 protein produced measurable IFN-γ responses (FIG. 6B). Interestingly, the mean IFN-γ response of splenocytes restimulated with the VEEV E2 pooled peptides was significantly higher than that of those restimulated with the VEEV E1 pooled peptides.

Durability of the Antibody Response to $VEEV_{CO}$ in Rabbits.

Figures 7, 8:
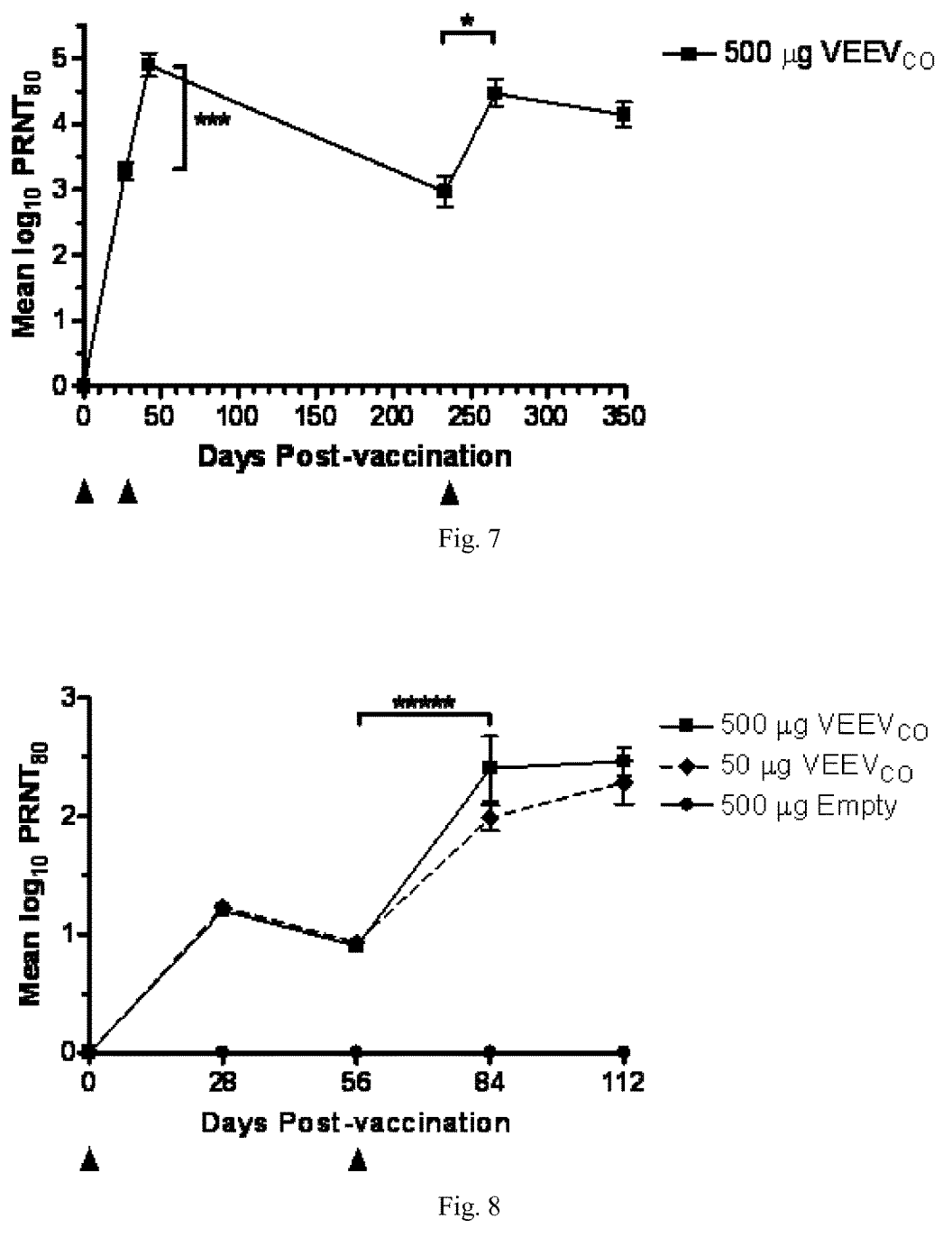

Although rabbits are not traditionally used as a challenge model for VEEV, their large muscle size permits EP delivery of higher doses of DNA plasmids that are similar to those expected to be delivered to humans. Thus, rabbits are a useful model for studying antibody durability after vaccination. To assess the durability of the antibody response to $VEEV_{CO}$, 5 female New Zealand White rabbits were vaccinated with 500 µg of the $VEEV_{CO}$ plasmid delivered by i.m. EP on days 0, 28, and 230, and their antibody responses to VEEV were measured on days 0, 28, 42, 230, 266, and 349 by PRNT. The rabbits produced high titers of VEEV-neutralizing antibodies after a single vaccination with the $VEEV_{CO}$ DNA construct and upon receiving a second vaccination, their mean $PRNT_{80}$ titer was significantly boosted (FIG. 7). The $PRNT_{80}$ titer declined between days 42 and 230, yet remained remarkably high, with a mean titer of 1:1,000 at day 230. In addition, the mean $PRNT_{80}$ titer was significantly boosted with an additional DNA vaccination performed on day 230, and the level of VEEV-neutralizing antibodies observed on day 266 was not significantly different from that observed on day 42.

Immunogenicity and Protective Efficacy of the $VEEV_{CO}$ Plasmid in Cynomolgus Macaques.

The immunogenicity and protective efficacy of the $VEEV_{CO}$ plasmid was assessed using an established model of VEEV infection of nonhuman primates that has been refined by the use of telemetry to evaluate fever responses. See Pratt et al. (1998) Vaccine 16:1056-64. Groups of four adult male cynomolgus macaques were vaccinated by i.m. EP with each animal receiving 500 µg of the empty vector DNA plasmid or 500 µg or 50 µg of the $VEEV_{CO}$ plasmid at days 0 and 56. Neutralizing antibodies were detected in all of the macaques after a single vaccination with either dose of the VEEV$_{CO}$ plasmid, and a second vaccination significantly boosted the mean PRNT$_{80}$ titers (FIG. 8). In addition, the mean PRNT$_{80}$ titers were not significantly different between the 500-μg and 50-μg dose groups at any of the time points.

Figures 9A, 9B, 9C:
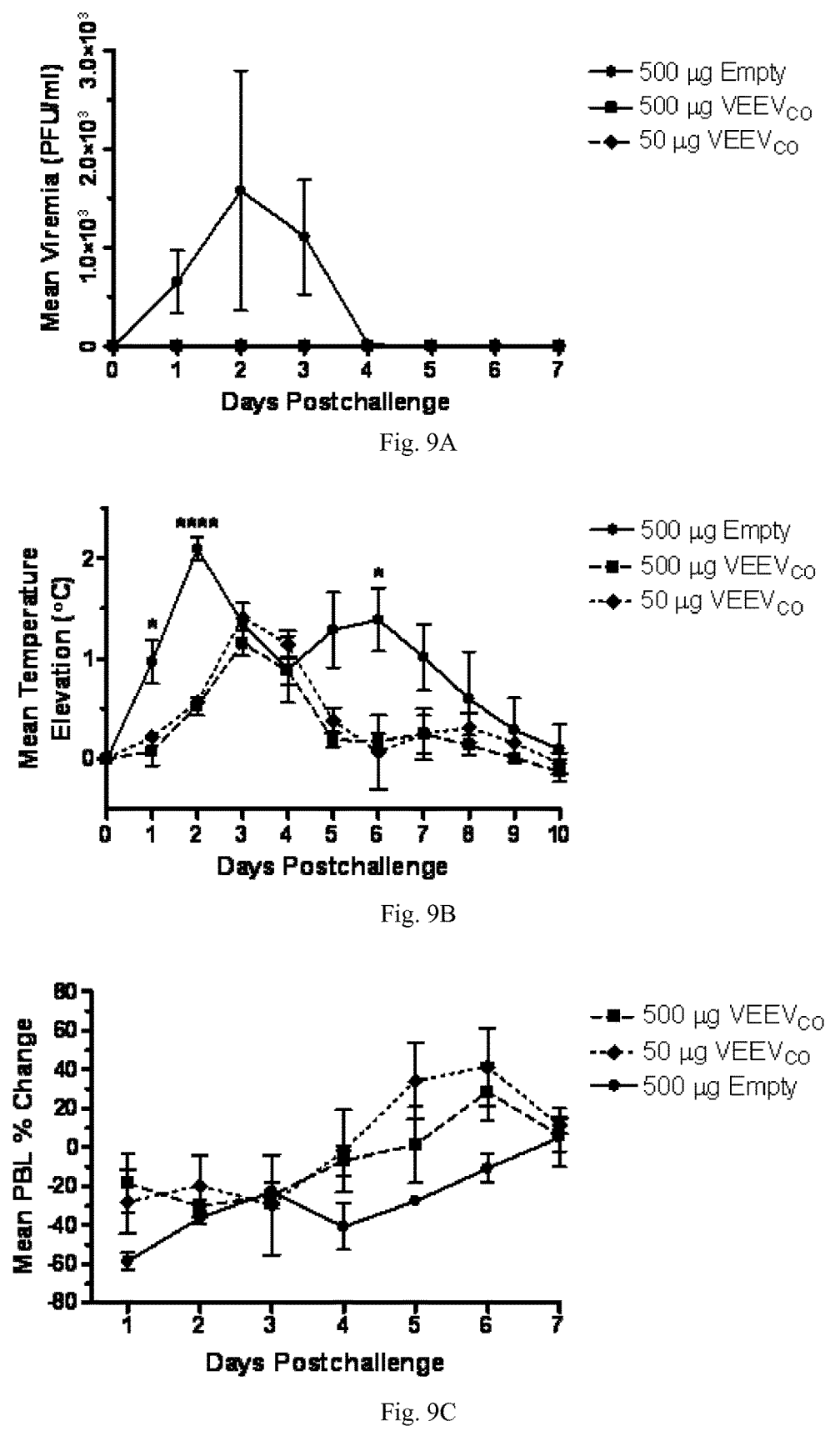

On day 112, the macaques were challenged with VEEV IAB, strain Trinidad donkey, administered by the aerosol route, and the average inhaled dose was calculated to be 3×10$^8$ PFU or about 300 median effective doses (ED$_{50}$). Serum viremia was detected in macaques vaccinated with control empty vector on day 1, peaked on day 2 with a mean group titer of 1,576 PFU/ml, and persisted for 4 days post-challenge (FIG. 9A). In contrast, the macaques receiving either dose of the VEEV$_{CO}$ plasmid were aviremic in all post-challenge serum samples tested.

The protective efficacy of the vaccine was also assessed by telemetry monitoring of the post-challenge fever responses. Macaques vaccinated with the empty vector DNA developed high biphasic fevers that appeared within 24 hours of VEEV challenge and had peaks at days 2 and 6 post-challenge (FIG. 9B). Macaques receiving either 500 μg or 50 μg of the VEEV$_{CO}$ plasmid also developed fevers after VEEV aerosol challenge, but these peaked at day 3 post-challenge and the mean temperature elevations were significantly lower than those of macaques receiving the empty vector DNA at day 1 ($p<0.05$), day 2 ($p\leq0.0001$), and day 6 ($p<0.05$). In addition, there was no significant difference in the mean temperature elevations of macaques receiving the 500 μg or 50 μg dose of the VEEV$_{CO}$ plasmid at any time ($p>0.05$).

To monitor lymphopenia, peripheral blood lymphocyte (PBL) counts determined for post-challenge blood samples collected from all macaques on days 1 to 7 after VEEV challenge were compared to average baseline counts determined for pre-challenge blood samples collected on days $-3$ to $-1$. The PBL counts of macaques vaccinated with the empty-vector DNA plasmid dropped an average of 58.6% from baseline within 24 hours of VEEV exposure and these macaques remained lymphopenic for an average of 6 days post-challenge (FIG. 9C). In contrast, the PBL counts of macaques vaccinated with 500 μg or 50 μg of the VEEV$_{CO}$ plasmid dropped an average of 18.5% and 28.1% from baseline, respectively, at 24 hours after challenge and this lymphopenia averaged 3 days for both groups. Over the entire 7 day post-challenge observation period, the macaques vaccinated with the empty-vector DNA developed a lymphopenia that was characterized by an average change of $-27.5\%$ from baseline PBL counts, while that of macaques vaccinated with 500 μg or 50 μg of the VEEV$_{CO}$ plasmid was $-6.4\%$ and 1.1%, respectively.

The macaques were also monitored for clinical signs of disease after aerosol VEEV challenge. Macaques vaccinated with empty vector DNA displayed mild signs of disease including depression, anorexia, and slightly reduced response to stimuli beginning on day 2 post-challenge, which coordinated with the time of peak serum viremia and the initial peak of fever responses. From post-challenge days 4 to 6, at the time of the secondary peak of fever responses, increased signs of disease including hunched posture with the back turned toward the observer and neurological signs to include loss of coordination and occasional tremors were observed for these macaques. By day 8 post-challenge, and corresponding to a reduction in the severity of the fever responses, only mild signs of disease were evident in these macaques, and on day 9 post-challenge their behavior returned to normal. In contrast, macaques that received either 500 μg or 50 μg of the VEEV$_{CO}$ plasmid displayed limited clinical signs of disease with only slight inactivity observed for some macaques on days 3 and 4 post-challenge.

As provided above, administration of the VEEV$_{CO}$ plasmid provided significantly higher ELISA titers at low doses as compared to the VEEV$_{WT}$ plasmid in mice. Surprisingly, it was found that the VEEV$_{CO}$ plasmid not only elicited higher levels of total IgG, but also elicited greater concentrations of neutralizing antibody titers against VEEV. In addition, as provided above, complete protection from lethal aerosol VEEV challenge of mice vaccinated by i.m. EP with VEEV$_{CO}$ plasmid was observed. Moreover, a balanced IgG1:IgG2a antibody response to VEEV, which is predictive of a balanced Th1:Th2 immune response, is provided by administration of VEEV$_{CO}$ plasmid.

Multivalent EEV DNA Vaccine

Multivalent EEV DNA Vaccine in Mice.

The present invention also provides a single vaccine formulation that can provide simultaneous protection against VEEV, EEEV, and WEEV in subjects, such as humans. Owing to the flexibility of the DNA vaccination platform, multivalent vaccines can be created by combination and co-delivery of multiple different plasmids. Previous studies have demonstrated that multivalent DNA vaccine combinations of plasmids expressing genes from diverse pathogens may provide an effective means of vaccination against multiple pathogens. See Riemenschneider et al. (2003) Vaccine 21:4071-80; and Spik et al. (2006) Vaccine 24:4657-66. However, immune interference has been observed with combinations of plasmids having genes of similar pathogens, e.g. plasmids having genes of substantially similar sequences. See also e.g. McClain et al. (1998) J Infect Dis 177:634-41; and Pittman et al. (2009) Vaccine 27:4879-4882 (examples of known interference with the existing alphavirus IND vaccines).

Figures 10A, 10B:
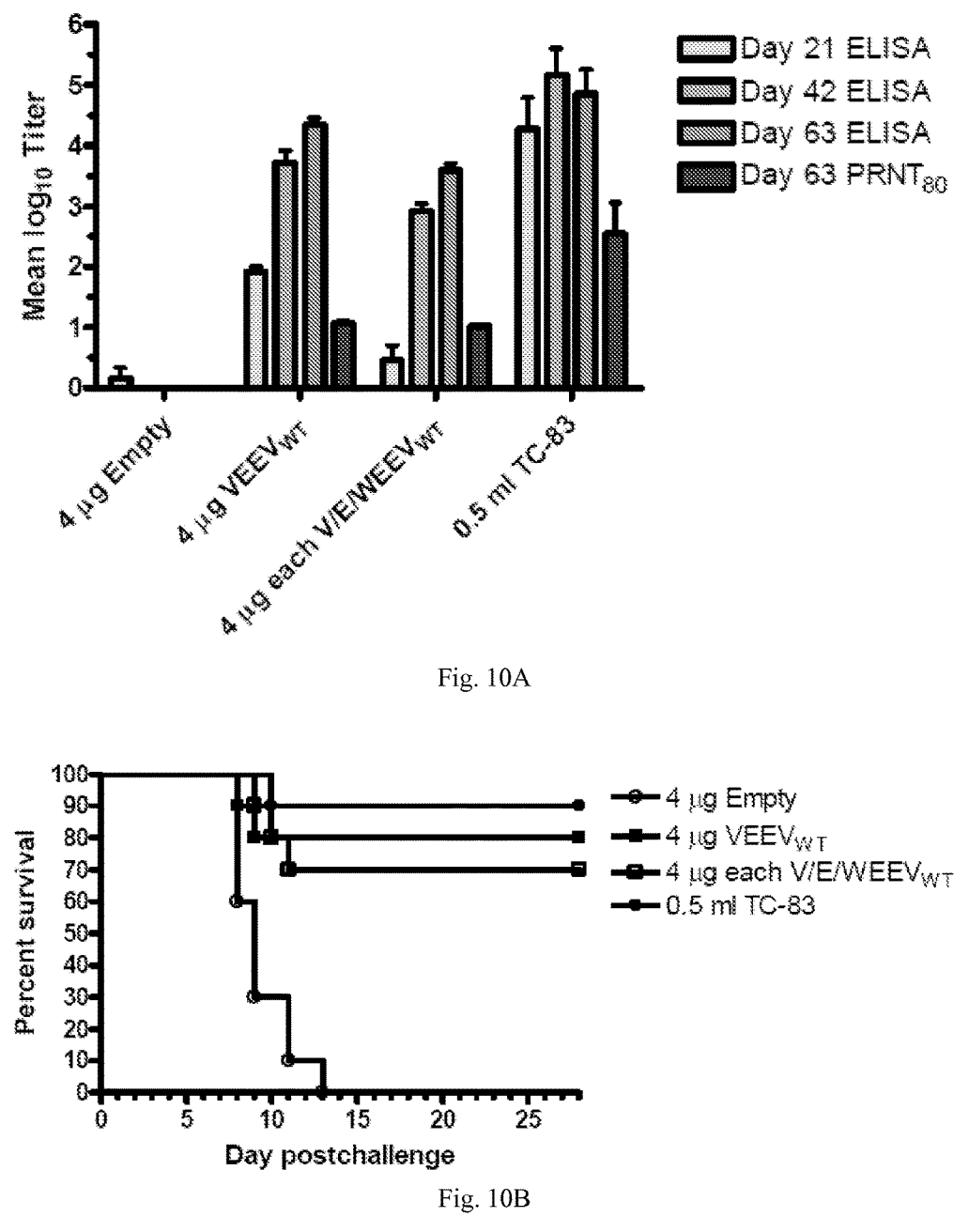

In an initial study to determine whether a multivalent EEV DNA vaccine could be immunogenic and protective, groups of ten female BALB/c mice were vaccinated by PMED three times at 3-week intervals with 4 μg of the VEEV$_{WT}$ plasmid or a WT combination comprising 4 μg each of the VEEV$_{WT}$, EEEV$_{WT}$, and WEEV$_{WT}$ plasmids. A negative control group received the plasmid vector with no insert, and a positive control group received TC-83. Serum samples obtained 3 weeks after each vaccination were assayed for total anti-VEEV IgG antibodies by ELISA. The mean ELISA titers of mice vaccinated with the VEEV$_{WT}$ plasmid alone were higher than those of mice vaccinated with the WT combination after each of the three vaccinations (FIG. 10A). Mice vaccinated with the VEEV$_{WT}$ plasmid alone or with the WT combination displayed similar low PRNT titers. To assess vaccine efficacy, the mice from all groups were challenged four weeks after the final vaccination with about 10$^4$ PFU ($\geq$1,000 LD$_{50}$) of VEEV IAB strain Trinidad donkey administered by the aerosol route. Consistent with results from previous aerosol challenge studies (Dupuy et al. (2009) Vaccine 27:4152-60; and Riemenschneider et al. (2003) Vaccine 21:4071-80), 80% of the mice receiving the VEEV$_{WT}$ plasmid alone survived the challenge (FIG. 10B). Mice receiving the WT combination had a lower survival rate of 70%. The reduced immunogenicity and protective efficacy of the WT combination compared to the VEEV$_{WT}$ plasmid alone was not altogether unexpected, as immune interference has been observed after sequential administration of investigational alphavirus vaccines in humans. See McClain et al. (1998) J Infect Dis 177:634-41; and Pittman et al. (2009) Vaccine 27:4879-4882.

Figures 11A, 11B:
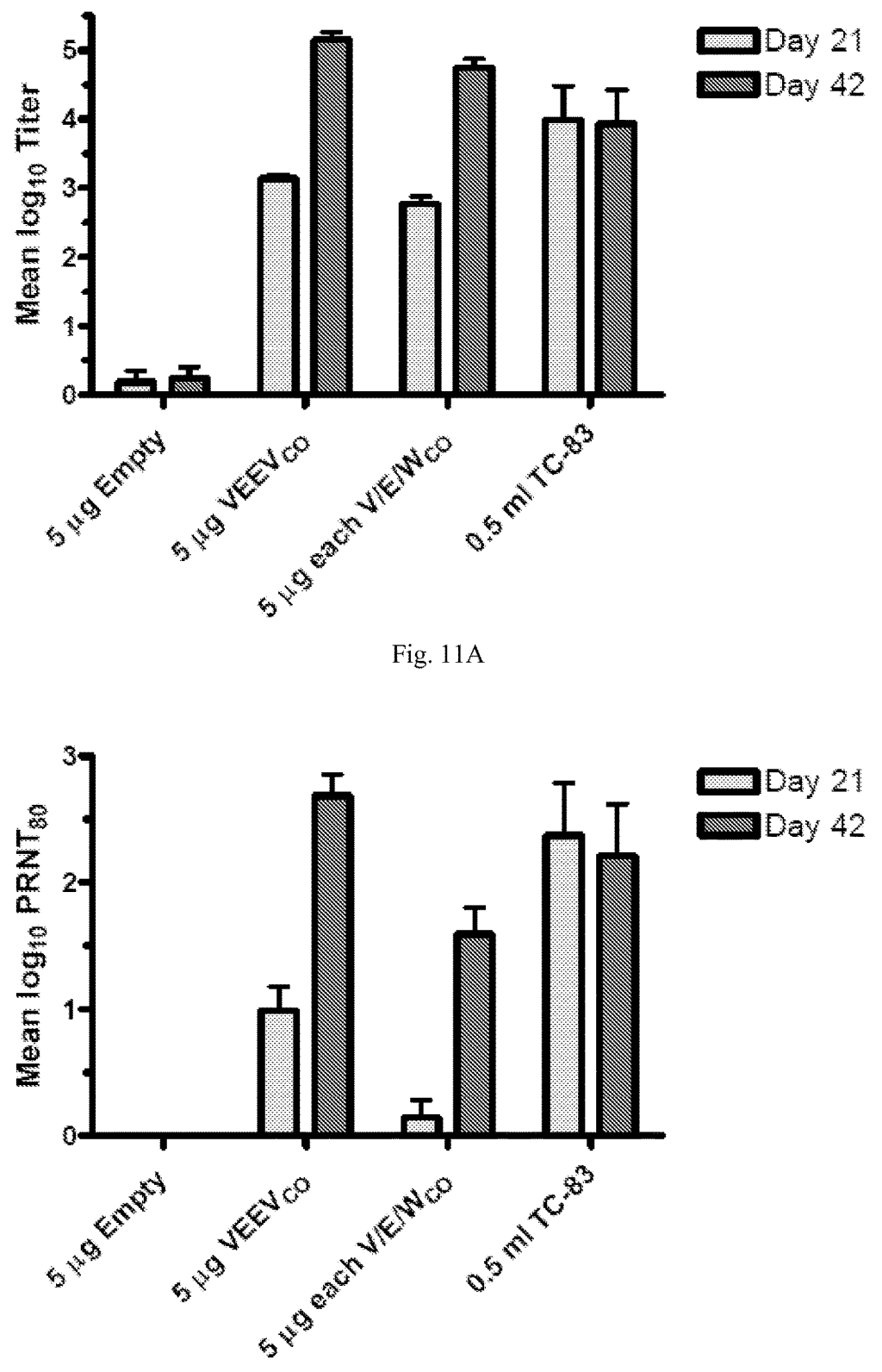
Figures 12, 13, 14:
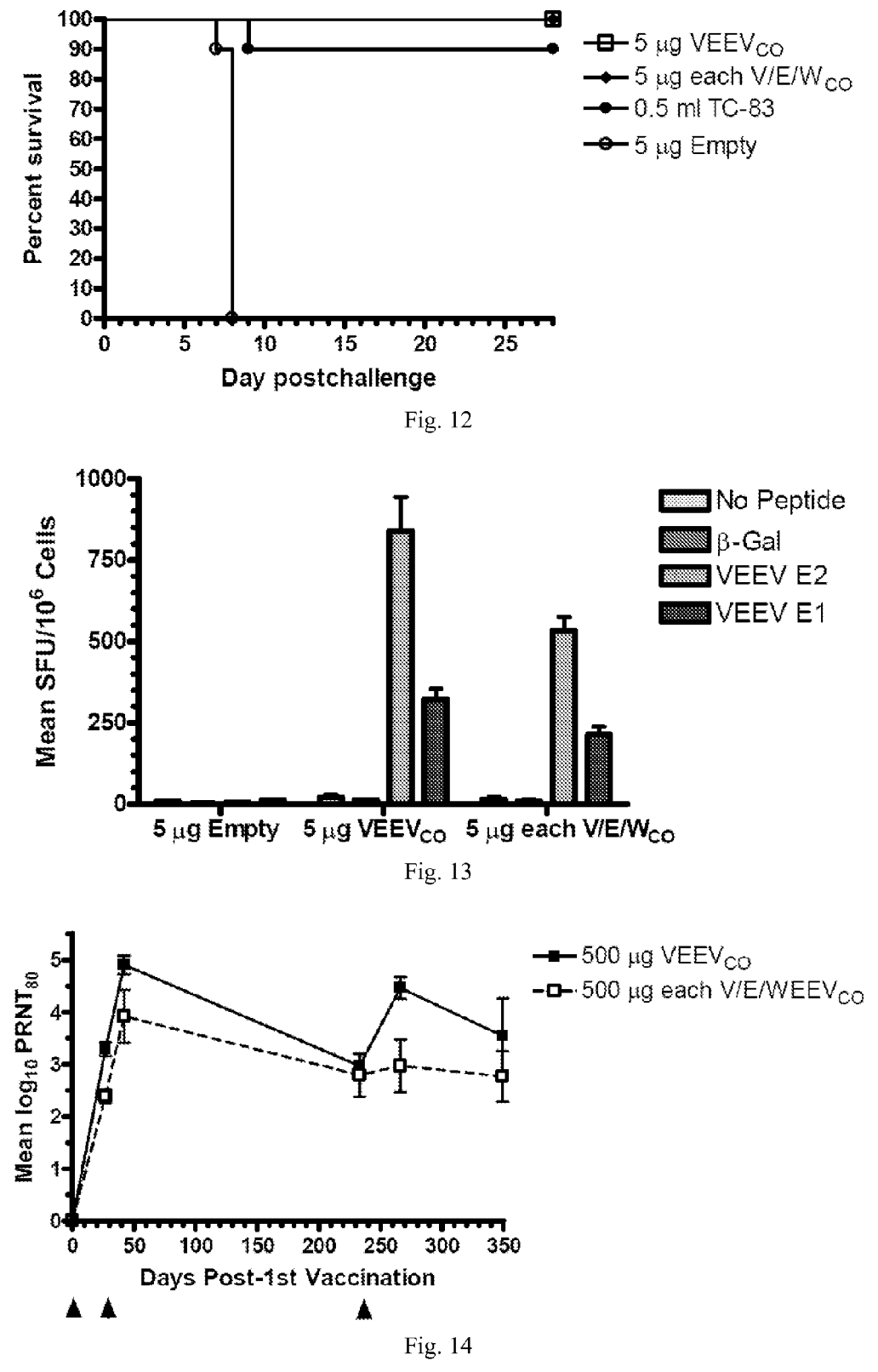

To determine whether the immunogenicity and protective efficacy of a multivalent EEV DNA vaccine could be improved, groups of ten female BALB/c mice were vaccinated by i.m. EP twice at a 3-week interval with 5 μg of the VEEV$_{CO}$ plasmid or a combination composition comprising 5 μg each of the VEEV$_{CO}$, EEEV$_{CO}$, and WEEV$_{CO}$ plasmids. A negative control group received the plasmid vector with no insert, and a positive control group received TC-83. Serum samples obtained 3 weeks after each vaccination were assayed for total anti-VEEV IgG antibodies by ELISA and for VEEV-neutralizing antibodies by PRNT. The mean ELISA titers of mice vaccinated with the VEEV$_{CO}$ plasmid alone were not significantly different from those of mice vaccinated with the combination composition after each of the three vaccinations (FIG. 11A); however, the mean PRNT$_{80}$ titers elicited with the combination composition were lower than those for the VEEV$_{CO}$ plasmid alone after each vaccination (FIG. 11B). To assess vaccine efficacy, the mice from all groups were challenged four weeks after the final vaccination with about $10^4$ PFU ($\geq$1,000 LD$_{50}$) of VEEV IAB strain Trinidad donkey administered by the aerosol route. Surprisingly, unlike the WT combination, mice vaccinated with the individual VEEV$_{CO}$ plasmid and with the CO combination composition were completely protected from challenge (FIG. 12).

To evaluate the cell-mediated immune responses, groups of female BALB/c mice (N=6) were vaccinated twice at a 3-week interval with 5 μg of empty vector or VEEV$_{CO}$ plasmid or a combination composition comprising 5 μg each of the VEEV$_{CO}$, EEEV$_{CO}$, and WEEV$_{CO}$ plasmids delivered by i.m. EP. Two weeks after the second vaccination, splenocytes isolated from the vaccinated mice were restimulated with no peptide, Concanavalin A, a β-galactosidase control peptide, or pools of overlapping peptides spanning the VEEV IAB E2 or E1 envelope glycoproteins and analyzed by IFN-γ ELISPOT. Splenocytes restimulated with Concanavalin A produced a number of spots that were too numerous to count (data not shown). Splenocytes restimulated with no peptide or with the β-galactosidase peptide failed to produce a response in this assay. After restimulation with pooled peptides representing the VEEV E2 or E1 protein, splenocytes obtained from mice vaccinated with the VEEV$_{CO}$ plasmid alone and those vaccinated with the combination composition produced measurable IFN-γ responses (FIG. 13). However, the mean IFN-γ response was lower for the combination composition. Interestingly, the mean IFN-γ response of splenocytes restimulated with the VEEV E2 pooled peptides was significantly higher than that of those restimulated with the VEEV E1 pooled peptides for the VEEV$_{CO}$ plasmid and combination composition groups.

Multivalent EEV DNA Vaccine in Rabbits.

To assess the immunogenicity of the multivalent EEV DNA vaccine in another species, female New Zealand White rabbits (N=5) were vaccinated with 500 μg of the VEEV$_{CO}$ plasmid or a combination composition comprising 500 μg each of the VEEV$_{CO}$, EEEV$_{CO}$, and WEEV$_{CO}$ plasmids delivered by i.m. EP on days 0, 28, and 230, and their antibody responses to VEEV were measured on days 0, 28, 42, 230, 266, and 349 by PRNT. The rabbits of both groups produced high titers of VEEV-neutralizing antibodies after a single vaccination and upon receiving a second vaccination, their mean PRNT$_{80}$ titers were significantly boosted (FIG. 14). The PRNT$_{80}$ titer of rabbits receiving the combination composition was lower than those of rabbits receiving the individual VEEV$_{CO}$ plasmid on all days except day 230, yet they still remained remarkably high. In addition, the mean PRNT$_{80}$ titer of the combination composition was boosted to a lesser degree after an additional DNA vaccination performed on day 230 as compared to the individual VEEV$_{CO}$ plasmid.

B. EEEV

Experiments similar to those conducted for VEEV nucleic acid molecules and VEEV challenges were also conducted for EEEV sequences and challenges in accordance with the sequences and methods described herein.

The sequences of the EEEV nucleic acid molecules are as follows:

EEEV$_{CO}$:

(SEQ ID NO: 3)
ATGAGCCTGGCCACCGTGATGTGCGTGCTGGCCAACATCACCTTCCCTTG

CGACCAGCCCCCTGCATGCCCTGCTGCTACGAGAAGAACCCCCACGAGA

CCCTGACCATGCTGGAACAGAACTACGACAGCCGGGCCTACGACCAGCTG

CTGGACGCCGCCGTGAAGTGCAACGCCAGGCGGACCAGGCGGGACCTGGA

CACCCACTTCACCCAGTACAAGCTGGCCAGGCCCTACATCGCCGACTGCC

CCAACTGCGGCCACAGCAGATGCGACAGCCCCATCGCCATCGAGGAAGTG

AGAGGCGACGCCCATGCTGGAGTCATCCGGATCCAGACCAGCGCCATGTT

CGGCCTGAAAACCGACGGCGTGGACCTGGCCTACATGAGCTTCATGAACG

GCAAGACCCAGAAGAGCATCAAGATCGACAACCTGCACGTGCGGACCTCC

GCCCCCTGCAGCCTGGTGTCCCACCACGGCTACTACATCCTGGCCCAGTG

CCCCCCTGGCGACACCGTGACCGTGGGCTTCCACGACGGCCCCAACCGGC

ACACCTGCACCGTGGCCCACAAGGTGGAGTTCCGGCCCGTGGGCCGGGAG

AAGTACCGGCACCCCCCGAGCACGGCGTGGAGCTGCCCTGCAACCGGTA

CACCCACAAGCGGGCCGACCAGGGCCACTACGTGGAGATGCACCAGCCCG

GCCTGGTGGCCGACCACAGCCTGCTGTCCATCCACAGCGCCAAGGTGAAA

ATCACCGTGCCCAGCGGAGCCCAGGTGAAGTACTACTGCAAGTGCCCCGA

CGTGCGGGAGGGCATCACCAGCAGCGACCACACCACCACCTGTACCGACG

TGAAGCAGTGCAGGGCCTACCTGATCGACAACAAGAAATGGGTGTACAAC

AGCGGCAGGCTGCCCAGAGGCGAGGGCGACACCTTCAAGGGCAAGCTGCA

CGTGCCCTTCGTGCCCGTGAAGGCCAAGTGCATCGCCACCCTGGCCCCCG

AGCCCCTGGTGGAGCACAAGCACCGGACCCTGATCCTGCACCTGCACCCC

GACCACCCCACCCTGCTGACCACCAGAAGCCTGGGCAGCGACGCCAACCC

CACCCGGCAGTGGATCGAGCGGCCCACCACCGTGAACTTTACCGTGACCG

GCGAGGGCCTGGAATACACCTGGGGCAACCACCCCCCCAAGAGAGTGTGG

GCCCAGGAAAGCGGCGAGGGCAACCCTCACGGCTGGCCCCACGAAGTGGT

GGTCTACTACTACAACAGATACCCCCTGACCACCATCATCGGCCTGTGCA

CCTGCGTGGCCATCATCATGGTGTCCTGCGTGACCAGCGTGTGGCTGCTG

TGCCGGACCCGGAACCTGTGCATCACCCCCTATAAGCTGGCCCCCAACGC

CCAGGTGCCCATCCTGCTGGCCCTGCTGTGCTGCATCAAGCCCACCAGGG

CCGACGACACCCTGCAGGTGCTGAACTACCTGTGGAACAACAACCAGAAC

TTCTTCTGGATGCAGACACTGATCCCCCTGGCCGCCCTGATCGTGTGCAT

GCGGATGCTGCGGTGCCTGTTCTGCTGCGGCCCTGCCTTCCTGCTGGTGT

GCGGAGCCCTGGGCGCCGCCGCCTACGAGCACACCGCCGTGATGCCCAAC

-continued

```
AAAGTGGGCATCCCCTACAAGGCCCTGGTGGAAAGGCCCCGGCTACGCCCC
CGTGCACCTGCAGATCCAGCTGGTGAACACCCGGATCATCCCCAGCACCA
ATCTGGAATACATCACCTGCAAGTACAAGACCAAGGTGCCCAGCCCCGTG
GTGAAGTGCTGCGGCGCCACCCAGTGCACCAGCAAGCCCCACCCCGACTA
CCAGTGCCAGGTGTTCACCGGCGTGTACCCCTTCATGTGGGGCGGAGCCT
ACTGCTTCTGCGACACCGAGAACACCCAGATGAGCGAGGCCTACGTGGAG
CGGAGCGAGGAATGCAGCATCGACCACGCCAAGGCCTACAAGGTGCACAC
CGGCACAGTGCAGGCCATGGTGAACATCACCTACGGCAGCGTGAGCTGGC
GGAGCGCCGACGTGTACGTGAATGGCGAGACCCCCGCCAAGATCGGCGAC
GCCAAGCTGATCATCGGCCCCCTGAGCAGCGCCTGGTCCCCCTTCGACAA
CAAAGTGGTGGTGTATGGCCACGAGGTGTACAACTACGACTTCCCCGAGT
ACGGCACCGGCAAGGCCGGCAGCTTCGGCGACCTGCAGAGCCGGACCAGC
ACCAGCAACGACCTGTACGCCAACACCAACCTGAAGCTGCAGCGGCCCCA
GGCCGGCATCGTGCACACCCCTTTCACCCAGGCCCCCAGCGGCTTCGAGC
GGTGGAAGCGGGACAAAGGCGCCCCTCTGAACGACGTGGCCCCCTTCGGC
TGCAGCATCGCCCTGGAACCCCTGCGGGCCGAGAACTGCGCCGTGGGCAG
CATCCCCATCAGCATCGACATCCCCGACGCCGCCTTCACCAGGATCTCCG
AGACCCCCACCGTGAGCGACCTGGAATGCAAGATCACCGAGTGCACCTAC
GCCAGCGACTTCGGCGGCATCGCCACAGTGGCCTACAAGTCCAGCAAGGC
CGGAAACTGCCCCATCCACTCCCCCTCCGGCGTGGCCGTGATCAAAGAAA
ACGACGTGACCCTGGCCGAGAGCGGCAGCTTCACCTTCCACTTCAGCACC
GCCAACATCCACCCCGCCTTCAAGCTGCAGGTGTGCACCAGCGCCGTGAC
CTGCAAGGGCGACTGCAAGCCCCCCAAGGACCACATCGTGGACTACCCCG
CCCAGCACACCGAGAGCTTCACCTCCGCCATCAGCGCCACCGCCTGGTCC
TGGCTGAAGGTGCTGGTCGGCGGCACCTCCGCCTTCATCGTGCTGGGCCT
GATCGCCACAGCCGTGGTGGCCCTGGTGCTGTTCTTCCACCGGCACTGAT
GA.
```

As used herein, a plasmid containing SEQ ID NO: 3 is referred to as "EEEV$_{CO}$ plasmid".

EEEV$_{COCAP}$:

(SEQ ID NO: 4)
```
ATGTTCCCTTACCCCACCCTGAACTACCCCCCCATGGCCCCCATCAACCC
CATGGCCTACCGGGACCCTAACCCTCCCAGACGCCGGTGGCGGCCCTTCA
GACCCCCTCTGGCCGCCCAGATCGAGGACCTGCGGCGGAGCATTGCCAGC
CTGACCCTGAAGCAGAGAGCCCCCAACCCTCCTGCCGGCCCTCCCGCCAA
GCGGAAGAAGCCTGCCCCCAAGCCCAAGCCCGCCCAGGCCAAGAAGAAGA
GGCCCCCTCCCCCTGCCAAGAAGCAGAAGCGGAAGCCTAAGCCCGGCAAG
CGGCAGCGGATGTGCATGAAGCTGGAAAGCGACAAGACCTTCCCCATCAT
GCTGAACGGCCAGGTGAACGGCTACGCCTGCGTGGTGGGGGGCAGAGTGT
TCAAGCCCCTGCACGTGGAGGGCCGGATCGACAACGAGCAGCTGGCCGCC
ATCAAGCTGAAGAAGGCCAGCATCTACGACCTGGAATACGGCGACGTGCC
CCAGTGCATGAAGTCCGACACCCTGCAGTACACCAGCGACAAGCCCCCTG
```

```
GCTTCTACAACTGGCACCACGGGGCCGTGCAGTACGAGAACAACAGATTC
ACCGTGCCCAGAGGCGTGGGCGGCAAGGGCGACAGCGGCAGACCCATCCT
GGACAACAAGGGCCGGGTGGTGGCCATCGTGCTGGGCGGCGTGAACGAGG
GCAGCCGGACCGCCCTGAGCGTGGTGACCTGGAACCAGAAAGGCGTGACC
GTGAAGGACACCCCCGAGGGCAGCGAGCCTTGGAGCCTGGCCACCGTGAT
GTGCGTGCTGGCCAACATCACCTTCCCTTGCGACCAGCCCCCTGCATGC
CCTGCTGCTACGAGAAGAACCCCCACGAGACCCTGACCATGCTGGAACAG
AACTACGACAGCCGGGCCTACGACCAGCTGCTGGACGCCGCCGTGAAGTG
CAACGCCAGGCGGACCAGGCGGGACCTGGACACCCACTTCACCCAGTACA
AGCTGGCCAGGCCCTACATCGCCGACTGCCCCAACTGCGGCCACAGCAGA
TGCGACAGCCCCATCGCCATCGAGGAAGTGAGAGGCGACGCCCATGCTGG
AGTCATCCGGATCCAGACCAGCGCCATGTTCGGCCTGAAAACCGACGGCG
TGGACCTGGCCTACATGAGCTTCATGAACGGCAAGACCCAGAAGAGCATC
AAGATCGACAACCTGCACGTGCGGACCTCCGCCCCCTGCAGCCTGGTGTC
CCACCACGGCTACTACATCCTGGCCCAGTGCCCCCCTGGCGACACCGTGA
CCGTGGGCTTCCACGACGGCCCCAACCGGCACACCTGCACCGTGGCCCAC
AAGGTGGAGTTCCGGCCCGTGGGCCGGGAGAAGTACCGGCACCCCCCCGA
GCACGGCGTGGAGCTGCCCTGCAACCGGTACACCCACAAGCGGGCCGACC
AGGGCCACTACGTGGAGATGCACCAGCCCGGCCTGGTGGCCGACCACAGC
CTGCTGTCCATCCACAGCGCCAAGGTGAAAATCACCGTGCCCAGCGGAGC
CCAGGTGAAGTACTACTGCAAGTGCCCCGACGTGCGGGAGGGCATCACCA
GCAGCGACCACACCACCACCTGTACCGACGTGAAGCAGTGCAGGGCCTAC
CTGATCGACAACAAGAAATGGGTGTACAACAGCGGCAGGCTGCCCAGAGG
CGAGGGCGACACCTTCAAGGGCAAGCTGCACGTGCCCTTCGTGCCCGTGA
AGGCCAAGTGCATCGCCACCCTGGCCCCCGAGCCCCTGGTGGAGCACAAG
CACCGGACCCTGATCCTGCACCTGCACCCCGACCACCCCACCCTGCTGAC
CACCAGAAGCCTGGGCAGCGACGCCAACCCCACCCGGCAGTGGATCGAGC
GGCCCACCACCGTGAACTTTACCGTGACCGGCGAGGGCCTGGAATACACC
TGGGGCAACCACCCCCCAAGAGAGTGTGGGCCCAGGAAAGCGGCGAGGG
CAACCCTCACGGCTGGCCCCACGAAGTGGTGGTCTACTACTACAACAGAT
ACCCCCTGACCACCATCATCGGCCTGTGCACCTGCGTGGCCATCATCATG
GTGTCCTGCGTGACCAGCGTGTGGCTGCTGTGCCGGACCCGGAACCTGTG
CATCACCCCTATAAGCTGGCCCCCAACGCCCAGGTGCCCATCCTGCTGG
CCCTGCTGTGCTGCATCAAGCCCACCAGGGCCGACGACACCCTGCAGGTG
CTGAACTACCTGTGGAACAACAACCAGAACTTCTTCTGGATGCAGACACT
GATCCCCCTGGCCGCCCTGATCGTGTGCATGCGGATGCTGCGGTGCCTGT
TCTGCTGCGGCCCTGCCTTCCTGCTGGTGTGCGGAGCCCTGGGCGCCGCC
GCCTACGAGCACGCCGCCGTGATGCCCAACAAAGTGGGCATCCCCTACAA
GGCCCTGGTGGAAAGGCCCGGCTACGCCCCCGTGCACCTGCAGATCCAGC
TGGTGAACACCCGGATCATCCCCAGCACCAATCTGGAATACATCACCTGC
```

```
-continued
AAGTACAAGACCAAGGTGCCCAGCCCCGTGGTGAAGTGCTGCGGCGCCAC

CCAGTGCACCAGCAAGCCCCACCCCGACTACCAGTGCCAGGTGTTCACCG

GCGTGTACCCCTTCATGTGGGCGGAGCCTACTGCTTCTGCGACACCGAG

AACACCCAGATGAGCGAGGCCTACGTGGAGCGGAGCGAGGAATGCAGCAT

CGACCACGCCAAGGCCTACAAGGTGCACACCGGCACAGTGCAGGCCATGG

TGAACATCACCTACGGCAGCGTGAGCTGGCGGAGCGCCGACGTGTACGTG

AATGGCGAGACCCCCGCCAAGATCGGCGACGCCAAGCTGATCATCGGCCC

CCTGAGCAGCGCCTGGTCCCCCTTCGACAACAAAGTGGTGGTGTATGGCC

ACGAGGTGTACAACTACGACTTCCCCGAGTACGGCACCGGCAAGGCCGGC

AGCTTCGGCGACCTGCAGAGCCGGACCAGCACCAGCAACGACCTGTACGC

CAACACCAACCTGAAGCTGCAGCGGCCCCAGGCCGGCATCGTGCACACCC

CTTTCACCCAGGCCCCCAGCGGCTTCGAGCGGTGGAAGCGGGACAAAGGC

GCCCCTCTGAACGACGTGGCCCCCTTCGGCTGCAGCATCGCCCTGGAACC

CCTGCGGGCCGAGAACTGCGCCGTGGGCAGCATCCCCATCAGCATCGACA

TCCCCGACGCCGCCTTCACCAGGATCTCCGAGACCCCCACCGTGAGCGAC

CTGGAATGCAAGATCACCGAGTGCACCTACGCCAGCGACTTCGGCGGCAT

CGCCACAGTGGCCTACAAGTCCAGCAAGGCCGGAAACTGCCCCATCCACT

CCCCCTCCGGCGTGGCCGTGATCAAAGAAAACGACGTGACCCTGGCCGAG

AGCGGCAGCTTCACCTTCCACTTCAGCACCGCCAACATCCACCCCGCCTT

CAAGCTGCAGGTGTGCACCAGCGCCGTGACCTGCAAGGGCGACTGCAAGC

CCCCCAAGGACCACATCGTGGACTACCCCGCCCAGCACACCGAGAGCTTC

ACCTCCGCCATCAGCGCCACCGCCTGGTCCTGGCTGAAGGTGCTGGTCGG

CGGCACCTCCGCCTTCATCGTGCTGGGCCTGATCGCCACAGCCGTGGTGG

CCCTGGTGCTGTTCTTCCACCGGCACTGATGA.
As used herein, a plasmid containing
SEQ ID NO: 4 is referred to as
"EEEV$_{COCAP}$ plasmid".
```

EEEV DNA Vaccine in Mice.

Figures 15A, 15B:
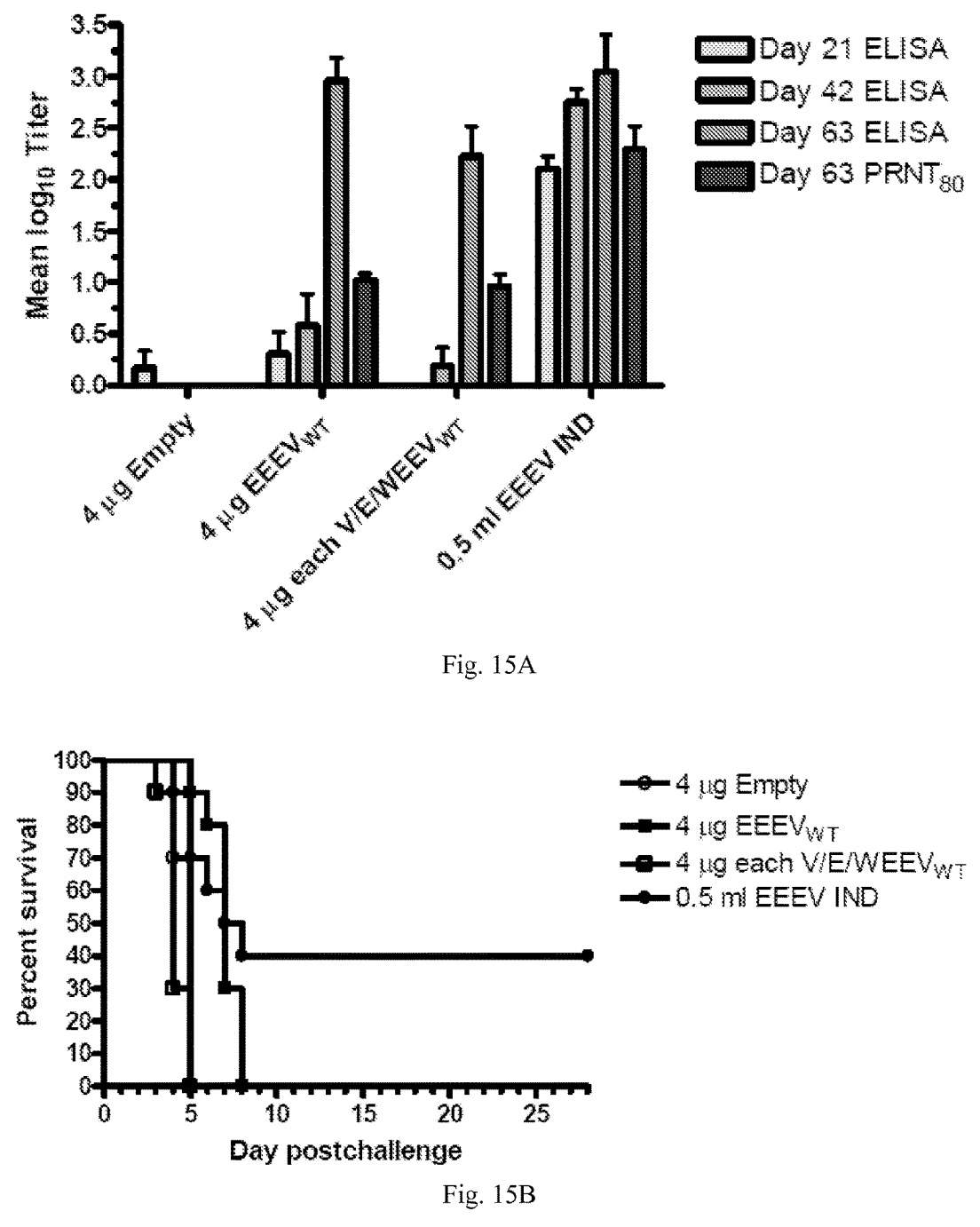

An initial study was performed to assess the immunogenicity and protective efficacy of EEEV$_{WT}$, a DNA plasmid expressing the wild-type structural proteins (C-E3-E2-6K-E1) of EEEV (strain PE6), both alone and in combination with the VEEV$_{WT}$ and WEEV$_{WT}$ plasmids (WT combination). For this, groups of ten female BALB/c mice were vaccinated by PMED three times at 3-week intervals with 4 µg of the EEEV$_{WT}$ plasmid or the WT combination comprising 4 µg each of the EEEV$_{WT}$, VEEV$_{WT}$, and WEEV$_{WT}$ plasmids. A negative control group received 4 µg of the plasmid vector with no insert three times at 3-week intervals by PMED. A positive control group was vaccinated three times at 3-week intervals with 0.5 ml of the formalin-inactivated EEEV IND vaccine delivered by subcutaneous injection. Serum samples obtained 3 weeks after each vaccination were assayed for total anti-EEEV IgG antibodies by ELISA, and serum samples obtained three weeks after the third and final vaccination were also assayed for EEEV-neutralizing antibodies by PRNT. The mean ELISA titers of mice vaccinated with the EEEV$_{WT}$ plasmid alone were higher than those of mice vaccinated with the WT combination after each of the three vaccinations (FIG. 15A). Mice vaccinated with the EEEV$_{WT}$ plasmid alone or in the WT combination displayed similar low PRNT titers. To assess vaccine efficacy, the mice from all groups were challenged four weeks after the final vaccination with about $10^4$ PFU (~300 LD$_{50}$) of EEEV strain PE6 administered by the aerosol route. None of the mice vaccinated with EEEV$_{WT}$ survived the challenge; however, there was a significant delay in the day to death as compared to the negative control mice. Although there was also a complete lack of survival of mice vaccinated with the WT combination, these mice died with similar kinetics as the negative controls. Mice vaccinated with the EEEV IND were protected at a level of 40% (FIG. 15B).

To determine whether the EEEV DNA vaccine could be improved by employing the same strategy that proved successful for the VEEV DNA vaccine, the wild type 26S structural genes minus the capsid sequence (E3-E2-6K-E1) of EEEV strain FL91-4679 (Genbank accession number AY705241) were codon optimized by subjecting these genes to a GeneOptimizer™ bioinformatic algorithm (Geneart, Regensburg, Germany) for mammalian expression, and the codon optimized genes were synthesized using methods known in the art. The EEEV$_{CO}$ plasmid was constructed by cloning these synthesized codon optimized genes into the NotI and BglII restriction sites of pWRG7077 using methods known in the art. EEEV strain FL91-4679 was chosen because it was unexpectedly found to represent a consensus sequence after performing an alignment of the structural gene sequences of many EEEV strains.

Figures 16A, 16B:
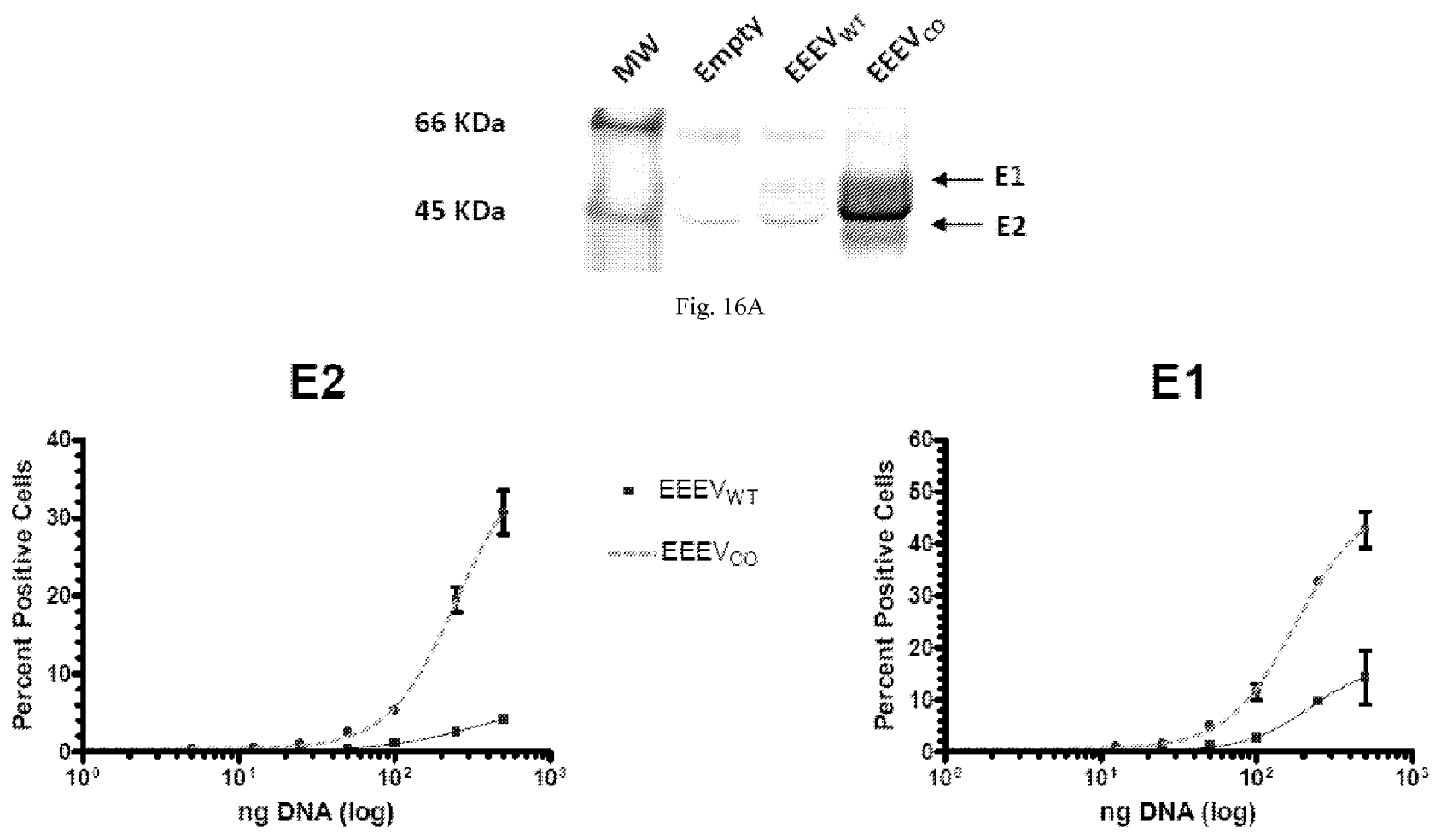

To determine if the EEEV$_{CO}$ construct showed improved expression of the envelope glycoproteins as compared to the previous EEEV$_{WT}$ construct, the proteins expressed in transiently transfected mammalian cells were detected by immune precipitation assay. The expression of the E2 and E1 envelope glycoproteins from the EEEV$_{CO}$ construct was increased approximately tenfold relative to that of the EEEV$_{WT}$ construct in this assay (FIG. 16A). To further quantify the relative in vitro expression levels of these constructs, the percent of cells positive for E2 and E1 expression after transient transfection of 5-500 ng of each DNA vaccine plasmid was determined by flow cytometry. A significant increase in the mean percent of cells positive for E2 and E1 expression was observed for the EEEV$_{CO}$ DNA plasmid at the 50-500 ng sample concentrations (FIG. 16B).

Figures 17A, 17B:
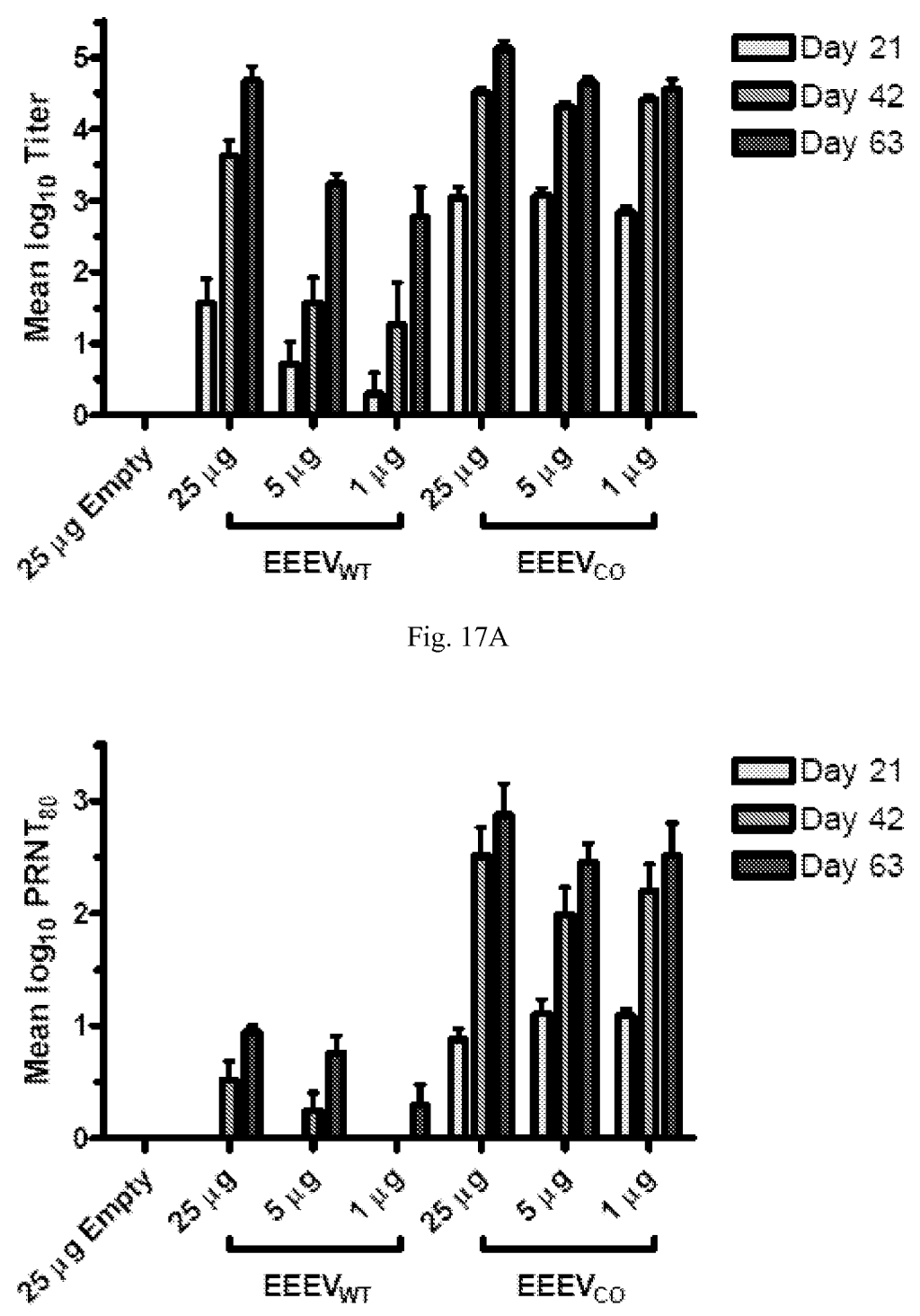

In an initial study to determine whether the immunogenicity of the EEEV$_{CO}$ plasmid was improved relative to the EEEV$_{WT}$ plasmid, groups of six female BALB/c mice were vaccinated by i.m. EP three times at 3-week intervals with 25 µg, 5 µg, or 1 µg of DNA. A negative control group received 25 µg of the plasmid vector with no insert. Serum samples obtained 3 weeks after each vaccination were assayed for total anti-EEEV IgG antibodies by ELISA and for EEEV-neutralizing antibodies by PRNT. The mean ELISA titers of mice vaccinated with the EEEV$_{CO}$ plasmid were significantly higher than those of mice vaccinated with the EEEV$_{WT}$ construct for the 5 µg and 1 µg dose groups after each of the three vaccinations (FIG. 17A). The mean PRNT$_{80}$ titer elicited by mice vaccinated with the EEEV$_{CO}$ plasmid was significantly higher than that observed for mice vaccinated with the EEEV$_{WT}$ construct for all dose groups at all days (FIG. 17B).

Figure 18A:
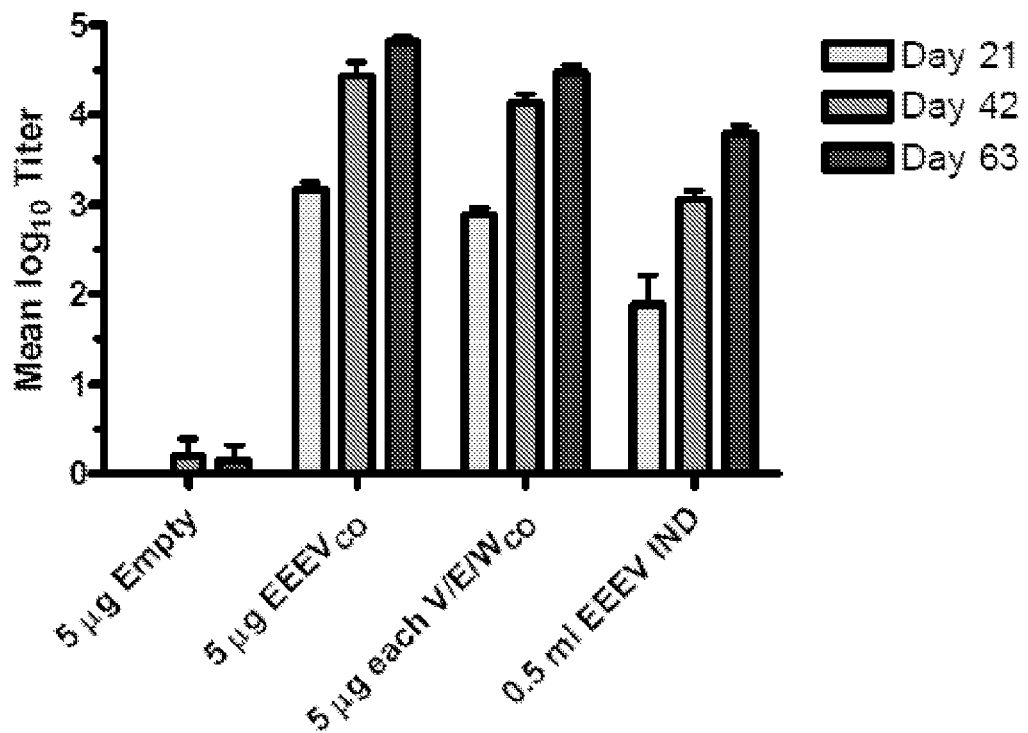
FIGS. 18A and 18B are graphs summarizing the antibody responses of vaccinated mice. Female BALB/c mice (N=10 per group) were vaccinated twice at a 3-week interval with 5 μg of empty vector DNA or EEEV$_{CO}$ or 5 μg each of the EEEV$_{CO}$, VEEV$_{CO}$, and WEEV$_{CO}$ plasmids delivered by i.m. EP. Positive control mice (N=10) each received a single vaccination with 0.5 ml of the formalin-inactivated EEEV IND vaccine delivered by subcutaneous injection. Serum samples obtained 3 weeks after each vaccination were assayed for total IgG anti-EEEV antibodies by ELISA and for EEEV-neutralizing antibodies by PRNT. The mean log$_{10}$ ELISA (FIG. 18A) and PRNT$_{80}$ (FIG. 18B) titers along with the SEM for each group are shown.
Figure 18B:
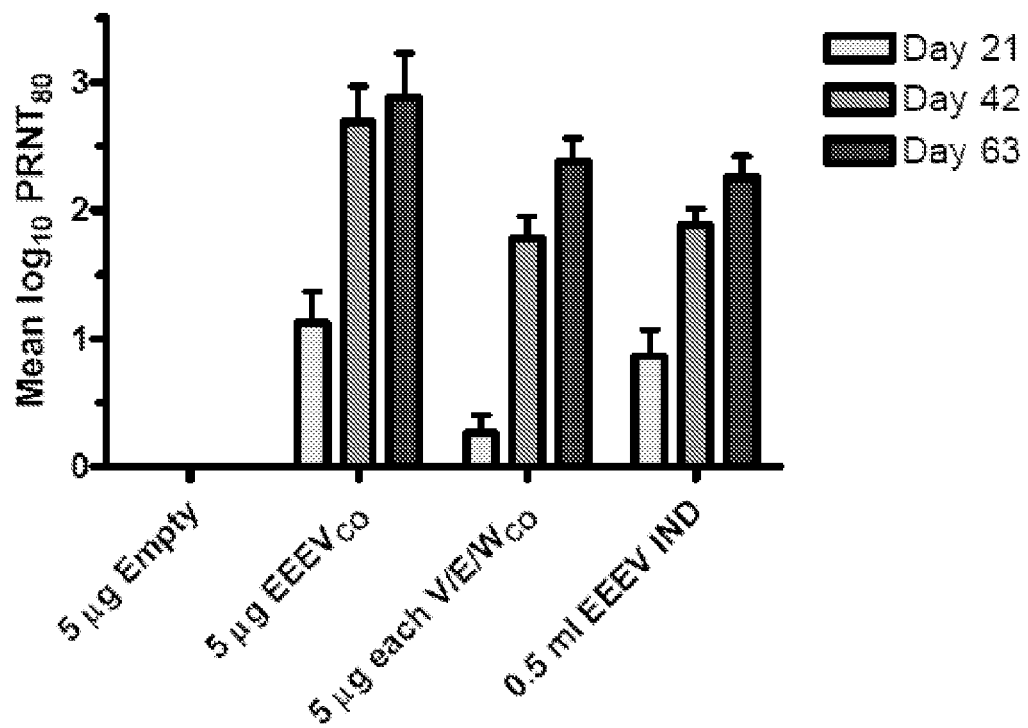

To determine the protective efficacy of the EEEV$_{CO}$ DNA vaccine both alone and in the multivalent EEV combination (combination composition), groups of ten female BALB/c mice were vaccinated by i.m. EP three times at 3-week intervals with 5 µg of the EEEV$_{CO}$ plasmid or a combination composition comprising 5 µg each of the EEEV$_{CO}$, VEEV$_{CO}$, and WEEV$_{CO}$ plasmids. A negative control group received the plasmid vector with no insert, and a positive control group received the formalin-inactivated EEEV IND vaccine. Serum samples obtained 3 weeks after each vaccination were assayed for total anti-EEEV IgG antibodies by ELISA and for EEEV-neutralizing antibodies by PRNT. The mean ELISA titers of mice vaccinated with the $EEEV_{CO}$ plasmid alone were not significantly different from those of mice vaccinated with the combination composition after each of the three vaccinations (FIG. 18A). In addition, the mean ELISA titers of mice receiving the individual $EEEV_{CO}$ plasmid or the combination composition were higher than that of the EEEV IND after each of the three vaccinations. The mean $PRNT_{80}$ titers elicited with the $EEEV_{CO}$ plasmid alone were higher than those for the combination composition or the EEEV IND vaccine after each vaccination, while those of the combination composition were similar to those of the EEEV IND after each of the three vaccinations (FIG. 18B). To assess vaccine efficacy, the mice from all groups were challenged four weeks after the final vaccination with about $10^4$ PFU (~300 $LD_{50}$) of EEEV strain FL91-4679 administered by the aerosol route. Surprisingly, mice vaccinated with the individual $EEEV_{CO}$ plasmid and with the combination composition were completely protected from challenge (FIG. 18). Similar to the results from our previous $EEEV_{WT}$ mouse challenge study, 40% of mice receiving the EEEV IND vaccine survived.

EEEV DNA Vaccine in Rabbits.

Figures 19, 20, 21:
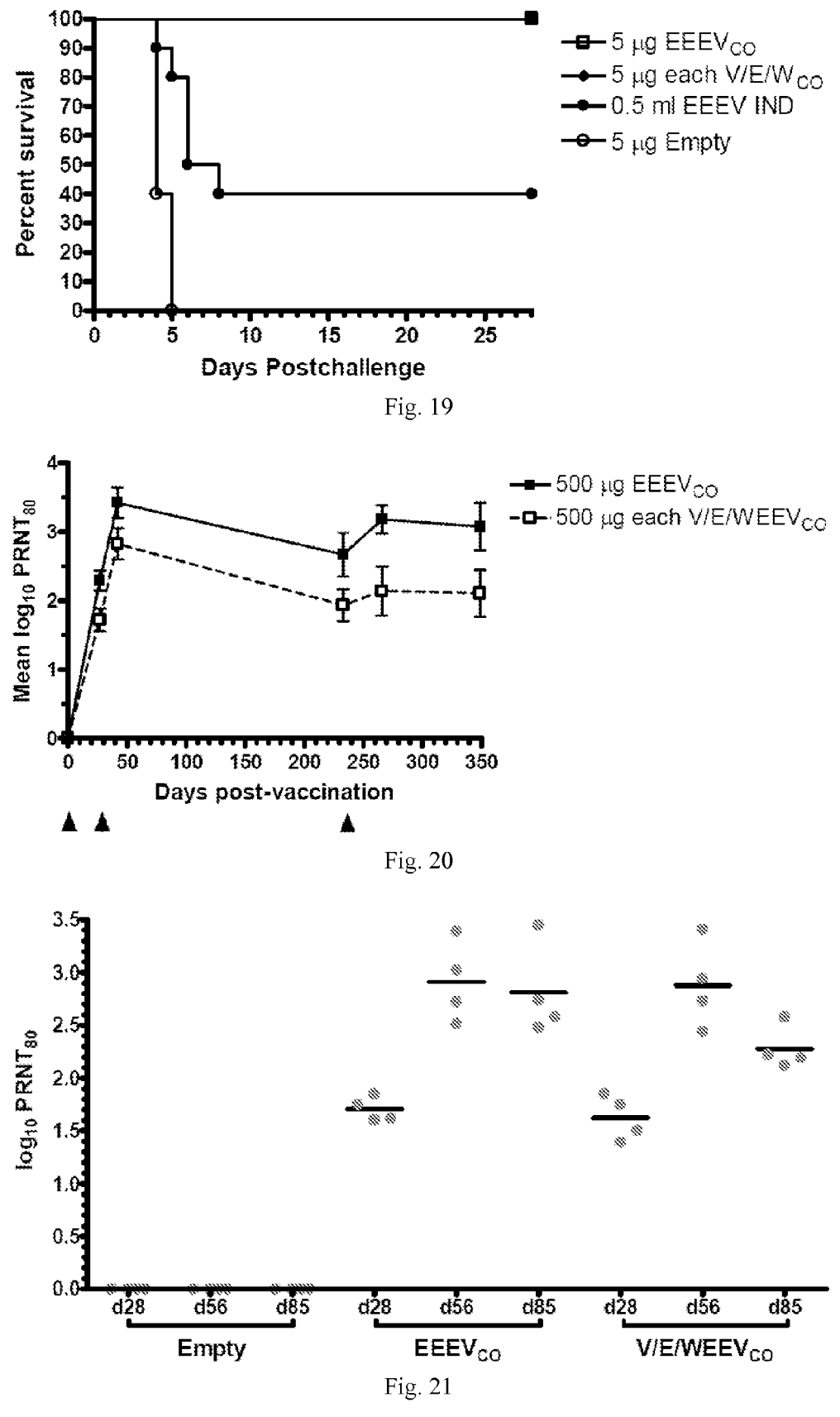

To assess the immunogenicity of the $EEEV_{CO}$ DNA vaccine alone and in the multivalent EEV combination in another species, female New Zealand White rabbits (N=5) were vaccinated with 500 µg of the $EEEV_{CO}$ plasmid or a combination composition comprising 500 µg each of the $EEEV_{CO}$, $VEEV_{CO}$, and $WEEV_{CO}$ plasmids delivered by i.m. EP on days 0, 28, and 230, and their antibody responses to EEEV were measured on days 0, 28, 42, 230, 266, and 349 by PRNT. The rabbits of both groups produced high titers of EEEV-neutralizing antibodies after a single vaccination and upon receiving a second vaccination, their mean $PRNT_{80}$ titers were significantly boosted (FIG. 20). The $PRNT_{80}$ titer of rabbits receiving the combination composition was lower than those of rabbits receiving the individual $VEEV_{CO}$ plasmid on all days, yet they still remained remarkably high. In addition, the mean $PRNT_{80}$ titers of both groups were boosted after an additional DNA vaccination performed on day 230.

EEEV DNA Vaccine in Cynomolgus Macaques.

The immunogenicity and protective efficacy of the $EEEV_{CO}$ plasmid, both alone and in the multivalent EEV combination (combination composition), was assessed using an established model of EEEV infection of nonhuman primates. See Reed et al. (2007) J Infect Dis 196:441-50. Groups of four adult male cynomolgus macaques were vaccinated three times at 4-week intervals with each animal receiving 500 µg of the empty vector DNA plasmid, 500 µg of the $EEEV_{CO}$ plasmid, or a combination composition comprising 500 µg each of the $EEEV_{CO}$, $VEEV_{CO}$, and $WEEV_{CO}$ plasmid delivered by i.m. EP. Serum samples collected 4 weeks after each vaccination were analyzed for EEEV-neutralizing antibodies by PRNT. Similar mean neutralizing antibody titers were elicited in macaques after a single vaccination with the individual $EEEV_{CO}$ plasmid and the combination composition, and the titers of both groups were significantly and similarly boosted after the second vaccination (FIG. 21). The mean titer of neither group was boosted with a third vaccination, and the titers of macaques receiving the $EEEV_{CO}$ plasmid alone were significantly higher than those receiving the combination composition at day 85.

Figure 22A:
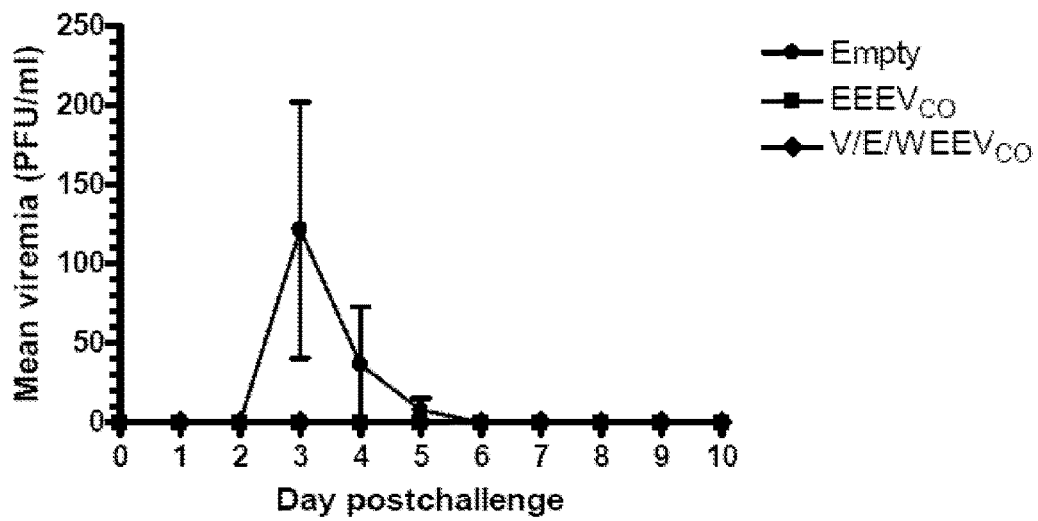
FIGS. 22A and 22B are graphs showing the data for the aerosol challenge of vaccinated macaques. Adult cynomolgus macaques of both sexes (N=4 per group) vaccinated with 500 μg of the empty vector DNA plasmid, 500 μg of the EEEV$_{CO}$ plasmid, or 500 μg each of the EEEV$_{CO}$, VEEV$_{CO}$, and WEEV$_{CO}$ plasmids delivered by i.m. EP on days 0, 28, and 56 were challenged with a calculated dose of $1.6 \times 10^8$ PFU of EEEV FL91-4679 by the aerosol route. After challenge, the macaques were monitored for serum viremia by plaque assay (FIG. 22A) and for clinical signs of disease by blinded observers using established criteria (FIG. 22B). The mean viremias and clinical scores along with the SEM are shown for each group.
Figure 22B:
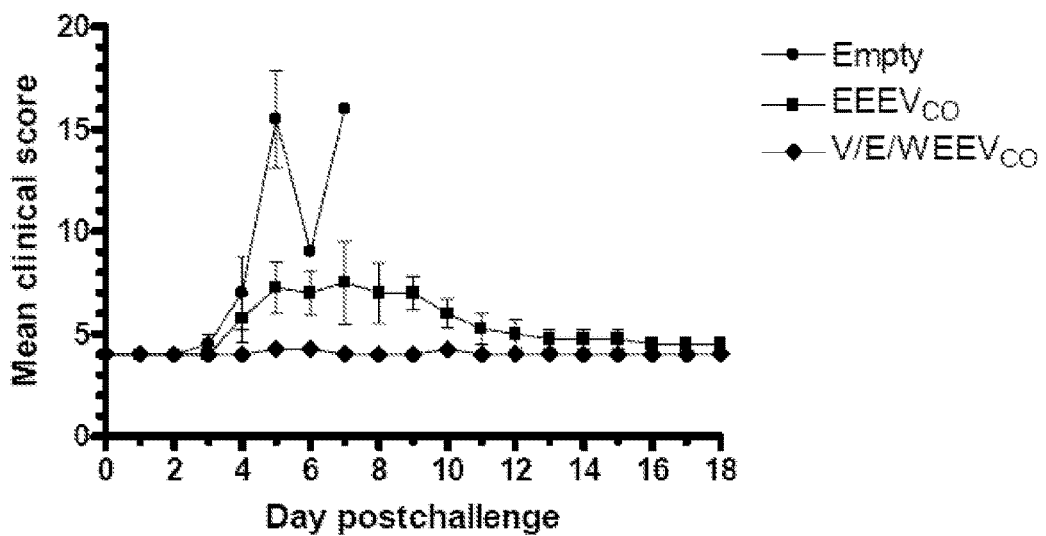

Eight weeks after the third and final vaccination, the macaques were challenged with EEEV strain FL91-4679 administered by the aerosol route, and the average inhaled dose was calculated to be $1.6 \times 10^8$ PFU. While serum viremia was detected in postchallenge samples from 3 of 4 control macaques vaccinated with empty vector plasmid, no serum viremia was detected in any of the postchallenge samples from macaques receiving either the individual $EEEV_{CO}$ plasmid or the combination composition (FIG. 22A). After aerosol EEEV challenge, blinded observations to monitor the macaques for clinical signs of disease, including neurological signs and changes in activity, behavior, and response to stimuli, were performed using established criteria. Macaques vaccinated with empty vector DNA displayed signs of disease beginning on day 2 postchallenge. On day 5 postchallenge, 3 of 4 of these control macaques displayed signs of severe encephalitis and complete inactivity and, having met the established clinical score for a humane endpoint, were euthanized. On day 7 postchallenge, the remaining control macaque also succumbed to disease, met the established clinical score for a humane endpoint, and was euthanized. All of the macaques vaccinated with the individual $EEEV_{CO}$ plasmid or with the combination composition survived the challenge and never met the established clinical score for a humane endpoint. However, 2 of 4 of those receiving the individual $EEEV_{CO}$ plasmid did display signs of illness and had increased clinical scores after challenge resulting in increased mean clinical scores for this group (FIG. 22B). Surprisingly, those macaques vaccinated with the combination composition did not display signs of illness after challenge. This provides the first indication that a multivalent DNA vaccine comprising $VEEV_{CO}$, $EEEV_{CO}$, and $WEEV_{CO}$ plasmids can act synergistically to improve protection from encephalitic alphavirus challenge as compared to the individual DNA vaccines.

C. WEEV

Experiments similar to those conducted for VEEV nucleic acid molecules and VEEV challenges were also conducted for WEEV sequences and challenges in accordance with the sequence and methods described herein.

The sequences of the WEEV nucleic acid molecules are as follows:

$WEEV_{CO}$:

(SEQ ID NO: 5)
ATGAGCCTGGTGACCGCCCTGTGCGTGCTGTCCAACGTGACCTTCCCCTG

CGACAAGCCCCCCGTGTGCTACAGCCTGGCCCCCGAGCGGACCCTGGACG

TGCTGGAAGAGAACGTGGACAACCCCAACTACGACACCCTGCTGGAAAAC

GTGCTGAAGTGCCCCAGCAGGCGGCCCAAGCGGAGCATCACCGACGACTT

CACCCTGACCAGCCCCTACCTGGGCTTCTGCCCCTACTGCCGGCACAGCG

CCCCCTGCTTCAGCCCCATCAAGATCGAGAACGTGTGGGACGAGAGCGAC

GACGGCAGCATCCGGATCCAGGTGTCCGCCCAGTTCGGCTACAACCAGGC

CGGCACCGCCGACGTGACCAAGTTCCGGTACATGAGCTACGACCACGACC

ACGATATCAAGGAAGATAGCATGGAAAAGCTGGCCATCAGCACCAGCGGC

CCCTGCAGACGGCTGGGCCACAAGGGCTACTTTCTGCTGGCCCAGTGCCC

CCCTGGCGACAGCGTGACCGTGAGCATCACCAGCGGCGCCAGCGAGAACA

GCTGCACCGTGGAGAAGAAGATCCGGCGGAAGTTCGTGGGCCGGGAGGAA

TACCTGTTCCCCCCCGTGCACGGCAAGCTGGTGAAGTGCCACGTGTACGA

-continued

CCACCTGAAAGAGACCAGCGCCGGCTACATCACCATGCACCGGCCAGGCC

CCCACGCCTACAAGAGCTACCTGGAAGAGGCCAGCGGCGAGGTGTACATC

AAGCCCCCAGCGGCAAGAACGTGACCTACGAGTGCAAGTGCGGCGACTA

CAGCACCGGCATCGTGAGCACCCGGACCAAGATGAACGGCTGCACCAAGG

CCAAGCAGTGCATCGCCTACAAGGGGACCAGACCAAGTGGGTGTTCAAC

AGCCCCGACCTGATCCGGCACACCGACCACAGCGTGCAGGGCAAACTGCA

CATCCCCTTCCGGCTGACCCCCACCGTGTGCCCCGTGCCCCTGGCCCACA

CCCCTACCGTGACAAAGTGGTTCAAGGGCATCACACTGCACCTGACCGCC

ACCCGGCCCACCCTGCTGACCACCCGGAAGCTGGGCCTGAGGGCCGATGC

CACCGCCGAGTGGATCACCGGCACCACCTCCCGGAACTTCAGCGTGGGCA

GAGAGGGCCTGGAATACGTCTGGGGCAACCACGAGCCCGTGAGAGTGTGG

GCCCAGGAAAGCGCCCCAGGCGACCCCACGGCTGGCCCCACGAGATCAT

CATCCACTACTACCACCGGCACCCCGTGTACACCGTGATCGTGCTGTGCG

GCGTGGCCCTGGCCATCCTGGTGGGCACCGCCAGCAGCGCCGCCTGCATC

GCCAAGGCCAGGCGGGACTGCCTGACCCCCTACGCCCTGGCCCCCAACGC

CACCGTGCCAACCGCCCTGGCCGTGCTGTGCTGCATCCGGCCCACCAACG

CCGAGACCTTCGGCGAGACCCTGAACCACCTGTGGTTCAACAACCAGCCC

TTCCTGTGGGCCCAGCTGTGCATCCCCCTGGCCGCCCTGATCATCCTGTT

CCGGTGCTTCAGCTGCTGCATGCCTTTTCTGCTGGTCGCCGGCGTGTGCC

TGGGCAAGGTGGACGCCTTCGAGCACGCCACCACCGTGCCCAACGTGCCC

GGCATCCCCTACAAGGCCCTGGTGGAGAGGGCCGGCTACGCCCCCCTGAA

CCTGGAAATCACCGTGGTGTCCAGCGAGCTGACCCCCTCCACCAACAAAG

AATACGTGACCTGCAAGTTCCACACCGTGGTGCCCTCCCCCCAGGTGAAG

TGCTGCGGCAGCCTGGAATGCAAGGCCAGCAGCAAGGCCGACTACACCTG

CCGGGTGTTCGGCGGCGTGTACCCCTTCATGTGGGGCGGAGCACAGTGCT

TCTGCGACTCCGAGAACACCCAGCTGTCCGAGGCCTACGTGGAGTTCGCC

CCCGACTGCACCATCGACCACGCCGTGGCCCTGAAGGTGCACACAGCCGC

CCTGAAAGTGGGCCTGCGGATCGTGTACGGCAACACCACCGCCAGGCTGG

ACACCTTCGTGAACGGCGTGACCCCCGGCAGCAGCCGGGACCTGAAGGTG

ATCGCCGGACCCATCTCCGCCGCCTTCAGCCCCTTCGACCACAAGGTGGT

GATCCGGAAGGGCCTGGTGTACAACTACGACTTCCCCGAGTACGGCGCCA

TGAACCCTGGCGCCTTCGGCGACATCCAGGCCAGCTCCCTGGACGCCACC

GACATCGTGGCCCGGACCGACATCCGGCTGCTGAAGCCCAGCGTGAAGAA

CATCCACGTGCCCTACACCCAGGCCGTGAGCGGCTACGAGATGTGGAAGA

ACAACAGCGGCAGACCCCTGCAGGAAACCGCCCCCTTCGGCTGCAAGATC

GAGGTGGAGCCCCTGCGGGCCACCAACTGCGCCTACGGCCACATCCCCAT

CAGCATCGACATCCCCGACGCCGCCTTCGTGCGGAGCAGCGAGAGCCCA

CCATCCTGGAAGTGAGCTGTACCGTGGCCGACTGCATCTACAGCGCCGAC

TTCGGCGGCTCCCTGACCCTGCAGTACAAGGCCAACCGGGAGGGCCACTG

CCCCGTGCACAGCCACAGCACCACCGCCGTGCTGAAAGAGGCCACCACCC

ACGTCACCGCCACAGGCAGCATCACCCTGCACTTCAGCACCAGCTCCCCC

CAGGCCAACTTCATCGTGAGCCTGTGCGGCAAGAAAACCACCTGCAACGC

CGAGTGCAAGCCCCCTGCCGACCACATCATCGGCGAGCCTCACAAGGTGG

ACCAGGAATTCCAGGCCGCCGTCAGCAAGACCAGCTGGAACTGGCTGCTG

GCCCTGTTCGGCGGAGCCAGCAGCCTGATCGTGGTGGGCCTGATTGTGCT

GGTGTGCAGCAGCATGCTGATCAACACCCGGCGGTGATGA.
As used herein, a plasmid containing

-continued

```
CCAAGATGAACGGCTGCACCAAGGCCAAGCAGTGCATCGCCTACAAGCGG

GACCAGACCAAGTGGGTGTTCAACAGCCCCGACCTGATCCGGCACACCGA

CCACAGCGTGCAGGGCAAACTGCACATCCCCTTCCGGCTGACCCCCACCG

TGTGCCCCGTGCCCCTGGCCCACACCCCTACCGTGACAAAGTGGTTCAAG

GGCATCACACTGCACCTGACCGCCACCCGGCCCACCCTGCTGACCACCCG

GAAGCTGGGCCTGAGGGCCGATGCCACCGCCGAGTGGATCACCGGCACCA

CCTCCCGGAACTTCAGCGTGGGCAGAGAGGGCCTGGAATACGTCTGGGGC

AACCACGAGCCCGTGAGAGTGTGGGCCCAGGAAAGCGCCCCAGGCGACCC

CCACGGCTGGCCCCACGAGATCATCATCCACTACTACCACCGGCACCCCG

TGTACACCGTGATCGTGCTGTGCGGCGTGGCCCTGGCCATCCTGGTGGGC

ACCGCCAGCAGCGCCGCCTGCATCGCCAAGGCCAGGCGGGACTGCCTGAC

CCCCTACGCCCTGGCCCCCAACGCCACCGTGCCAACCGCCCTGGCCGTGC

TGTGCTGCATCCGGCCCACCAACGCCGAGACCTTCGGCGAGACCCTGAAC

CACCTGTGGTTCAACAACCAGCCCTTCCTGTGGGCCCAGCTGTGCATCCC

CCTGGCCGCCCTGATCATCCTGTTCCGGTGCTTCAGCTGCTGCATGCCTT

TTCTGCTGGTCGCCGGCGTGTGCCTGGGCAAGGTGGACGCCTTCGAGCAC

GCCACCACCGTGCCCAACGTGCCCGGCATCCCCTACAAGGCCCTGGTGGA

GAGGGCCGGCTACGCCCCCCTGAACCTGGAAATCACCGTGGTGTCCAGCG

AGCTGACCCCCTCCACCAACAAAGAATACGTGACCTGCAAGTTCCACACC

GTGGTGCCCTCCCCCCAGGTGAAGTGCTGCGGCAGCCTGGAATGCAAGGC

CAGCAGCAAGGCCGACTACACCTGCCGGGTGTTCGGCGGCGTGTACCCCT

TCATGTGGGCGGAGCACAGTGCTTCTGCGACTCCGAGAACACCCAGCTG

TCCGAGGCCTACGTGGAGTTCGCCCCCGACTGCACCATCGACCACGCCGT

GGCCCTGAAGGTGCACACAGCCGCCCTGAAAGTGGGCCTGCGGATCGTGT

ACGGCAACACCACCGCCAGGCTGGACACCTTCGTGAACGGCGTGACCCCC

GGCAGCAGCCGGGACCTGAAGGTGATCGCCGGACCCATCTCCGCCGCCTT

CAGCCCCTTCGACCACAAGGTGGTGATCCGGAAGGGCCTGGTGTACAACT

ACGACTTCCCCGAGTACGGCGCCATGAACCCTGGCGCCTTCGGCGACATC

CAGGCCAGCTCCCTGGACGCCACCGACATCGTGGCCCGGACCGACATCCG

GCTGCTGAAGCCCAGCGTGAAGAACATCCACGTGCCCTACACCCAGGCCG

TGAGCGGCTACGAGATGTGGAAGAACAACAGCGGCAGACCCCTGCAGGAA

ACCGCCCCCTTCGGCTGCAAGATCGAGGTGGAGCCCCTGCGGGCCACCAA

CTGCGCCTACGGCCACATCCCCATCAGCATCGACATCCCCGACGCCGCCT

TCGTGCGGAGCAGCGAGAGCCCCACCATCCTGGAAGTGAGCTGTACCGTG

GCCGACTGCATCTACAGCGCCGACTTCGGCGGCTCCCTGACCCTGCAGTA

CAAGGCCAACCGGGAGGGCCACTGCCCCGTGCACAGCCACAGCACCACCG

CCGTGCTGAAAGAGGCCACCACCCACGTCACCGCCACAGGCAGCATCACC

CTGCACTTCAGCACCAGCTCCCCCAGGCCAACTTCATCGTGAGCCTGTG

CGGCAAGAAAACCACCTGCAACGCCGAGTGCAAGCCCCTGCCGACCACA

TCATCGGCGAGCCTCACAAGGTGGACCAGGAATTCCAGGCCGCCGTCAGC

AAGACCAGCTGGAACTGGCTGCTGGCCCTGTTCGGCGGAGCCAGCAGCCT

GATCGTGGTGGGCCTGATTGTGCTGGTGTGCAGCAGCATGCTGATCAACA

CCCGGCGGTGATGA.
```

As used herein, a plasmid containing SEQ ID NO: 6 is referred to as "WEEV$_{COCAP}$ plasmid".

WEEV DNA Vaccine in Mice.

Figures 23A, 23B:
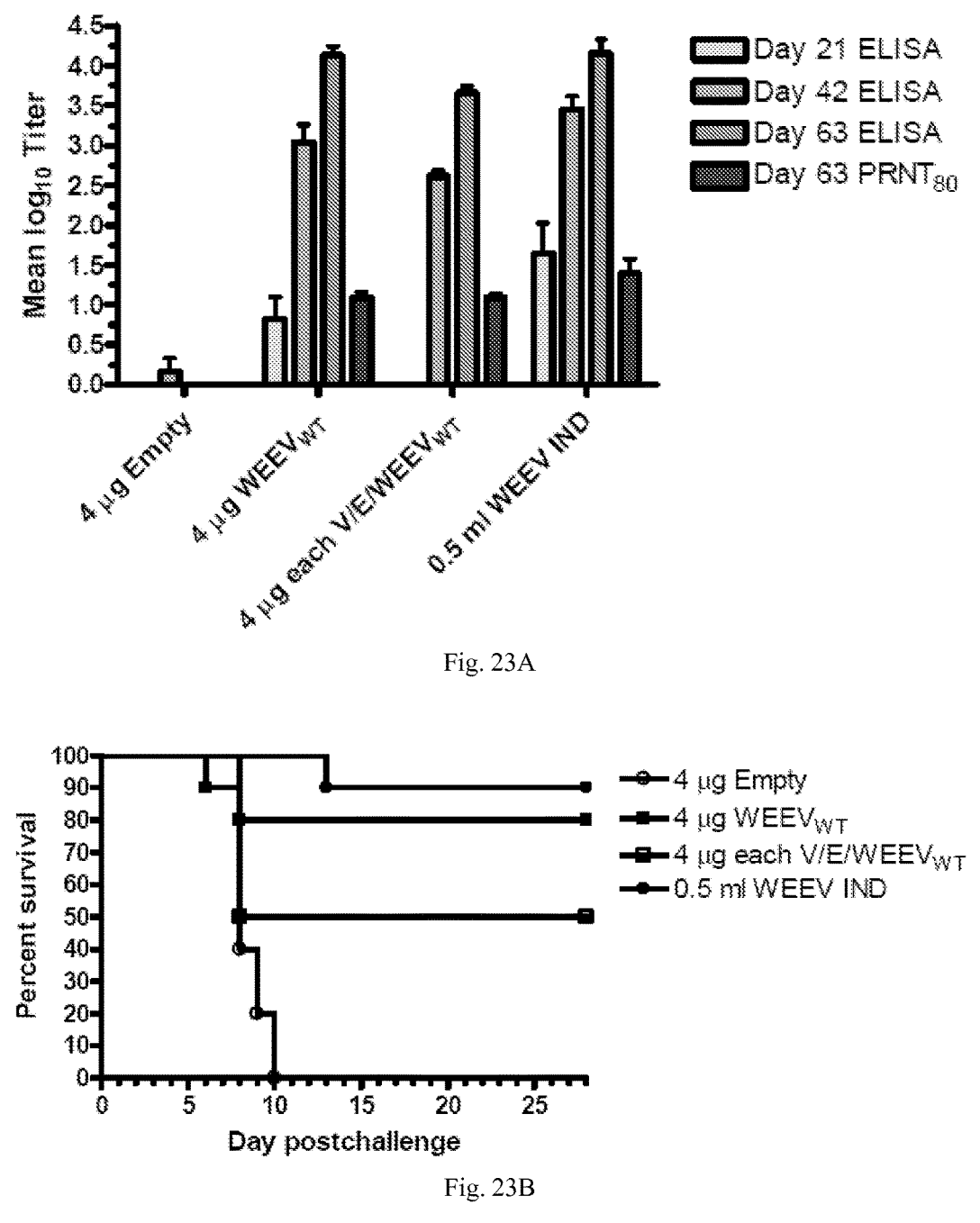

An initial study was performed to assess the immunogenicity and protective efficacy of WEEV$_{WT}$, a DNA plasmid expressing the wild-type structural proteins (C-E3-E2-6K-E1) of WEEV (strain CBA87), both alone and in combination with the VEEV$_{WT}$ and EEEV$_{WT}$ plasmids (WT combination). For this, groups of ten female BALB/c mice were vaccinated by PMED three times at 3-week intervals with 4 μg of the WEEV$_{WT}$ plasmid or a WT combination comprising 4 μg each of the WEEV$_{WT}$, VEEV$_{WT}$, and EEEV$_{WT}$ plasmids. A negative control group received 4 μg of the plasmid vector with no insert three times at 3-week intervals by PMED. A positive control group was vaccinated three times at 3-week intervals with 0.5 ml of the formalin-inactivated WEEV IND vaccine delivered by subcutaneous injection. Serum samples obtained 3 weeks after each vaccination were assayed for total anti-WEEV IgG antibodies by ELISA, and serum samples obtained three weeks after the third and final vaccination were also assayed for WEEV-neutralizing antibodies by PRNT. The mean ELISA titers of mice vaccinated with the WEEV$_{WT}$ plasmid alone were higher than those of mice vaccinated with the WT combination after each of the three vaccinations (FIG. 23A). Mice vaccinated with the WEEV$_{WT}$ plasmid alone or with the WT combination displayed similar low PRNT titers. To assess vaccine efficacy, the mice from all groups were challenged four weeks after the final vaccination with about $10^4$ PFU of WEEV strain CBA87 administered by the aerosol route. The survival rate of the mice vaccinated with WEEV$_{WT}$ alone was 80%, while 50% of those receiving the WT composition survived the challenge (FIG. 23B). Mice vaccinated with the WEEV IND were protected at a level of 90%.

To determine whether the WEEV DNA vaccine could be improved by employing the same strategy that proved successful for the VEEV and EEEV DNA vaccines, the wild type 26S structural genes minus the capsid sequence (E3-E2-6K-E1) of WEEV strain CBA87 (Genbank accession number DQ432026) were codon optimized by subjecting these genes to a GeneOptimizer™ bioinformatic algorithm (Geneart, Regensburg, Germany) for mammalian expression, and the codon optimized genes were synthesized using methods known in the art. The WEEV$_{CO}$ plasmid was constructed by cloning these synthesized codon optimized genes into the NotI and BglII restriction sites of pWRG7077 using methods known in the art.

Figures 24, 25A, 25B:
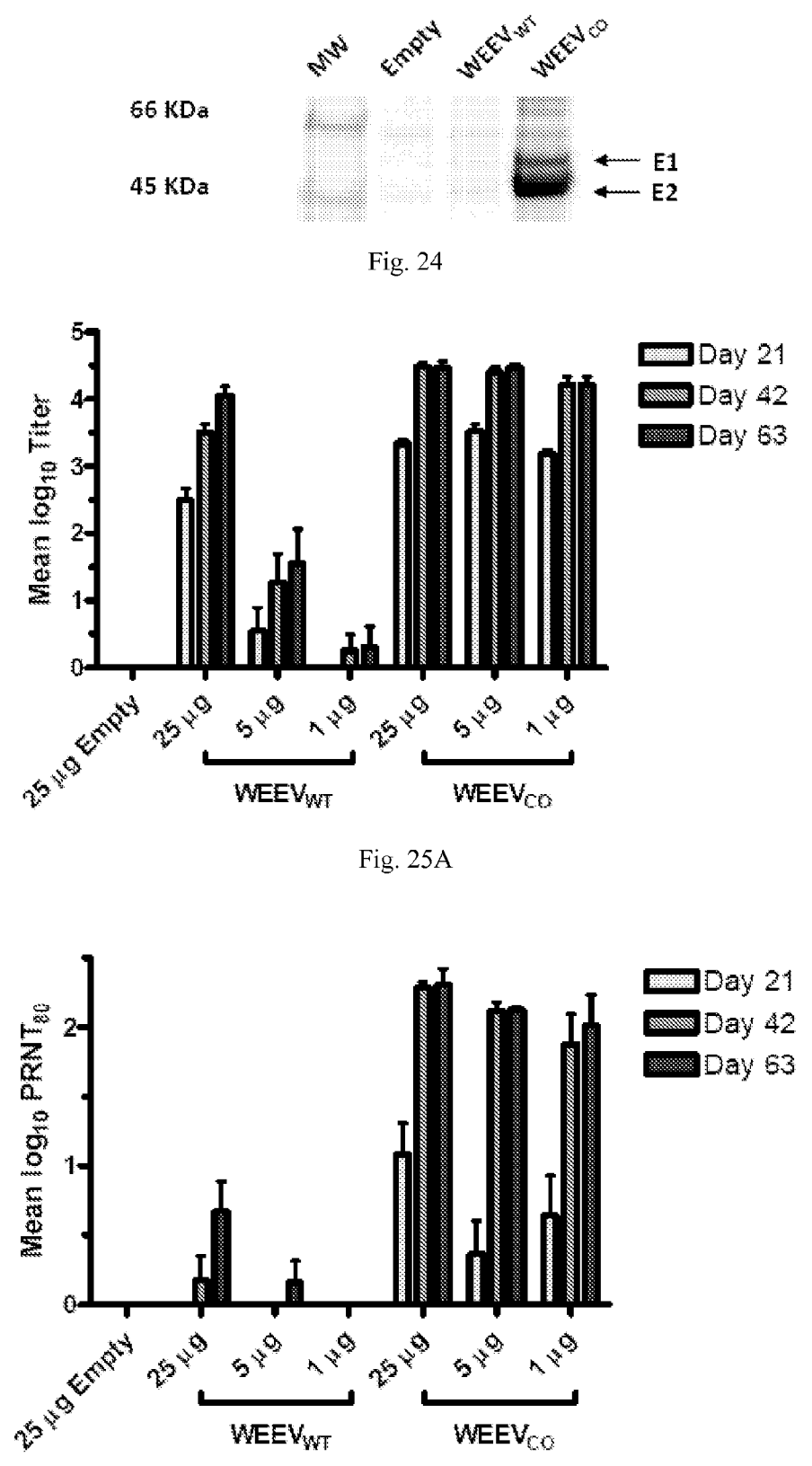

To determine if the WEEV$_{CO}$ vaccine construct showed improved expression of the envelope glycoproteins as compared to the previous WEEV$_{WT}$ construct, the proteins expressed in transiently transfected mammalian cells were detected by immune precipitation assay. The expression of the E2 and E1 envelope glycoproteins from the EEEV$_{CO}$ DNA was increased approximately tenfold relative to that of the VEEV$_{WT}$ construct in this assay (FIG. 24).

In an initial study to determine whether the immunogenicity of the WEEV$_{CO}$ plasmid was improved relative to the WEEV$_{WT}$ plasmid, groups of six female BALB/c mice were vaccinated by i.m. EP three times at 3-week intervals with 25 μg, 5 μg, or 1 μg of DNA. A negative control group received 25 μg of the plasmid vector with no insert. Serum samples obtained 3 weeks after each vaccination were assayed for total anti-WEEV IgG antibodies by ELISA and for WEEV-neutralizing antibodies by PRNT. The mean ELISA titers of mice vaccinated with the WEEV$_{CO}$ plasmid were significantly higher than those of mice vaccinated with the WEEV$_{WT}$ construct for the 5 µg and 1 µg dose groups after each of the three vaccinations (FIG. 25A). The mean PRNT$_{80}$ titer elicited by mice vaccinated with the WEEV$_{CO}$ plasmid was significantly higher than that observed for mice vaccinated with the WEEV$_{WT}$ construct for all dose groups at all days (FIG. 25B). In addition, the mean ELISA and PRNT titers of mice vaccinated with the WEEV$_{CO}$ plasmid were not significantly different after two and three vaccinations for all dose groups.

Figures 26A, 26B:
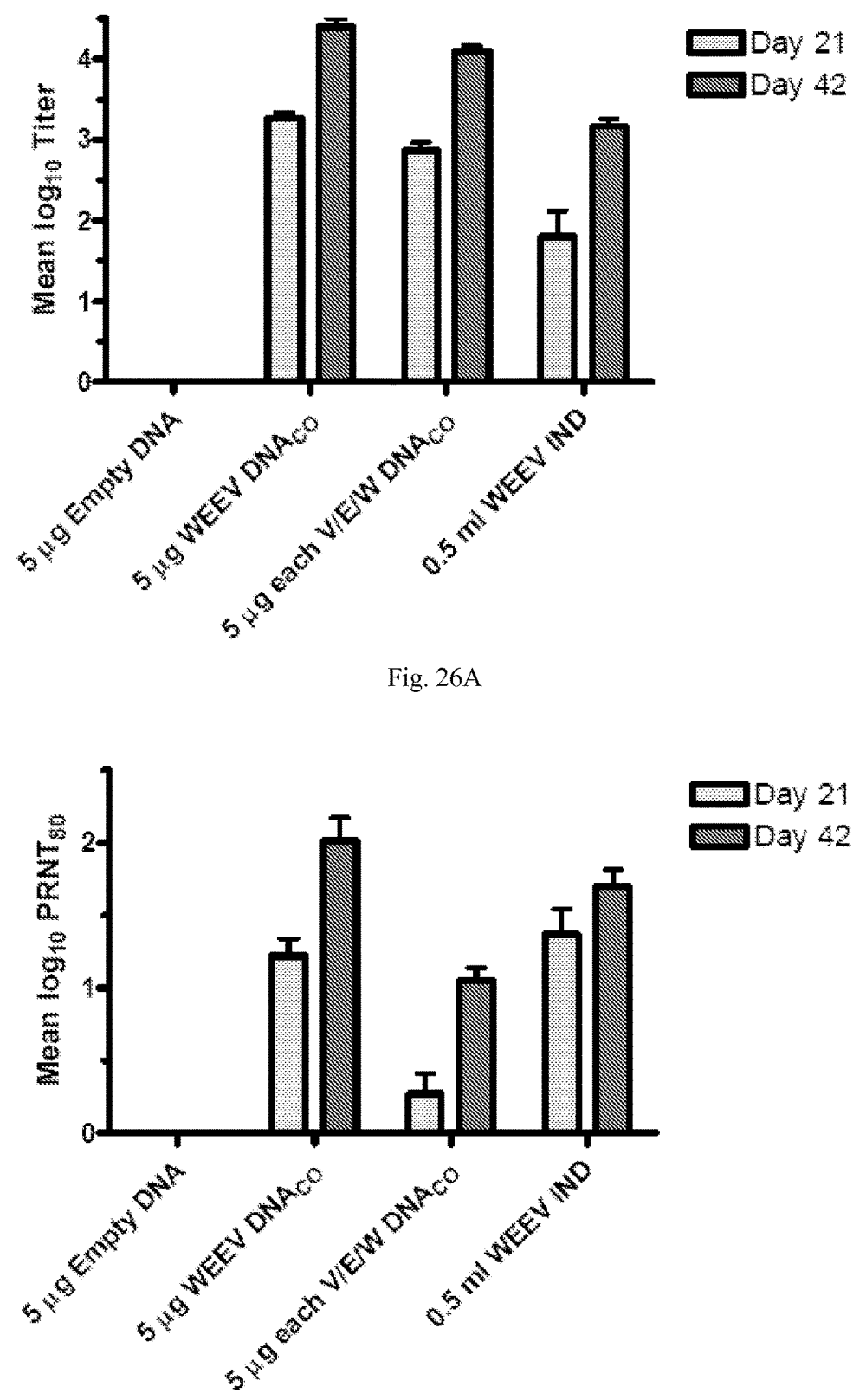

To determine the protective efficacy of the WEEV$_{CO}$ DNA vaccine both alone and in the multivalent EEV combination (combination composition), groups of ten female BALB/c mice were vaccinated by i.m. EP twice at a 3-week interval with 5 µg of the WEEV$_{CO}$ plasmid or a combination composition comprising 5 µg each of the WEEV$_{CO}$, VEEV$_{CO}$, and EEEV$_{CO}$ plasmids. A negative control group received the plasmid vector with no insert, and a positive control group received the formalin-inactivated WEEV IND vaccine. Serum samples obtained 3 weeks after each vaccination were assayed for total anti-WEEV IgG antibodies by ELISA and for WEEV-neutralizing antibodies by PRNT. The mean ELISA titers of mice vaccinated with the WEEV$_{CO}$ plasmid alone were not significantly different from those of mice vaccinated with the combination composition after each of the vaccinations (FIG. 26A). In addition, the mean ELISA titers of mice receiving the individual WEEV$_{CO}$ plasmid or the combination composition were higher than that of the WEEV IND after each of the vaccinations. The mean PRNT$_{80}$ titers elicited with the WEEV$_{CO}$ plasmid alone were significantly higher than those for the combination composition or the WEEV IND vaccine after each vaccination, and those of the combination composition were lower than those of the WEEV IND after each of the vaccinations (FIG. 26B). To assess vaccine efficacy, the mice from all groups were challenged four weeks after the second and final vaccination with about $10^4$ PFU of WEEV strain CBA87 administered by the aerosol route. Surprisingly, mice vaccinated with the individual WEEV$_{CO}$ plasmid and with the combination composition were completely protected from challenge (FIG. 26). In contrast, only 30% of mice receiving two vaccinations with the WEEV IND vaccine survived the challenge.

WEEV DNA Vaccine in Rabbits.

Figures 27, 28:
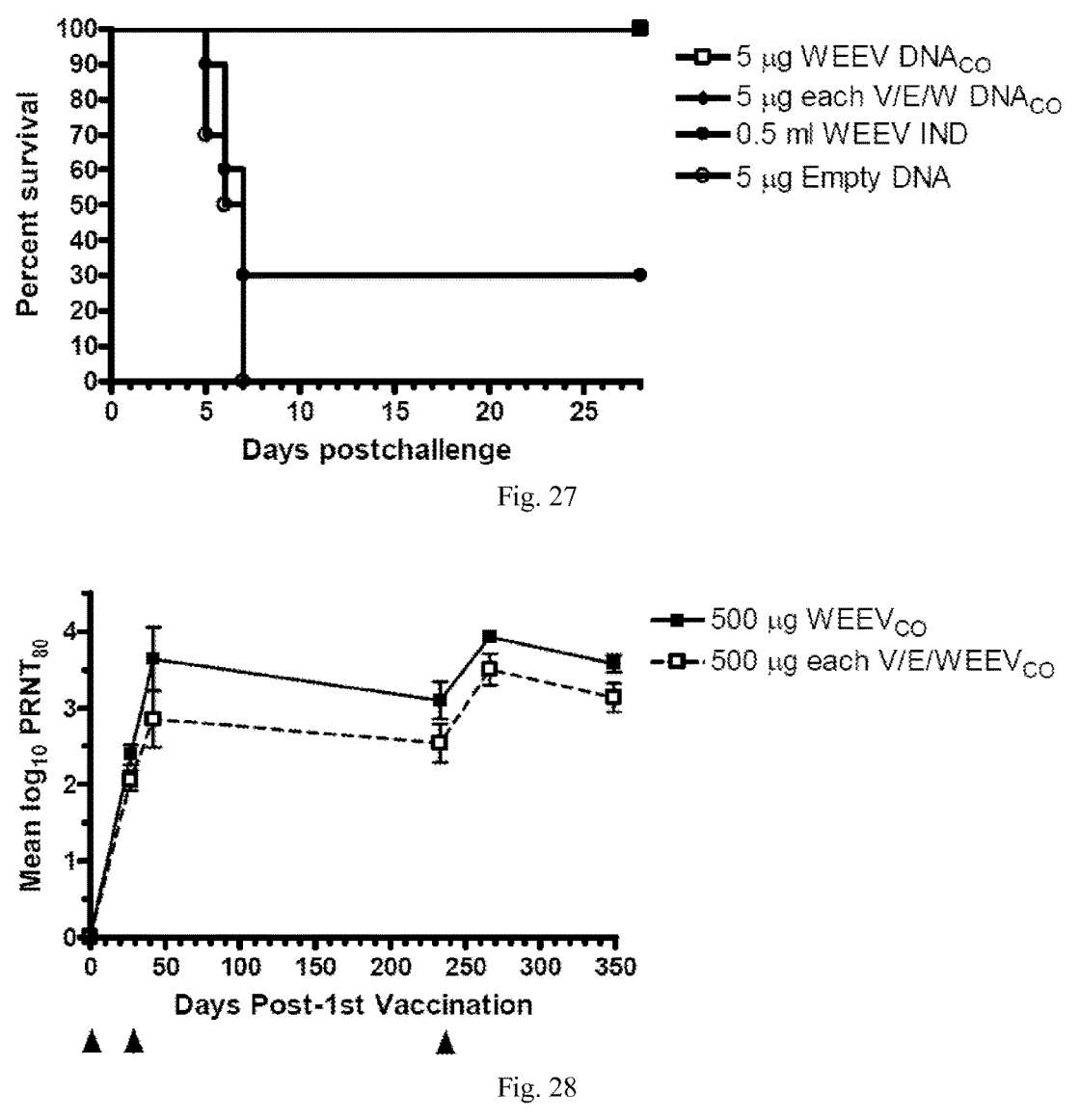

To assess the immunogenicity of the WEEV$_{CO}$ DNA vaccine alone and in the multivalent EEV combination (combination composition) in another species, female New Zealand White rabbits (N=5) were vaccinated with 500 µg of the WEEV$_{CO}$ plasmid or a combination composition comprising 500 µg each of the WEEV$_{CO}$, VEEV$_{CO}$, and EEEV$_{CO}$ plasmids delivered by i.m. EP on days 0, 28, and 230, and their antibody responses to WEEV were measured on days 0, 28, 42, 230, 266, and 349 by PRNT. The rabbits of both groups produced high titers of WEEV-neutralizing antibodies after a single vaccination and upon receiving a second vaccination, their mean PRNT$_{80}$ titers were significantly boosted (FIG. 28). The PRNT$_{80}$ titer of rabbits receiving the combination composition was lower than those of rabbits receiving the individual WEEV$_{CO}$ plasmid on all days, yet they still remained remarkably high. In addition, the mean PRNT$_{80}$ titers of both groups were boosted after an additional DNA vaccination performed on day 230.

WEEV DNA Vaccine in Cynomolgus Macaques.

Figures 29, 30A:
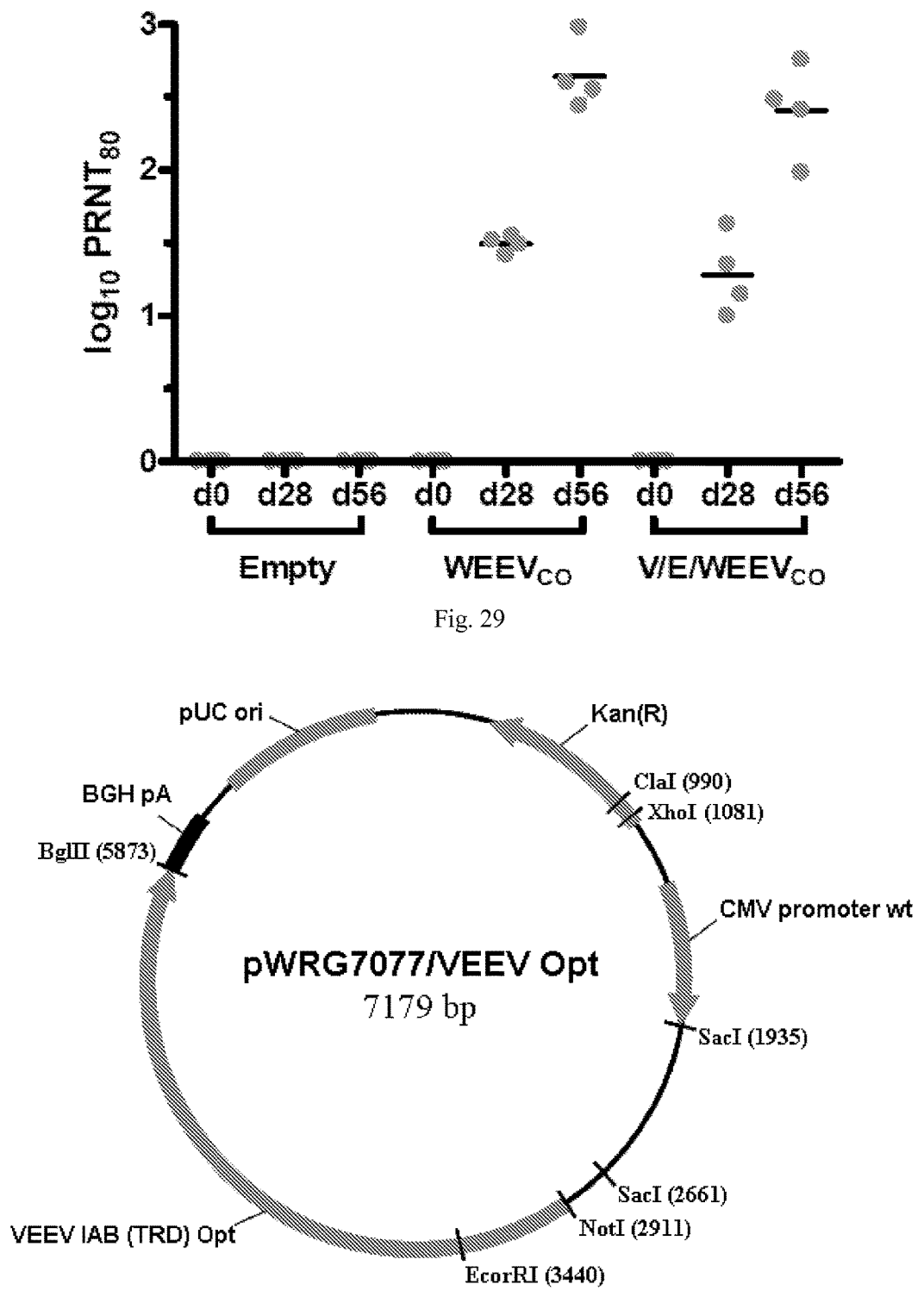

The immunogenicity and protective efficacy of the WEEV$_{CO}$ plasmid, both alone and in the multivalent EEV combination (combination composition), was assessed using an established model of WEEV infection of nonhuman primates. See Reed et al. (2005) J Infect Dis 192:1173-82. Groups of four adult male cynomolgus macaques were vaccinated three times at 4-week intervals with each animal receiving 500 µg of the empty vector DNA plasmid, 500 µg of the WEEV$_{CO}$ plasmid, or a combination composition comprising 500 µg each of the WEEV$_{CO}$, VEEV$_{CO}$, and EEEV$_{CO}$ plasmids delivered by i.m. EP. Serum samples collected 4 weeks after each vaccination were analyzed for WEEV-neutralizing antibodies by PRNT. Similar mean neutralizing antibody titers were elicited in macaques after a single vaccination with the individual WEEV$_{CO}$ plasmid and with the combination composition, and the titers of both groups were significantly and similarly boosted after the second vaccination (FIG. 29). The day 85 mean titers of these groups are currently being determined. The vaccinated macaques will be challenged with about $1.0 \times 10^8$ PFU of WEEV CBA87 at eight weeks after the third and final vaccination, and the protective efficacy will be evaluated in a similar manner to that previously done for VEEV and WEEV.

Taken together, these results indicate that codon-optimized sequences that encode structural proteins of EEVs and exclude sequences that encode the capsid proteins of EEVs elicit robust and durable protective immune responses with low DNA doses and few vaccinations. These results also indicate that EP delivery is an effective method to elicit immunity in subjects, with a capacity large enough to accommodate more than one EEV nucleic acid molecule in a single administration. Therefore, the present invention provides compositions which comprise at least one codon-optimized sequence that encodes one or more structural proteins except the capsid protein of a given EEV, such as EEEV, VEEV or WEEV. In some embodiments, the compositions comprise more than one codon-optimized sequence that encodes one or more structural proteins except the capsid protein of a given EEV. In these embodiments, the EEV may be the same or different. In some embodiments, the present invention provides combination compositions which comprise, consists essentially of, or consists of VEEV$_{CO}$, EEEV$_{CO}$, and WEEV$_{CO}$ nucleic acid molecules and treatment methods using such.

As used herein, the term "comprising" is used in its conventional sense to indicate that the given composition (or method) may include other ingredients (or steps). As used herein, the term "consisting of" is used in its conventional sense to indicate that the given composition (or method) may not include any additional ingredients (or steps). As used herein, the phrase "consisting essentially of" indicates that the given composition (or method) may include other ingredients (or steps) so long as the additional ingredients (or steps) do not materially change the biological and/or chemical activity (or results) of the specified ingredients (or steps). For example, a composition which consists essentially of VEEV$_{CO}$, EEEV$_{CO}$, and WEEV$_{CO}$ may contain additional ingredients so long as the additional ingredients do not change the biological activity, e.g. immunogenicity, of VEEV$_{CO}$, EEEV$_{CO}$, and WEEV$_{CO}$ as compared to a composition which consists of VEEV$_{CO}$, EEEV$_{CO}$, and WEEV$_{CO}$. Similarly, a method which consists essentially of step A, step B, and step C, may include additional steps so long as the additional steps do not materially change the results of performing only steps A, B, and C.

As used herein, an "EEV$_{CO}$ polynucleotide" refers to a nucleotide sequence which encodes a plurality of structural proteins, except the capsid, of an equine encephalitis virus selected from the group consisting of VEEV, EEEV and WEEV. In some embodiments, the nucleotide sequence is codon-optimized for mammalian, preferably human, expression. In some preferred embodiments, the nucleotide sequence has at least about 85%, preferably about 90%, more preferably about 95%, or most preferably about 99% or more sequence identity to SEQ ID NO:1, SEQ ID NO:3, SEQ ID NO:5, SEQ ID NO:7, SEQ ID NO:8 or SEQ ID NO:9. In some preferred embodiments, the nucleotide sequence is selected from the group consisting of SEQ ID NO:1, SEQ ID NO:3, SEQ ID NO:5, SEQ ID NO:7, SEQ ID NO:8 and SEQ ID NO:9. As used herein, the terms "polynucleotide", "nucleic acid molecule", and "nucleotide sequence" are used interchangeably.

As set forth herein, where a first set of variables are set forth and then a second set of variables are indicated for the first set of variables, such a description is to be construed as if the second set of variables was explicitly indicated for each member of the first set of variables. For example, in the above paragraph, the third sentence shall be construed as explicitly indicating "In some preferred embodiments, the nucleotide sequence has at least about 85%, preferably about 90%, more preferably about 95%, or most preferably about 99% or more sequence identity to SEQ ID NO:1, or in some preferred embodiments, the nucleotide sequence has at least about 85%, preferably about 90%, more preferably about 95%, or most preferably about 99% or more sequence identity to SEQ ID NO:3, or in some preferred embodiments, the nucleotide sequence has at least about 85%, preferably about 90%, more preferably about 95%, or most preferably about 99% or more sequence identity to SEQ ID NO:5, or in some preferred embodiments, the nucleotide sequence has at least about 85%, preferably about 90%, more preferably about 95%, or most preferably about 99% or more sequence identity to SEQ ID NO:7, or in some preferred embodiments, the nucleotide sequence has at least about 85%, preferably about 90%, more preferably about 95%, or most preferably about 99% or more sequence identity to SEQ ID NO:8, or in some preferred embodiments, the nucleotide sequence has at least about 85%, preferably about 90%, more preferably about 95%, or most preferably about 99% or more sequence identity to SEQ ID NO:9". In other words, all possible permutations are to be considered as being explicitly set forth. It is noted that this abbreviated manner of setting forth the embodiments of the instant invention is being used in the interests of reducing extra page fees.

Figures 30B, 30C:
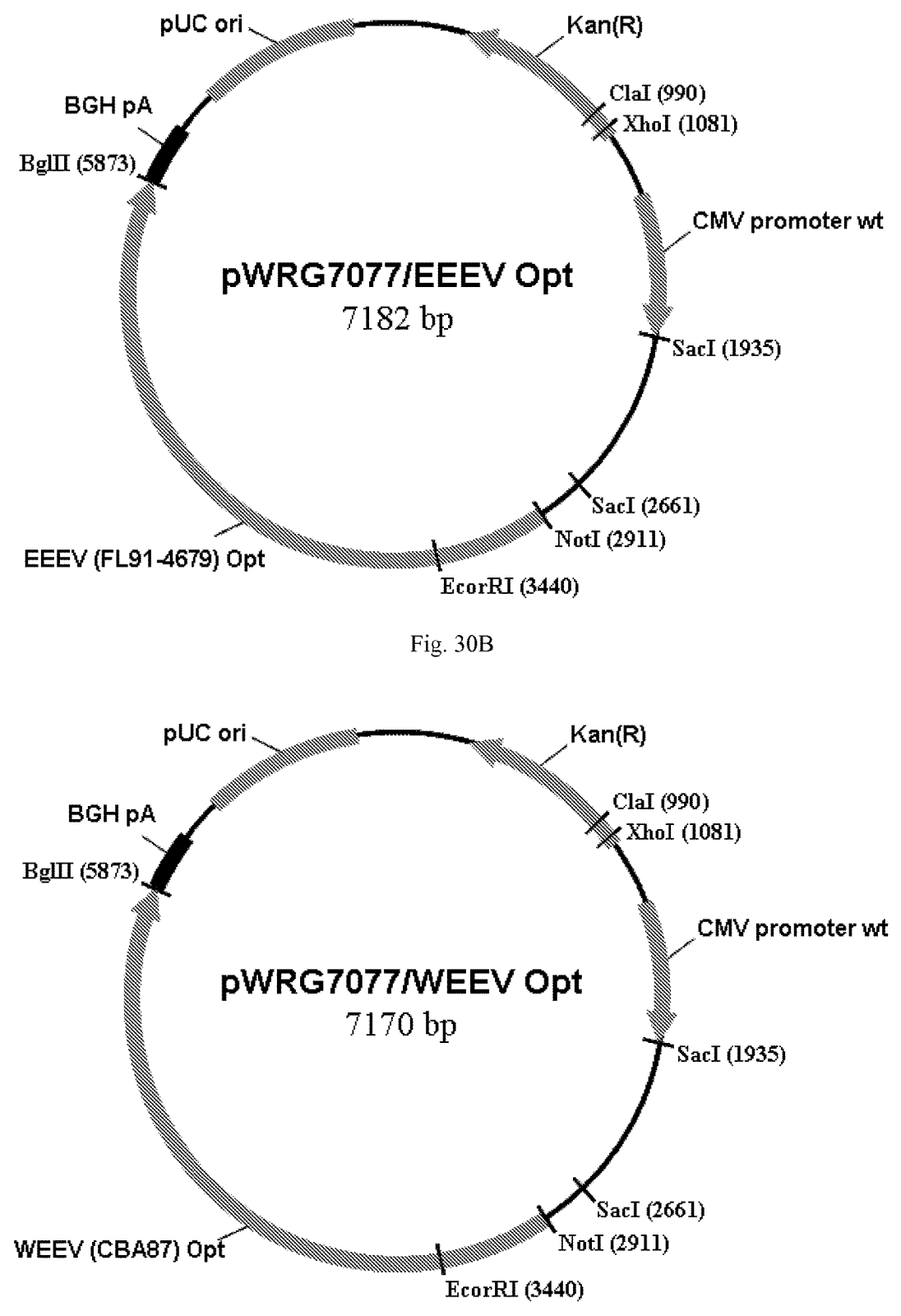

As used herein "EEV$_{CO}$ plasmid" refers to plasmid comprising, consisting essentially of, or consisting of a vector sequence and an EEV$_{CO}$ polynucleotide as described herein. In other words, an EEV$_{CO}$ plasmid refers to an EEV$_{CO}$ polynucleotide that is contained within a vector, such as an expression vector known in the art. In some embodiments, the EEV$_{CO}$ plasmids of the present invention that comprise an EEV$_{CO}$ sequence inserted therein. Examples of EEV$_{CO}$ plasmids include VEEV$_{CO}$, EEEV$_{CO}$, and WEEV$_{CO}$ plasmids as set forth in FIGS. 30A-30C.

As disclosed herein, the present invention provides VEEV$_{CO}$, EEEV$_{CO}$, and WEEV$_{CO}$ plasmids which may be used as DNA vaccines. The EEV$_{CO}$ plasmids of the present invention express the structural genes of the 26S subgenomic mRNA of these viruses minus the capsid protein coding region (E3-E2-6K-E1) that have been optimized to include several features known to increase mammalian expression. The VEEV$_{CO}$, EEEV$_{CO}$, and WEEV$_{CO}$ plasmids express the structural genes of VEEV subtype IAB strain Trinidad Donkey, EEEV strain FL91-4679, and WEEV CBA87, respectively, that were adapted to the codon bias of *Homo sapiens* genes. The codon adaptation index (CAI), a measure of how well the codons of the optimized sequence match the codon usage preference of the target organism, was raised from 0.74 to 0.98 for the VEEV genes, from 0.71 to 0.98 for the EEEV genes, and from 0.70 to 0.98 for the WEEV genes. In addition, regions of very high (>80%) or very low (<30%) guanine-cytosine (GC) content were avoided in the genes where possible. The average GC content was increased from 51% to 65% for the VEEV genes and from 50% to 65% for the EEEV and WEEV genes. The optimization process also included the avoidance of negatively cis-acting motifs in the genes which can hamper expression in mammals. For the VEEV genes, 9 prokaryotic inhibitory motifs, 1 polyadenylation site, 3 consensus splice donor sites, 4 cryptic splice donor sites, and 5 RNA instability motifs were avoided in the optimized gene sequence. For the EEEV genes, 6 prokaryotic inhibitory motifs, 1 polyadenylation site, 2 consensus splice donor sites, 3 cryptic splice donor sites, and 3 RNA instability motifs were avoided in the optimized gene sequence. For the WEEV genes, 9 prokaryotic inhibitory motifs, 1 polyadenylation site, 2 consensus splice donor sites, 4 cryptic splice donor sites, and 4 RNA instability motifs were avoided in the optimized gene sequence. In addition, Kozak sequence was introduced into the leader sequence of each of the optimized VEEV, EEEV, and WEEV structural gene open reading frames to increase translational initiation. Finally, two STOP codons were added at the ends of the optimized VEEV, EEEV, and WEEV structural gene open reading frames to ensure efficient termination. The optimized VEEV, EEEV, and WEEV structural gene open reading frames were then synthesized by Geneart, Inc. (Regensburg, Germany) and individually inserted between the NotI and BglII restriction sites of plasmid backbone pWRG7077 to create the final VEEV$_{CO}$, EEEV$_{CO}$, and WEEV$_{CO}$ plasmids that are exemplified herein. See FIGS. 30A-30C and the respective sequences. The pWRG7077 plasmid backbone contains the human cytomegalovirus immediate early (CMV IE) promoter with its associated Intron A, a bovine growth hormone transcription terminator and polyadenylation signal (BGH pA), a pUC19 origin of replication (ori), and a kanamycin resistance marker (KanR).

As used herein, an "EEV$_{CO}$ antibody" refers to an antibody raised against an EEV$_{CO}$ plasmid and/or an EEV$_{CO}$ polynucleotide.

As used herein, a "corresponding EEV$_{WT}$ control" refers to the wild type form of the item referenced. For example, a corresponding EEV$_{WT}$ control of VEEV$_{CO}$ is the corresponding wild type sequence, VEEV$_{WT}$. Similarly, the corresponding EEV$_{WT}$ control of a WEEV$_{CO}$ plasmid, is a plasmid which has the same vector sequence as the WEEV$_{CO}$ plasmid except that the polynucleotide contained therein is WEEV$_{WT}$. As another example, a corresponding EEV$_{WT}$ control of a combination composition (e.g. a composition comprising VEEV$_{CO}$, EEEV$_{CO}$, and WEEV$_{CO}$ polynucleotides) is a composition comprising VEEV$_{WT}$, EEEV$_{WT}$, and WEEV$_{WT}$ polynucleotides (WT combination) in the same amounts as that provided in the combination composition. It is important to note the differences between the WT, COCAP, and CO designations as used herein. The WT plasmids have inserts consisting of the wild-type full structural gene locus (C-E3-E2-6K-E1) of VEEV, EEEV or WEEV. The COCAP plasmids contain the full structural gene locus (C-E3-E2-6K-E1) of VEEV, EEEV, or WEEV that has been codon optimized. The CO plasmids contain the codon optimized structural gene locus of VEEV, EEEV, or WEEV minus the capsid (C) protein coding region (E3-E2-6K-E1). Therefore, the COCAP and CO plasmids are identical except for the lack of the codon optimized capsid coding region in the CO plasmids.

As used herein, a "subject" refers to a mammal, preferably a human who may be a patient, e.g. under the care of a physician.

The term "pharmaceutical composition" refers to a composition suitable for pharmaceutical use in a subject. A pharmaceutical composition generally comprises an effective amount of an active agent, e.g. an $EEV_{CO}$ plasmid, an $EEV_{CO}$ polynucleotide, or an $EEV_{CO}$ antibody according to the present invention, and a pharmaceutically acceptable carrier, e.g. a buffer, adjuvant, and the like. The term "effective amount" refers to a dosage or amount sufficient to produce a desired result. The desired result may comprise an objective or subjective improvement in the recipient of the dosage or amount, e.g. long-term survival, decrease in viremia, effective prevention of a disease state, and the like.

The $EEV_{CO}$ plasmid, $EEV_{CO}$ polynucleotide, or $EEV_{CO}$ antibody of the present invention may be administered, preferably in the form of pharmaceutical compositions, to a subject. Preferably the subject is mammalian, more preferably, the subject is human. Preferred pharmaceutical compositions are those comprising at least one immunogenic composition against VEEV, EEEV, WEEV, or a combination thereof, in an immunogenic amount or a therapeutically effective amount, and a pharmaceutically acceptable vehicle. The immunogenic composition may be an active immunizing agent, such as an $EEV_{CO}$ plasmid of the present invention, or a passive immunizing agent, such as an $EEV_{CO}$ antibody. The immunogenic composition may elicit an immune response that need not be protective or the immunogenic composition may provide passive immunity. $EEV_{CO}$ vaccines according to the present invention elicit a local or systemic immune response that is protective against subsequent challenge with an EEV virus, such as VEEV, EEEV, WEEV, or a combination thereof. Conventional methods in the art may be used to determine the feasibility of using the nucleic acid molecules of the present invention as vaccines against EEV infection. Accordingly, as used herein, an "immunogenic composition" can refer to vaccines as well as antibodies. A protective immune response may be complete or partial, i.e. a reduction in symptoms as compared with an unvaccinated mammal.

Thus, the present invention provides immunogenic compositions comprising at least one $EEV_{CO}$ plasmid and/or at least one $EEV_{CO}$ polynucleotide according to the present invention and/or at least one $EEV_{CO}$ antibody of the present invention that may be used to immunize a subject against one or more EEV by methods known in the art. As used herein, an "immunogenic amount" is an amount that is sufficient to elicit an immune response in a subject and depends on a variety of factors such as the immunogenicity of the $EEV_{CO}$ plasmid, the manner of administration, the general state of health of the subject, and the like. The typical immunogenic amounts for initial and boosting immunization for therapeutic or prophylactic administration ranges from about 0.01 mg to about 200 mg, preferably about 0.1-5.0 mg, more preferably about 0.5-2.0 mg, per about 65-70 kg body weight of a subject. For example, the typical immunogenic amount for initial and boosting immunization for therapeutic or prophylactic administration for a human subject ranges from about 0.01 mg to about 200 mg, preferably about 0.1-5.0 mg, more preferably about 0.5-2.0 mg, per about 65-70 kg body weight of a subject. Examples of suitable immunization protocols include initial immunization injections at time 0 and 4 or initial immunization injections at 0, 4, and 8 weeks, which initial immunization injections may be followed by further booster injections at 1 or 2 years.

As used herein, a "therapeutically effective amount" refers to an amount that may be used to treat, prevent, or inhibit a given condition, such as an EEV infection, in a subject as compared to a control. Again, the skilled artisan will appreciate that certain factors may influence the dosage required to effectively treat a subject, including the severity of EEV exposure, previous treatments, the general health and age of the subject, and the like. A therapeutically effective amount may be readily determined by conventional methods known in the art. It should be noted that treatment of a subject with a therapeutically effective amount of a given substance, e.g. an $EEV_{CO}$ plasmid, an $EEV_{CO}$ polynucleotide, or an $EEV_{CO}$ antibody according to the present invention, may be administered as a single dose or as a series of several doses.

The pharmaceutical compositions may include an adjuvant. As used herein, an "adjuvant" refers to any substance which, when administered with or before a pharmaceutically active agent, such as an $EEV_{CO}$ plasmid, aids the pharmaceutically active agent in its mechanism of action. Thus, an adjuvant in a vaccine is a substance that aids the immunogenic composition in eliciting an immune response. Suitable adjuvants include incomplete Freund's adjuvant, alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, nor-MDP), N-acetylmuramyl-Lalanyl-D-isoglutaminyl-L-alanine-2-(1'-2'-dipa-lmitoyl-sn-glycero-3-hydroxyphosphoryloxy)-ethylamine (CGP 19835A, MTP-PE), and RIBI, which comprise three components extracted from bacteria, monophosphoryl lipid A, trehalose dimycolate and cell wall skeleton (NPL+TDM+CWS) in a 2% squalene/Tween 80 emulsion. The effectiveness of an adjuvant may be determined by conventional methods in the art.

The compositions of the present invention may be administered to a subject by any suitable route including oral, transdermal, intranasal, inhalation, intramuscular, and intravascular administration. It will be appreciated that the preferred route of administration and pharmaceutical formulation will vary with the condition and age of the subject, the nature of the condition to be treated, the therapeutic effect desired, and the particular polypeptide, polynucleotide, or antibody used.

As used herein, a "pharmaceutically acceptable vehicle" or "pharmaceutically acceptable carrier" refers to and includes any and all solvents, dispersion media, coatings, antibacterial and antifungal agents, isotonic and absorption delaying agents, and the like, that are compatible with pharmaceutical administration. Pharmaceutically acceptable vehicles include those known in the art. See e.g. REMINGTON: THE SCIENCE AND PRACTICE OF PHARMACY. $20^{th}$ ed. (2000) Lippincott Williams & Wilkins. Baltimore, Md., which is herein incorporated by reference.

The pharmaceutical compositions of the present invention may be provided in dosage unit forms. "Dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The formulations of the compositions of the present invention may be optimized for increased stability and efficacy using methods known in the art. See e.g. Carra et al. (2007) Vaccine 25:4149-4158, which is herein incorporated by reference.

Toxicity and therapeutic efficacy of the polynucleotides and antibodies according to the instant invention and compositions thereof can be determined by standard pharmaceutical procedures in cell cultures or experimental animals. For example, one may determine the lethal dose, $LC_{50}$ (the dose expressed as concentration×exposure time that is lethal to 50% of the population) or the $LD_{50}$ (the dose lethal to 50% of the population), and the $ED_{50}$ (the dose therapeutically effective in 50% of the population) by conventional methods in the art. The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The present invention also provides $EEV_{CO}$ plasmids, $EEV_{CO}$ polynucleotides, $EEV_{CO}$ antibodies, and/or compositions thereof provided in kits along with instructions for use. A kit comprising a pharmaceutical composition may include the pharmaceutical composition as a single dose or multiple doses. The kit may include a device for delivering one or more $EEV_{CO}$ plasmids, one or more $EEV_{CO}$ polynucleotides, one or more $EEV_{CO}$ antibodies, and/or compositions thereof. The device may be a multi-chambered syringe for intramuscular delivery, a microneedle or set of microneedle arrays for transdermal delivery, a small balloon for intranasal delivery, or a small aerosol generating device for delivery by inhalation.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A plasmid comprising
   a vector sequence and
   a nucleotide sequence which encodes a plurality of structural proteins, except the capsid, of an equine encephalitis virus, wherein the nucleotide sequence has
   a) at least 85% sequence identity to SEQ ID NO:1, SEQ ID NO:3, or SEQ ID NO:5;
   b) at least 90% sequence identity to SEQ ID NO:1, SEQ ID NO:3, or SEQ ID NO:5;
   c) at least 95% sequence identity to SEQ ID NO:1, SEQ ID NO:3, or SEQ ID NO:5; or
   d) at least 99% sequence identity to SEQ ID NO:1, SEQ ID NO:3, or SEQ ID NO:5.

2. The plasmid according to claim 1, wherein the vector sequence is that of eukaryotic expression vector pWRG7077.

3. The plasmid according to claim 1, wherein the nucleotide sequence is selected from the group consisting of SEQ ID NO:1, SEQ ID NO:3, and SEQ ID NO:5.

4. The plasmid according to claim 1, wherein the sequence of the plasmid has
   a) at least 85% sequence identity to SEQ ID NO:7, SEQ ID NO:8, or SEQ ID NO:9;
   b) at least 90% sequence identity to SEQ ID NO:7, SEQ ID NO:8, or SEQ ID NO:9;
   c) at least 95% sequence identity to SEQ ID NO:7, SEQ ID NO:8, or SEQ ID NO:9; or
   d) at least 99% sequence identity to SEQ ID NO:7, SEQ ID NO:8, or SEQ ID NO:9.

5. A composition comprising one or more plasmids according to claim 1.

6. The composition according to claim 5, and further comprising a pharmaceutically acceptable carrier, an adjuvant, or both.

7. A method of eliciting an immune response in a subject which comprises administering to the subject an immunogenic amount of at least one plasmid according to claim 1 or a composition comprising the at least one plasmid.

8. The method according to claim 7, wherein the immune response is an observable cellular immune response.

9. The method according to claim 7, wherein the amount of the immune response is a total IgG antibody response and/or a neutralizing antibody response that is more than that provided by a corresponding $EEV_{WT}$ control.

10. The method according to claim 7, wherein the amount of the immune response is a total IgG antibody response and/or a neutralizing antibody response that is similar to that provided by TC-83.

11. The method according to claim 7, wherein the immunogenic amount is about 10-1250 µg/kg subject.

12. The method according to claim 7, wherein the immunogenic amount is administered by a particle-mediated epidermal delivery method.

13. A method of immunizing a subject against one or more equine encephalitis viruses which comprises administering to the subject an immunogenic amount of at least one plasmid according to claim 1 or a composition comprising the at least one plasmid.

14. The method according to claim 13, wherein the immunogenic amount confers to the subject 100% survivability against exposure to the one or more equine encephalitis viruses.

15. The method according to claim 14, wherein the one or more equine encephalitis viruses are selected from the group consisting of Venezuelan equine encephalitis virus (VEEV), western equine encephalitis virus (WEEV), and eastern equine encephalitis virus (EEEV).

16. The method according to claim 14, wherein the one or more equine encephalitis viruses are aerosolized.

17. The method according to claim 14, wherein the immunogenic amount is administered by a particle-mediated epidermal delivery method.

18. A composition comprising
1) a first plasmid comprising a vector sequence and a nucleotide sequence which encodes a plurality of structural proteins, except the capsid, of an equine encephalitis virus, wherein the nucleotide sequence has
   1a) at least 85% sequence identity to SEQ ID NO:1;
   1b) at least 90% sequence identity to SEQ ID NO:1;
   1c) at least 95% sequence identity to SEQ ID NO:1; or
   1d) at least 99% sequence identity to SEQ ID NO:1;
2) a second plasmid comprising a vector sequence and a nucleotide sequence which encodes a plurality of structural proteins, except the capsid, of an equine encephalitis virus, wherein the nucleotide sequence has
   2a) at least 85% sequence identity to SEQ ID NO:3;
   2b) at least 90% sequence identity to SEQ ID NO:3;
   2c) at least 95% sequence identity to SEQ ID NO:3; or
   2d) at least 99% sequence identity to SEQ ID NO:3; and
3) a third plasmid comprising a vector sequence and a nucleotide sequence which encodes a plurality of structural proteins, except the capsid, of an equine encephalitis virus, wherein the nucleotide sequence has
   3a) at least 85% sequence identity to SEQ ID NO:5;
   3b) at least 90% sequence identity to SEQ ID NO:5;
   3c) at least 95% sequence identity to SEQ ID NO:5; or
   3d) at least 99% sequence identity to SEQ ID NO:5.

19. A method of immunizing a subject against a plurality of equine encephalitis viruses which comprises administering to the subject an immunogenic amount of the composition according to claim 18.

* * * * *